United States Patent
Aki et al.

(10) Patent No.: US 10,759,741 B2
(45) Date of Patent: Sep. 1, 2020

(54) SEPARATING A SOLVENT FROM A NICKEL CATALYST BY DISTILLATION

(71) Applicant: INVISTA NORTH AMERICA S.A R.L., Wilmington, DE (US)

(72) Inventors: Sudhir N. V. K. Aki, Katy, TX (US); James M. Garner, Wilmington, DE (US); William J. Tenn, III, Beaumont, TX (US); Thomas E. Vos, Beaumont, TX (US)

(73) Assignee: INVISTA North America S.a r.l., Wilmington, DE (US)

( * ) Notice: Subject to any disclaimer, the term of this patent is extended or adjusted under 35 U.S.C. 154(b) by 296 days.

(21) Appl. No.: 14/904,726

(22) PCT Filed: Jul. 16, 2014

(86) PCT No.: PCT/US2014/046881
§ 371 (c)(1),
(2) Date: Jan. 13, 2016

(87) PCT Pub. No.: WO2015/009847
PCT Pub. Date: Jan. 22, 2015

(65) Prior Publication Data
US 2016/0168081 A1    Jun. 16, 2016

Related U.S. Application Data

(60) Provisional application No. 61/847,122, filed on Jul. 17, 2013.

(51) Int. Cl.
*C07C 253/10* (2006.01)
*C07C 253/34* (2006.01)
(Continued)

(52) U.S. Cl.
CPC .......... *C07C 253/10* (2013.01); *B01D 3/143* (2013.01); *B01J 31/185* (2013.01); *C07C 253/34* (2013.01)

(58) Field of Classification Search
CPC ... C07C 253/10; C07C 253/34; C07C 255/04; C07C 255/07; B01D 3/143; B01J 31/185
See application file for complete search history.

(56) References Cited

U.S. PATENT DOCUMENTS

| 3,496,215 A | 2/1970 | Drinkard et al. |
| 3,496,217 A | 2/1970 | Drinkard et al. |

(Continued)

FOREIGN PATENT DOCUMENTS

| EP | 1344770 A1 | 9/2003 |
| WO | 1995/011077 A2 | 4/1995 |

(Continued)

OTHER PUBLICATIONS

International Preliminary Report on Patentability Received for PCT Patent Application No. PCT/US2014/046881, dated Jan. 28, 2016, 6 pages.

(Continued)

*Primary Examiner* — Valerie Rodriguez-Garcia
(74) *Attorney, Agent, or Firm* — Robert B. Furr, Jr.; Edward F. Kenehan, Jr.

(57) ABSTRACT

A solvent is at least partially separated from a catalyst. The catalyst comprises nickel and a bidentate phosphorus-containing ligand. The method for separation involves distilling a catalyst solution. The ratio of 2-pentenenitrile to 3-pentenenitrile in distillation column bottoms is controlled to reduce the amount of 3-pentenenitrile which is isomerized to form 2-methyl-3-butenenitrile. Isomerization of 3-pentenenitrile to 2-methyl-3-butenenitrile and subsequent isomerization of 2-methyl-3-butenenitrile to 2-methyl-2-buteneni- (Continued)

trile, and/or hydrocyanation of 2-methyl-3-butenenitrile to methylglutaronitrile represents a loss in adiponitrile yield in a process for making adiponitrile.

10 Claims, 11 Drawing Sheets

(51) Int. Cl.
*B01D 3/14* (2006.01)
*B01J 31/18* (2006.01)

(56) References Cited

U.S. PATENT DOCUMENTS

| | | | |
|---|---|---|---|
| 3,496,218 A | 2/1970 | Drinkard | |
| 3,536,748 A | 10/1970 | Drinkard et al. | |
| 3,564,040 A * | 2/1971 | Downing | B01J 31/185 |
| | | | 558/335 |
| 3,631,191 A | 12/1971 | Kane et al. | |
| 3,655,723 A | 4/1972 | Drinkard | |
| 3,766,237 A | 10/1973 | Chia et al. | |
| 3,773,809 A | 11/1973 | Walter | |
| 3,852,325 A | 12/1974 | King | |
| 3,852,327 A | 12/1974 | Druliner et al. | |
| 3,852,329 A | 12/1974 | Tomlinson | |
| 3,865,865 A | 2/1975 | Musser et al. | |
| 3,903,120 A | 9/1975 | Shook, Jr. et al. | |
| 4,385,007 A | 5/1983 | Shook, Jr. | |
| 4,416,825 A | 11/1983 | Ostermaier | |
| 4,874,884 A | 10/1989 | McKinney et al. | |
| 5,512,696 A | 4/1996 | Kreutzer et al. | |
| 5,688,986 A | 11/1997 | Tam et al. | |
| 5,821,378 A | 10/1998 | Foo et al. | |
| 5,959,135 A | 9/1999 | Garner et al. | |
| 5,981,772 A | 11/1999 | Foo et al. | |
| 6,020,516 A | 2/2000 | Foo et al. | |
| 6,127,567 A | 10/2000 | Garner et al. | |
| 6,812,352 B2 | 11/2004 | Kreutzer et al. | |
| 6,893,996 B2 | 5/2005 | Chu et al. | |
| 6,936,171 B2 | 8/2005 | Jackson et al. | |
| 7,816,551 B2 | 10/2010 | Jungkamp et al. | |
| 8,088,943 B2 | 1/2012 | Foo et al. | |
| 2004/0176622 A1 | 9/2004 | Bartsch et al. | |
| 2007/0155978 A1* | 7/2007 | Jungkamp | C07C 253/10 |
| | | | 558/322 |
| 2007/0155979 A1 | 7/2007 | Rosier et al. | |
| 2007/0260086 A1 | 11/2007 | Rosier et al. | |
| 2008/0015382 A1* | 1/2008 | Foo | C07C 253/10 |
| | | | 558/338 |
| 2008/0221351 A1 | 9/2008 | Bartsch et al. | |
| 2008/0227998 A1 | 9/2008 | Scheldel et al. | |
| 2009/0099386 A1 | 4/2009 | Leconte et al. | |
| 2009/0187039 A1 | 7/2009 | Scheldel et al. | |

FOREIGN PATENT DOCUMENTS

| | | |
|---|---|---|
| WO | 2005/073179 A1 | 8/2005 |
| WO | 2008/008926 A2 | 1/2008 |
| WO | 2012/005910 A1 | 1/2012 |
| WO | 2012/033556 A1 | 3/2012 |
| WO | 2015/009847 A1 | 1/2015 |

OTHER PUBLICATIONS

International Search Report and Written Opinion Received for PCT Patent Application No. PCT/US2014/046881, dated Sep. 17, 2014, 8 pages.
Tolman et al., "Homogeneous Nickel-Catalyzed Olefin Hydrocyanation", Advances in Catalysis, vol. 33, 1985, pp. 1-46.
Yen et al., "Process Economics Program Report No. 546: NYLON 6.6", SRI International, Sep. 1987, pp. 201-214 & 571 (21 pp of Table of Contents attached).
Coutinho, Decio Heringer, "Nylon Intermediates Refining", Section of the PhD thesis, University of Texas at Dallas, Dec. 2001.

* cited by examiner

SEPARATING A SOLVENT FROM A NICKEL CATALYST BY DISTILLATION

FIELD OF THE INVENTION

The invention relates to a method for at least partial separation of a solvent from a catalyst, comprising nickel and a bidentate phosphorus-containing ligand, by distillation.

BACKGROUND OF THE INVENTION

Adiponitrile (ADN) is a commercially important and versatile intermediate in the industrial production of nylon polyamides useful in forming films, fibers, and molded articles. ADN may be produced by hydrocyanation of 1,3-butadiene (BD) in the presence of transition metal complexes comprising various phosphorus-containing ligands. For example, catalysts comprising zero-valent nickel and monodentate phosphorus-containing ligands are well documented in the prior art; see, for example, U.S. Pat. Nos. 3,496,215; 3,631,191; 3,655,723 and 3,766,237; and Tolman, C. A., McKinney, R. J., Seidel, W. C., Druliner, J. D., and Stevens, W. R., Advances in Catalysis, 1985, Vol. 33, pages 1-46. Improvements in the hydrocyanation of ethylenically unsaturated compounds with catalysts comprising zero-valent nickel and certain multidentate phosphite ligands are also disclosed; e.g., see: U.S. Pat. Nos. 5,512,696; 5,821,378; 5,959,135; 5,981,772; 6,020,516; 6,127,567; and 6,812,352.

3-Pentenenitrile (3PN) may be formed through a series of reactions as illustrated below.

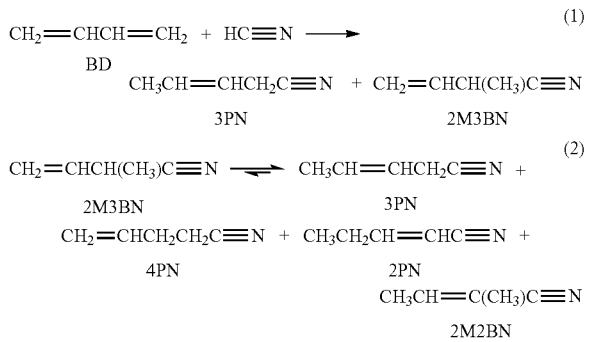

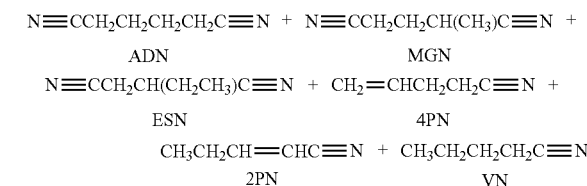

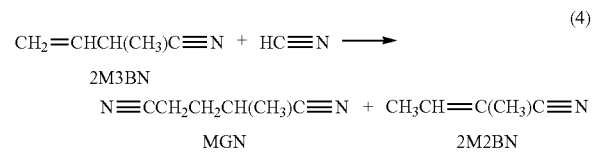

According to abbreviations used herein, BD is 1,3-butadiene, HC≡N is hydrogen cyanide, and 2M3BN is 2-methyl-3-butenenitrile. A method to increase the chemical yield of 3PN from BD hydrocyanation includes the catalytic isomerization of 2M3BN to 3PN (Equation 2 above) in the presence of $NiL_4$ complexes as disclosed in U.S. Pat. No. 3,536,748. Co-products of BD hydrocyanation and 2M3BN isomerization may include 4-pentenenitrile (4PN), 2-pentenenitrile (2PN), 2-methyl-2-butenenitrile (2M2BN), and 2-methylglutaronitrile (MGN).

In the presence of transition metal complexes comprising various phosphorus-containing ligands, dinitriles such as ADN, MGN, and ethylsuccinonitrile (ESN) may be formed by the hydrocyanation of 3PN and 2M3BN, as illustrated in Equations 3 and 4 below. Equation 4 also shows that 2M2BN can be formed when 2M3BN undesirably isomerizes in the presence of a Lewis acid promoter that may be carried over from a pentenenitrile hydrocyanation reaction zone.

The hydrocyanation of activated olefins such as conjugated olefins (e.g., 1,3-butadiene) can proceed at useful rates without the use of a Lewis acid promoter. However, the hydrocyanation of un-activated olefins, such as 3PN, require at least one Lewis acid promoter to obtain industrially useful rates and yields for the production of linear nitriles, such as ADN. For example, U.S. Pat. Nos. 3,496,217, 4,874,884, and 5,688,986 disclose the use of Lewis acid promoters for the hydrocyanation of non-conjugated ethylenically unsaturated compounds with nickel catalysts comprising phosphorous-containing ligands.

An integrated process for the production of ADN from BD and HC≡N can comprise BD hydrocyanation, 2M3BN isomerization to produce 3PN, and the hydrocyanation of pentenenitriles, including 3PN, to produce ADN and other dinitriles. Integrated processes are disclosed, for example, in United States Patent Application 2009/0099386 A1.

Disclosed in United States Patent Publication No. 2007/0260086, is a process for the preparation of dinitriles with an aim to provide for the recovery of a catalyst formed by a mixture of mono- and bidentate ligands and to be able to reuse the catalyst thus recovered in the hydrocyanation and/or isomerization stages.

United States Patent Publication No. 2008/0221351 discloses an integrated process for preparing ADN. A first process step includes hydrocyanating BD to produce 3PN over at least one zero-valent nickel catalyst. A second process step of the integrated process involves hydrocyanating 3PN to produce ADN over at least one zero-valent nickel catalyst and at least one Lewis acid. In this integrated process, at least one of the zero-valent nickel catalysts used in one of the process steps is transferred into the other process step.

United States Patent Application Publication 2007/0155978 discloses a method for recovering a catalyst from an extract by distillation. In the removal of the extractant to recover the catalyst, in a preferred embodiment, 3-pentenenitrile is added to the distillation as an intermediate boiler. One advantage of this solvent change is that effective depletion of the extractant from the high-boiling catalyst stream is possible at evaporator temperatures which are low enough not to thermally damage the particular nickel catalyst used and especially the chelate ligand. The pressure is still high enough to be able to condense the extractant having a comparatively low boiling point in comparison to the catalyst constituents at the top of the evaporator stage or distillation column even at customary cooling water temperatures of from 25 to 50° C.

United States Patent Application Publication 2007/0155979 describes a process for the hydrocyanation of unsaturated compounds to unsaturated mononitrile compounds or to dinitrile compounds. The reaction medium obtained after the hydrocyanation reaction is advantageously subjected to separation by distillation of the unreacted reactant, namely butadiene or the unsaturated nitrile, in order to be recycled. These separation stages are carried out while observing a distillation bottom temperature according to the conditions of ligand/nickel ratio and nickel concentration in order to avoid or limit decomplexing of the nickel and its precipitation.

United States Patent Application Publication 2009/0187039 describes a multistage process for distilling the effluent from a hydrocyanation reactor for reacting 1,3-butadiene with hydrogen cyanide. In one process step, an evaporator stage associated with a distillation apparatus is designed in such a way that the material to be evaporated is subject to very little thermal damage, as achieved, for example, by falling-film evaporators, multiphase helical tube evaporators, thin-film evaporators or short-path evaporators by short contact times of the material on the evaporator surface and very low temperatures of the evaporator surfaces. In a further preferred embodiment of the process, the distillation is carried out at average residence times of the liquid phase in the bottom region of the distillation apparatus of together less than 10 hours, more preferably less than 5 hours, in particular less than 1 hour. In a particularly preferred embodiment of the process, the distillation is carried out at average residence times of the liquid phase in the bottom region of the distillation apparatus in process steps of together less than 10 hours, more preferably less than 5 hours, in particular less than 1 hour. The absolute pressure in one process step is preferably from 0.001 to 10 bar, more preferably from 0.010 to 1 bar, in particular from 0.020 to 0.5 bar. The distillation is carried out in such a way that the temperature in the bottom of the distillation apparatus is preferably from 30 to 140° C., more preferably from 40 to 130° C., in particular from 50 to 120° C. The distillation is carried out in such a way that the condensation temperature at the top of the distillation apparatus is preferably from −20 to 140° C., more preferably from −10 to 80° C., in particular from −5 to 60° C. In a particularly preferred embodiment of the process, the aforementioned temperature ranges are maintained both at the top and in the bottom of the distillation apparatus.

It is reported in the prior art that, concomitant with the hydrocyanation of 3PN and 4PN to produce ADN, some isomerization of 3PN to cis- and trans-2PN can occur. However, in the process of hydrocyanating 3PN and 4PN using nickel catalysts derived from monodentate phosphite ligands, such as $Ni[P(OC_6H_5)_3]_4$, U.S. Pat. No. 3,564,040 states that the presence of 2PN, even in low concentrations, is detrimental to catalyst efficiency and the production of 2PN is undesirable since this presence and production of 2PN constitute a yield loss as well as a poison for the catalyst.

In order to address this issue, U.S. Pat. No. 3,564,040 describes a method to maintain the steady-state concentration of 2PN below 5 mole percent as based on the nitriles present in the reaction mixture. Because trans-2PN is difficult to separate from a mixture of 3PN and 4PN by distillation due to their close relative volatilities, the disclosed method involves the catalytic isomerization of trans-2PN to cis-2PN followed by fractional distillation of the mixture of pentenenitrile isomers to remove the more volatile cis-2PN Isomer. The catalyst systems used to isomerize trans-2PN to cis-2PN are those that also serve to hydrocyanate pentenenitriles to ADN, in particular, nickel catalysts derived from monodentate phosphite ligands as described in U.S. Pat. Nos. 3,496,217 and 3,496,218.

Alternative catalyst systems for the isomerization of trans-2PN to cis-2PN are disclosed in U.S. Pat. Nos. 3,852,325 and 3,852,327. The primary advantage of the catalyst systems described therein is in avoiding appreciable carbon-carbon double bond migration in the pentenenitrile isomers, which allows for the isomerization of trans-2PN to cis-2PN without substantial further isomerization of the 3PN to 2PN. The catalysts described in U.S. Pat. No. 3,852,325 are compounds of the general formula $R_3C$—X, such as triphenylmethyl bromide, wherein R is an aryl radical having up to 18 carbon atoms and —X is of the group consisting of —H, —Cl, —Br, —I, —SH, —$B(C_6H_5)_4$, —$PF_6$, —$AsF_6$, —$SbF_6$ and —$BF_4$, while the catalyst systems described in U.S. Pat. No. 3,852,327 are Lewis acid/Lewis base compositions, such as combinations of zinc chloride with triphenylphosphine.

A different method of removing the 2PN from mixtures of pentenenitrile isomers containing 3PN and 4PN is disclosed in U.S. Pat. No. 3,865,865. The 2PN and/or 2-methyl-2-butenenitriles (2M2BN) can be selectively separated from a mixture of pentenenitrile isomers containing 3PN and 4PN by contacting the mixture of nitriles with an aqueous solution of a treating agent comprising sulfite and bisulfite ions and ammonium or alkali metal cations to produce an aqueous phase containing the bisulfite adduct of the 2PN and/or 2M2BN and an organic phase containing the 3PN and 4PN, substantially free of 2PN and 2M2BN. The recovered organic phase is said to provide a feed material of pentenenitriles for further hydrocyanation to produce ADN with greatly reduced amounts of the undesired by-product 2PN, which is said to be detrimental to catalyst efficiency.

U.S. Pat. No. 6,127,567 discloses nickel catalyst compositions derived from bidentate phosphite ligands and processes for the hydrocyanation of monoethylenically unsaturated compounds which are said to be more rapid, selective, efficient, and stable than prior processes using nickel catalysts derived from monodentate phosphites. U.S. Pat. No. 5,688,986 discloses that at least one member of this class of catalysts is capable of hydrocyanating olefins conjugated to nitriles, for example 2PN.

U.S. Pat. No. 8,088,943 describes a process for the hydrocyanation of 3-pentenenitriles to produce ADN, using certain catalyst compositions described in U.S. Pat. No. 6,127,567 as well as other catalyst compositions.

U.S. Pat. No. 8,088,943 also describes a process for refining the reaction product mixture to obtain, for example, a stream comprising adiponitrile, a stream comprising a catalyst composition, and a stream comprising ethylenically unsaturated nitriles. The hydrocyanation process involves introducing 2-pentenenitrile along with 3-pentenenitrile as a feed to a hydrocyanation reactor to produce adiponitrile. The product from the hydrocyanation reactor is passed to an extraction step, for example, as described in U.S. Pat. No. 3,773,809. In the description of U.S. Pat. No. 8,088,943, the reaction product from the hydrocyanation reactor is passed directly to the extraction step without an intermediate distillation step to remove unreacted 3-pentenenitrile from the reaction product mixture.

U.S. Pat. No. 3,773,809 discloses a process for separating an organic phosphorus compound or a zerovalent nickel complex of the organic phosphorus compound from the reaction product of a hydrocyanation reaction of 3-pentenenitrile with hydrogen cyanide. The reaction product is contacted with a paraffin or cycloparaffin hydrocarbon solvent at a temperature of about 0° C. to about 100° C. to produce a multiphase mixture, wherein the organic phosphorus compounds and their metal complexes are contained predominantly in the hydrocarbon phase (i.e. the light phase) and the organic mono- and dinitrile and degradation products are contained predominately in a separate phase (i.e. a heavy or raffinate phase). In Example 1, the hydrocarbon solvent was cyclohexane (i.e. cyane), the hydrocarbon phase included 5.16 wt % of pentenenitriles, and the raffinate phase included 24.0 wt % of pentenenitriles. In Example 6, the hydrocarbon solvent was cyclohexane (i.e. cyane), and essentially all of the 2-pentenenitriles (i.e. trans-2-pentenenitrile and cis-2-pentenenitrile) were apparently found in the raffinate phase with no 2-pentenenitriles being reported in the hydrocarbon phase.

U.S. Pat. No. 7,816,551 describes a process for the hydrocyanation of 3-pentenenitrile to produce ADN, followed by distillation step to remove a portion of the unreacted 3-pentenenitrile from the hydrocyanation reaction product mixture, followed, in turn, by an extraction step to remove catalyst from the distilled reaction product mixture. The unreacted 3-pentenenitrile is removed from the distillation step in an overhead stream, and the catalyst is removed from the distillation step as a bottoms stream.

In addition to unreacted 3-pentenenitrile, the overhead stream comprises 2-pentenenitrile and (E)-2-methyl-2-butenenitrile. According to the description of U.S. Pat. No. 7,816,551, this overhead stream may be distilled to remove cis-2-pentenenitrile and (E)-2-methyl-2-butenenitrile prior to recycling the unreacted 3-pentenenitrile to the hydrocyanation reactor.

U.S. Pat. No. 7,816,551 further describes recovering unreacted 3-pentenenitrile from a raffinate stream obtained from the extraction step to remove catalyst from the distilled reaction product mixture. The raffinate stream is first distilled to remove residual extraction solvent from the stream. This distilled raffinate stream is then further distilled to remove pentenenitriles, comprising 3-pentenenitrile, 2-pentenenitrile and 2-methyl-2-butenenitrile as an overhead stream. This overhead stream may then be further distilled to remove cis-2-pentenenitrile and 2-methyl-2-butenenitrile in an overhead stream and to recover 3-pentenenitrile in a bottoms stream. The recovered 3-pentenenitrile may then be recycled to the hydrocyanation reactor. The above mentioned two distillation steps to remove cis-2-pentenenitrile and 2-methyl-2-butenenitrile from 3-pentenenitrile may take place in the same distillation apparatus.

SUMMARY OF THE INVENTION

Isomierization of 3-pentenenitrile to 2-methyl-3-pentenenitrile in distillation column bottoms represents a loss in adiponitrile yield in the process, as 2-methyl-3-butenenitrile may be subsequently converted via isomerization to 2-methyl-2-butenenitriles, and/or converted to 2-methylglutaronitrile via hydrocyanation. The inventors have made the unexpected discovery that isomerization of 3-pentenenitrile to 2-methyl-3-butenenitrile is reduced by controlling the ratio of 2-pentenenitrile to 3-pentenenitrile in these column bottoms.

A method is provided for increasing the concentration of catalyst in a catalyst solution. The catalyst solution comprises solvent and a catalyst. The solvent comprises 2-pentenenitrile and 3-pentenenitrile. The catalyst comprises nickel and a bidentate phosphorus-containing ligand.

The method for increasing the concentration of the catalyst comprises two steps. In a first step (a), the catalyst solution is introduced into a distillation zone. In a second step (b), solvent is evaporated from the catalyst in the distillation zone. The distillation conditions are sufficient to form a solvent-depleted catalyst solution comprising the catalyst, 2-pentenenitrile and 3-pentenenitrile. The ratio of 3-pentenenitrile to 2-pentenenitrile in the solvent-depleted catalyst solution may be 14 or less, for example, 14 to 0.1, for example, 12 to 0.1, for example, 10 to 0.1, for example, 7 to 0.1, for example, 5 to 0.1, for example, 3 to 0.1, for example, from 1 to 14, for example from 1 to 7, for example, from 1 to 3.

Catalyst solution, which is introduced into the distillation zone of step (a), may comprise at least one co-solvent which is miscible with the catalyst, 2-penetenenitrile and 3-pentenenitrile. At least a portion of the co-solvent may be evaporated in the distillation zone of step (a). The co-solvents may be liquids (at room temperature and pressure) which emerge as effluents from reaction zones (i) to produce 3-pentenentirle from the reaction of 1,3-butadiene with hydrogen cyanide, (ii) to produce 3-pentenenitrile by an isomerization reaction of 2-methyl-3-butenenitrile, and/or (III) to produce adiponitrile from the reaction of 3-pentenenitrile with hydrogen cyanide. Co-solvents, which may emerge along with product from a reaction zone to react 1,3-butadiene with hydrogen cyanide, include 1-butene, 1,3-butadiene, trans-2-butene, cis-2-butene, hydrogen cyanide, (Z)-2-methyl-2-butenenitrile, 4-vinyl-1-cyclohexene, (E)-2-methyl-2-butenenitrile, 2-methyl-3-butenenitrile and valeronitrile. Although they may, or may not, directly participate in the isomerization reaction of 3-pentenenitrile to 2-methyl-3-butenenitrile, by acting as diluents they may also suppress the overall amount isomerization of 3-pentenenitrile to 2-methyl-3-butenenitrile.

The hydrocyanation reaction to produce 3-pentenenitrile, the isomerization reaction to produce 3-pentenenitrile and the hydrocyanation reaction to produce adiponitrile may each take place in the presence of a diluent, which is preferably inert under the reaction conditions of the reactions. Examples of such diluents include hydrocarbons, such as one or more linear aliphatic hydrocarbons, one or more branched aliphatic hydrocarbons, one or more unsubstituted cycloaliphatic hydrocarbons, one or more alkyl-substituted cycloaliphatic hydrocarbons, one or more aromatic hydrocarbons. Accordingly, when these diluents are used, the effluents of one or more of the two hydrocyanation reaction zones and the isomerization reaction zone may include these hydrocarbons, and these hydrocarbons may be evaporated in one or more distillation steps to produce one or more concentrated catalyst solutions.

These hydrocarbons, particularly one or more linear aliphatic hydrocarbons, one or more branched aliphatic hydrocarbons, one or more unsubstituted cycloaliphatic hydrocarbons, one or more alkyl-substituted cycloaliphatic hydrocarbons, one or more aromatic hydrocarbons, may also be used as extraction solvents to recover catalyst from an effluent stream or a distilled fraction of an effluent stream. In particular, an effluent or a distilled fraction of an effluent stream may be introduced into an extraction zone along with the extraction solvent, and a liquid which is not entirely miscible with the extraction solvent, yet miscible with mononitriles, such as 3-pentenenitrile. Examples of such liquids include dinitriles, such as adiponitrile. Since dintriles tend to be more polar than the hydrocarbon extraction solvents, the liquid mixture of dinitiles and extraction solvent will tend to separate into two phases upon standing.

The upper phase may be separated from the lower phase. The separated phase comprising extraction solvent, may be distilled to recover an overhead stream enriched in extraction solvent and a bottoms stream enriched in catalyst. The overhead stream may be recycled to the extraction zone and the bottoms stream may be recycled to at least one of the above-mentioned reaction zones for hydrocyanation or isomerization. The distillation to produce the overhead and bottoms steam may take place under conditions, such that the ratio of 3-pentenenitrile to 2-pentenenitrile in the bottoms stream is 14 or less, for example, 14 to 0.1, for example, 7 to 0.1, for example, 3 to 0.1, for example, from 1 to 14, for example, from 1 to 7, for example, from 1 to 3.

When the catalyst solution, which is introduced into the distillation zone of step (a), comprises a hydrocarbon solvent selected from the group consisting of linear aliphatic, branched aliphatic, unsubstituted cycloaliphatic, and alkyl-substituted cycloaliphatic hydrocarbons, the hydrocarbon solvent may have a boiling point in the range of, for example, 30° C. to 135° C., for example, from 60° C. to 105° C., at one atmosphere pressure.

In summary, according to one embodiment, the catalyst solution, which is introduced into the distillation zone of step (a), may be an extracted catalyst solution formed by extracting catalyst from an effluent stream or distilled fraction of an effluent stream. The effluent stream may be the effluent stream from a reactor. The reactor may be (i) a reactor for reacting hydrogen cyanide with 1,3-butadiene to form a reaction product comprising 3-pentenenitrile, (II) a reactor for isomerizing 2-methyl-3-butenenitrile to form 3-pentenenitrile, or (iii) a reactor for reacting 3-pentenenitrile with hydrogen cyanide to form adiponitrile. The effluent stream or distilled fraction of the effluent stream may be contacted with an extraction solvent comprising one or more linear aliphatic hydrocarbons, one or more branched aliphatic hydrocarbons, one or more unsubstituted cycloaliphatic hydrocarbons, one or more alkyl-substituted cycloaliphatic hydrocarbons, and/or one or more aromatic hydrocarbons. The extraction solvent may be removed from the distillation zone as an overhead stream, and a solvent-depleted stream enriched in catalyst may be removed from the distillation zone as a bottoms steam. The ratio of 3-pentenenitrile to 2-pentenenitrile in the bottoms stream may be 14 or less, for example, 7 or less, for example, 3 or less, for example, from 1 to 14, for example from 1 to 7, for example from 1 to 3.

As stated above, the catalyst of the catalyst solution comprises nickel and at least one bidentate phosphorus-containing ligand. In particular, the nickel in the catalyst may be in the form of zero valent nickel (Nio). The bidentate phosphorus-containing ligand may comprise one or more of the ligands selected from the group consisting of a bidentate phosphite, a bidentate phosphonite, a bidentate phosphinite, a bidentate phosphine, and a mixed bidentate phosphorus-containing ligand.

The catalyst may further comprise at least one monodentate phosphorus-containing ligand. The monodentate phosphorus-containing ligand may be one or more ligands selected from the group consisting of monodentate phosphite, monodentate phosphonite, monodentate phosphinite, and monodentate phosphine. When the catalyst comprises both bidentate and monodentate phosphorus-containing ligands, the weight ratio of bidentate phosphorus-containing ligand to monodentate phosphorus-containing ligand may be at least 1:100, for example, at least 1:10, for example, at least 1:1, for example, at least 2:1, for example, at least 10:1, for example, at least 100:1.

Solvent may be evaporated from the catalyst solution in a distillation step performed by maintaining at least a portion of the catalyst solution under conditions sufficient to evaporate solvent from the catalyst solution. Examples of distillation methods include an adiabatic flash, a distillation at or above one atmosphere pressure, and a vacuum distillation.

Heat may be supplied to the distillation zone in a variety of ways to accomplish the desired evaporation of solvent and concentration of catalyst in the distillation zone bottoms. For example, the distillation may take place in a process comprising, as a first step (c), flowing a feed or a plurality of feeds comprising a solution of the catalyst into a feed stage of a distillation apparatus. In a second step (d), liquid, comprising solvent and catalyst, is withdrawn at a liquid draw point at or below the feed stage, at least a portion of the withdrawn liquid is heated to obtain a heated withdrawn liquid, and at least a portion of the heated withdrawn liquid is returned to the distillation apparatus. In one embodiment, 2-pentenenitrile may be added to the withdrawn liquid before it is returned to the distillation apparatus. In another embodiment, the heating of at least a portion of the withdrawn liquid is controlled such that the temperature of the withdrawn liquid is between 0° C. and 200° C., for example, 20° C. and 160° C., for example, 40° C. and 140° C., for example, 80° C. and 120° C.

According to one embodiment, the catalyst solution, which is introduced into the distillation zone of step (a), is an effluent stream from a reactor for reacting hydrogen cyanide with 1,3-butadiene in the presence of the catalyst to form 3-pentenenitrile, wherein unreacted 1,3-butadiene is a solvent evaporated from the catalyst in step (b).

According to another embodiment, the catalyst solution, which is introduced into the distillation zone of step (a), is a distilled fraction of an effluent stream from a reactor for reacting hydrogen cyanide with 1,3-butadiene in the presence of the catalyst to form 3-pentenenitrile, wherein the effluent from the reactor is passed through a first distillation zone, wherein a portion of unreacted 1,3-butadiene is removed in an overhead stream and the distillation bottoms from the first distillation zone is passed to a second distillation zone, and wherein the distillation bottoms is the catalyst solution of step (a) and the second distillation zone is the distillation zone of step (a).

According to another embodiment, the catalyst solution, which is introduced into the distillation zone of step (a), is an effluent stream from a reactor for isomerizing 2-methyl-3-butenenitrile in the presence of the catalyst, to form 3-pentenenitrile, and wherein 2-methyl-3-butenenitrile is a solvent evaporated from the catalyst in step (b).

According to another embodiment, the catalyst solution, which is introduced into the distillation zone of step (a), is an effluent stream from a reactor for reacting 3-pentenenitrile in the presence of the catalyst to form adiponitrile, and wherein unreacted 3-pentenenitrile is a solvent evaporated from the catalyst in step (b).

According to another embodiment, the catalyst solution, which is introduced into the distillation zone of step (a), is an extracted catalyst solution formed by extracting catalyst from an effluent stream or distilled fraction of an effluent stream, wherein the effluent stream is the effluent stream from a reactor, and wherein the reactor is selected from the group consisting of (i) a reactor for reacting hydrogen cyanide with 1,3-butadiene in the presence of the catalyst to form 3-pentenenitrile, (ii) a reactor for isomerizing 2-methyl-3-butenenitrile in the presence of the catalyst to form 3-pentenenitrile, and (iii) a reactor for reacting 3-pentenenitrile with hydrogen cyanide in the presence of the catalyst to form adiponitrile, wherein the effluent stream or distilled fraction of the effluent stream is contacted with an extraction solvent comprising one or more linear aliphatic hydrocarbons, one or more branched aliphatic hydrocarbons, one or more unsubstituted cycloaliphatic hydrocarbons, one or more alkyl-substituted cycloaliphatic hydrocarbons, and/or one or more aromatic hydrocarbons, wherein an extraction solvent is the solvent evaporated from the catalyst in step (b). Catalyst is extracted into the extraction solvent. This extracting also forms a raffinate stream comprising a mixture of 3-pentenenitrile, 2-pentenenitrile, and adiponitrile. The ratio of step (b) may be maintained by recovering a mixture of 3-pentenenitrile and 2-pentenenitrile from the raffinate stream and then contacting this mixture with the catalyst of the distillation zone, the reactor, or a combination thereof. The 2-pentenenitrile in the raffinate stream comprises cis 2-pentenenitrile, trans 2-pentenenitrile. The ratio of step (b) may be maintained by recovering cis 2-pentenenitrile from the raffinate stream and then contacting the cis 2-pentenenitrile with the catalyst of the distillation zone, the reactor, or a combination thereof.

The temperature of the solvent-depleted catalyst solution may be about 160° C. or less during the evaporating of step (b). For example, a temperature of the solvent-depleted catalyst solution may be controlled between 60° C. and 160° C. during the evaporating of step (b).

The ratio of step (b) may be maintained by controlling the composition of 3-pentenenitrile and 2-pentenenitrile in the catalyst solution introduced in step (a). For example, the ratio of step (b) may be maintained by controlling the composition of 3-pentenenitrile and 2-pentenenitrile in the catalyst solution introduced in step (a).

The ratio of step (b) may be maintained by recovering a mixture of 3-pentenenitrile and 2-pentenenitrile from catalyst in an effluent stream or distilled fraction of an effluent stream then contacting this mixture with the catalyst of the distillation zone, the reactor, or a combination thereof.

The ratio of step (b) may be maintained by recovering cis 2-pentenenitrile from catalyst in an effluent stream or distilled fraction of an effluent stream then contacting this cis 2-pentenenitrile with the catalyst of the distillation zone, the reactor, or a combination thereof.

In a particular embodiment, 3-pentenenitrile is reacted with hydrogen cyanide in the presence of a catalyst to form adiponitrile. The catalyst comprises nickel and a bidentate phosphorus-containing ligand. The method comprises steps (a), (b) and (c). Step (a) comprises Introducing a catalyst solution comprising the catalyst, 2-pentenenitrile, and the 3-pentenenitrile into a distillation zone. Step (b) comprises evaporating solvent from the catalyst in the distillation zone to form a solvent-depleted catalyst solution comprising the catalyst, 2-pentenenitrile, and the 3-pentenenitrile, while maintaining the ratio of 3-pentenenitrile to 2-pentenenitrile in said solvent-depleted catalyst solution at 14 or less. Step (c) comprises contacting the solvent-depleted catalyst solution, comprising the catalyst and the 3-pentenenitrile, with hydrogen cyanide and Lewis acid to form the adiponitrile.

DETAILED DESCRIPTION OF THE INVENTION

Figure 1:
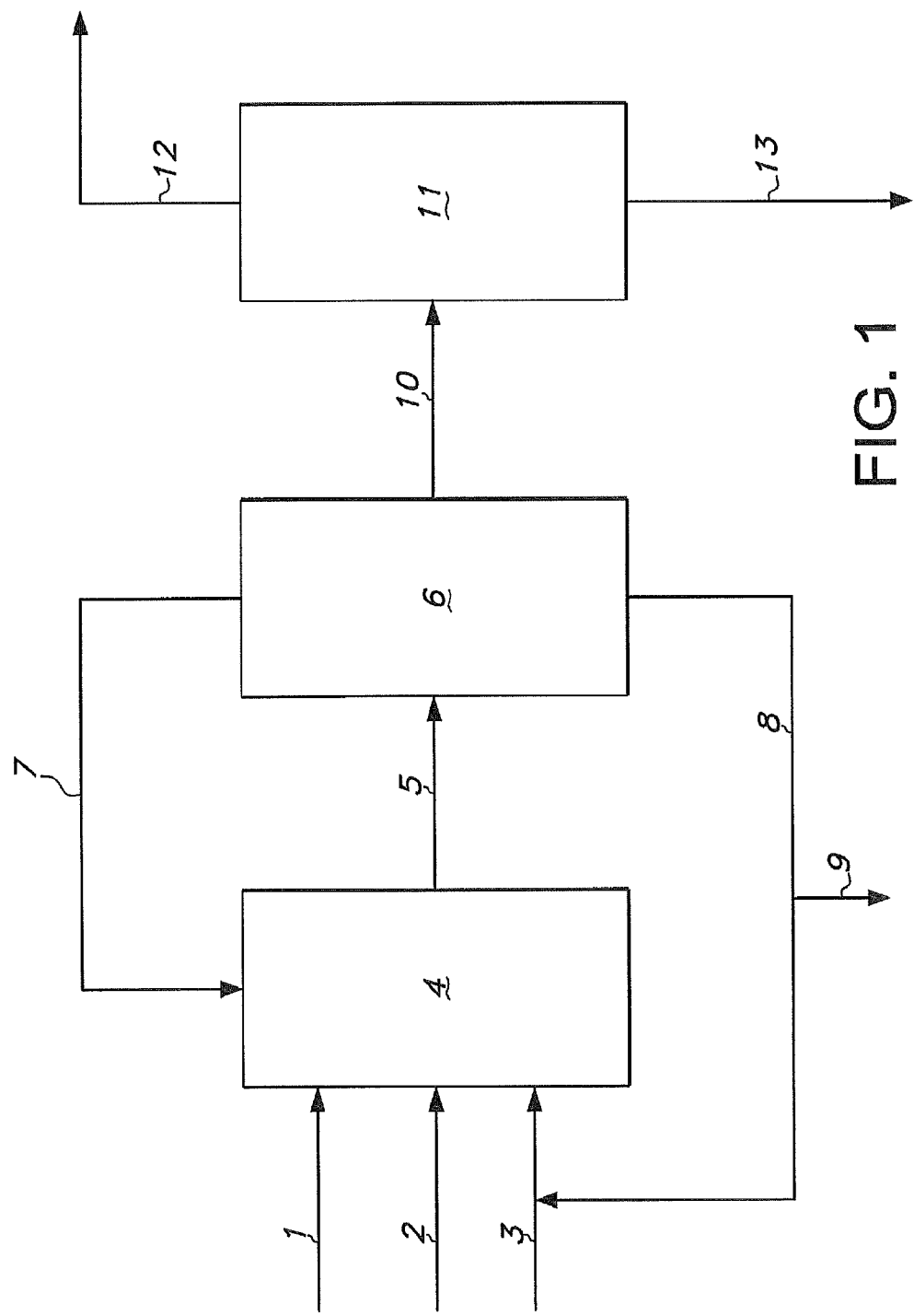
FIG. 1 is a schematic representation of aspects of a process for making pentenenitriles by the hydrocyanation of 1,3-butadiene.

Although the following detailed description contains many specifics for the purpose of illustration, a person of ordinary skill in the art will appreciate that many variations and alterations to the following details are within the scope of the herein disclosed embodiments.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "Including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Accordingly, the following embodiments are set forth without any loss of generality to, and without imposing limitations upon any claimed invention. Before the present disclosure is described in greater detail, it is to be understood that this disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

Certain abbreviations and definitions used herein include the following: ADN=adiponitrile; BD=1,3-butadiene; c2PN=cis-2-pentenenitrile; c3PN=cis-3-pentenenitrile; $C_8H_{13}C\equiv N$=diolefinic acyclic and monoolefinic cyclic mononitrile compounds of the chemical formula $C_8H_{13}C\equiv N$; $C_8H_4(C\equiv N)_2$=monoolefinic acyclic and aliphatic cyclic dinitrile compounds of the chemical formula $C_8H_{14}(C\equiv N)_2$; dinitrile or dinitriles=ADN, MGN, and ESN unless specifically limited; ESN=ethylsuccinonitrile; $HC\equiv N$ or HCN=hydrogen cyanide (i.e. hydrocyanic acid); 2M2BN=2-methyl-2-butenenitrile including both (E)-2M2BN and (Z)-2M2BN isomers unless specifically limited; 2M3BN=2-methyl-3-butenenitrile; (E)-2M2BN=(E)-2-methyl-2-butenenitrile or cis-2-methyl-2-butenenitrile; (Z)-2M2BN=(Z)-2-methyl-2-butenenitrile or trans-2-methyl-2-butenenitrile; MGN=2-methylglutaronitrile; organic mononitrile=an organic compound comprising a single nitrile group, for example, a pentenenitrile; organic dinitrile=an organic compound comprising two nitrile groups, for example, ADN; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile Including both c3PN and t3PN unless specifically limited; 4PN=4-pentenenitrile; ppm=parts per million by weight unless stated otherwise; t2PN=trans-2-pentenenitrile; t3PN=trans-3-pentenenitrile; VN=valeronitrile; VCH=4-vinyl-1-cyclohexene.

As used herein a boiling point (BP) of a compound refers to the temperature at which a pure form of the compound boils at atmospheric pressure. A listed boiling point is the temperature of a boiling point for a compound listed in at least one reliable source from the chemical literature.

As used herein, the terms "distillation apparatus" and "distillation column" are used interchangeably, and both of these terms generally refer to equipment for performing distillation steps. For the purposes of this disclosure, a flasher is considered to be a distillation column.

As described herein, the "first hydrocyanation reaction zone" is the hydrocyanation reaction zone for reacting 1,3-butadiene with HCN, the "isomerization reaction zone" is the reaction zone for isomerizing 2M3BN to make 3PN, and the "second hydrocyanation reaction zone" is the hydrocyanation reaction zone for reacting 3PN with HCN to make adiponitrile. The "first hydocyanation catalyst" is the catalyst used in the first hydrocyanation zone, the "isomerization catalyst" is the catalyst used in the isomerization reaction zone, and the "second hydrocyanation catalyst" is the catalyst used in the second hydrocyanation reaction zone.

Adiponitrile may be made from 1,3-butadiene by a series of reactions. A first reaction involves the hydrocyanation reaction of 1,3-butadiene with HCN to produce a mixture of 3-pentenenitrile (3PN) and 2-methyl-3-butenenitrile (2M3BN). The 2M3BN may be recovered from the mixture. 2M3BN recovered from the mixture is then isomerized in a second reaction to produce more 3PN. 3PN from the first hydrocyanation reaction and from the second isomerization reaction is then reacted with HCN in another hydrocyanation reaction to produce adiponitrile.

A catalyst may be used in the reactions to make 3PN, whether by hydrocyanation or by isomerization, and to make adiponitrile by hydrocyanation. The catalyst may comprise nickel, and a phosphorous containing ligand. The catalyst may be introduced into each of the reaction zones in the form of a solution comprising 3PN. The catalyst flows through each of the reaction zones and emerges from the reaction zones as an effluent along with products and unreacted reactants. The effluent may be treated to recover products, unreacted reactants and a concentrated catalyst solution. The concentrated catalyst solution may be recycled directly or indirectly to any of the reaction zones. The concentrated catalyst solution may be recycled indirectly to a reaction zone by first passing the concentrated catalyst solution through one or more purification steps prior to recycle.

Catalyst solutions emerging from reactions zones may be concentrated by one or more distillation steps. In these distillation steps, lower boiling compounds may be removed as overhead streams and higher boiling compounds may be recovered in bottoms streams. The higher boiling compounds may include nickel, phosphorous-containing ligands and 3PN. The higher boiling components in the bottoms of a distillation column may be subjected to conditions, particularly temperature conditions, sufficient to isomerize 3PN to 2M3BN in the presence of the catalyst in the bottoms.

2M3BN has a lower boiling point than 3PN. In particular, under atmospheric conditions, 2M3BN has been reported to have a boiling point of 125° C., and the Isomers of 3PN have been reported to have a boiling point of 144 to 147° C. When 3PN is isomerized to 2M3BN in the bottoms of a distillation column, at least a portion of the 2M3BN may tend to flow into the upper regions of the distillation column and be removed in an overhead stream. This process effectively converts the distillation column into a reactive distillation column, which serves to convert the desired product, 3PN, into the less desired product 2M3BN.

At least a portion of the 2M3BN, produced by isomerization of 3PN In distillation column bottoms, may also remain in the distillation column bottoms. Consequently, at least a portion of the 2M3BN produced by isomerization will be removed in the concentrated catalyst stream obtained from the column bottoms. The presence of 2M3BN in concentrated catalyst streams is problematic, when such streams are recycled to a hydrocyanation reaction zone. The recycle of 2M3BN to a hydrocyanation zone may result in the reaction of 2M3BN with HCN to produce methylglutanonitrile (MGN). Since the goal of the overall reaction scheme is to produce adiponitrile (ADN), the production of MGN should be avoided. In particular, unwanted isomerization of each mole of 3PN to 2M3BN may result in a loss of one mole of the desired product ADN and the production of a mole of unwanted MGN.

Prior to recycle of catalyst into a reaction zone, at least a portion of the catalyst may be purified or regenerated. The purification or regeneration process may involve removing various catalyst degradation products. Such catalyst degradation products include oxidized forms of nickel, such as nickel cyanide [$Ni(CN)_2$], and degraded forms of phosphorus-containing ligands, including hydrolysis and oxidation products.

Purification or regeneration may involve a liquid/liquid extraction process. Essentially all of the catalyst in the effluent from a reaction zone for converting 3PN and HCN may be treated in a liquid/liquid extraction process. A portion of catalyst in the effluent from a reaction zone, which is used for converting 1,3-butadiene and HCN into 3PN or a portion of the catalyst in the effluent from a reaction zone for isomerizing 2M3BN to 3PN, may be treated in a liquid/liquid extraction process. The portion of the catalyst, which is treated may be taken from a purge or side stream of concentrated catalyst, which is recycled to a reaction zone.

A concentrated catalyst stream from a reaction zone for converting 1,3-butadiene and HCN into 3PN and/or from a reaction zone for isomerizing 2M3BN to 3PN may be introduced into a liquid/liquid extraction zone along with an extraction solvent and a liquid which is at least partially immiscible with the extraction solvent. The catalyst in the concentrated catalyst stream is more soluble in the extraction solvent than in the liquid which is at least partially immiscible with the extraction solvent. The extraction solvent may be a nonpolar solvent such as a hydrocarbon solvent, for example, one or more linear aliphatic hydrocarbons, one or more branched aliphatic hydrocarbons, one or more unsubstituted cycloaliphatic hydrocarbons, one or more alkyl-substituted cycloaliphatic hydrocarbons, and/or one or more aromatic hydrocarbons. The liquid, which is at least partially immiscible with the extraction solvent, may be a liquid, which is more polar than the extraction solvent. Examples of such relatively polar liquids Include dinitriles, such as adiponitrile (ADN), methylglutaronitrie (MGN) and ethylsuccinonitrile (ESN).

The effluent from a reaction zone for converting 3PN and HCN into adiponitrile (ADN) includes a liquid, i.e. ADN, which is partially Immiscible with a hydrocarbon extraction solvent. Accordingly, the feed to the liquid/liquid extraction zone may include the effluent from a reaction zone for converting 3PN and HCN into adiponitrile (ADN) and a hydrocarbon extraction solvent feed without the need for an additional third feed of a liquid, which is partially Immiscible with a hydrocarbon extraction solvent.

Whether a dinitrile, such as ADN, is introduced into the liquid/liquid extraction zone as a separate feed or part of an effluent stream from a reaction zone, it is important to balance the mononitrile to dinitrile ratio, e.g., the 3PN to ADN ratio, in the liquid/liquid extraction zone. If this ratio is too high, sufficient separation of the feeds into 2 separate phases may not take place. If this ratio is too low, catalyst may tend to precipitate.

The extraction solvent phase or the light phase from the liquid/liquid extraction zone comprises extraction solvent, catalyst and at least a portion of the mononitriles, e.g., 3PN, fed to the liquid/liquid extraction zone. This extraction solvent phase may be distilled to recover extraction solvent to be recycled to the liquid/liquid extraction zone. A concentrated catalyst solution may also be recovered from the distillation zone and recycled to one or more reaction zones to which catalyst is fed.

The bottoms section of the distillation zone, used to distill the extraction solvent phase, comprises catalyst and 3PN. The conditions in this bottom section may be sufficient to cause 3PN to be isomerized to 2M3BN.

By controlling the 2PN/3PN ratio in distillation column bottoms, unwanted isomerization of 3PN to 2M3BN may be at least partially avoided. Distillation zones, where this unwanted isomerization may take place, include distillation zones which produce a concentrated catalyst solution from the effluent of a reaction zone and distillation zones which produce a concentrated catalyst solution by distillation of an extraction solvent phase from a liquid/liquid extraction zone.

Examples of distillation zones, which produce column bottoms comprising concentrated catalyst and 3PN, may be described with reference to FIG. 1.

FIG. 1 is a schematic representation of aspects of a process for making pentenenitriles by the hydrocyanation of 1,3-butadiene. Hydrogen cyanide is fed to hydrocyanation reaction zone 4 through line 1. Hydrocyanation reaction zone 4 may comprise one or more reactors. 1,3-Butadiene is fed to hydrocyanation reaction zone 4 through line 2. A solution comprising a hydrocyanation catalyst is introduced into hydrocyanation reaction zone 4 through line 3.

The effluent from hydrocyanation reactor 4 exits this reactor 4 through line 5. This effluent comprises unreacted 1,3-butadiene, catalyst solution, 3-pentenenitrile, 2-methyl-3-butenenitrile, and possibly some unreacted hydrogen cyanide. This effluent passes from hydrocyanation reaction zone 4 through line 5 to separation section 6.

In separation section 6, the effluent from the hydrocyanation reaction zone 4 is separated into streams 7, 8 and 10. Stream 7 comprises unreacted 1,3-butadiene, which, as shown in FIG. 1, is recycled to hydrocyanation reaction zone 4. A stream, which is concentrated in catalyst, is removed from separation section 6 by line 8. Separation section 6 may comprise one or more distillation zones, where catalyst and 3PN are present in the column bottoms. Unwanted isomerization of 3PN to 2M3BN may be minimized by controlling the 3PN/2PN ratio in these column bottoms.

A portion of the stream in line 8 may be removed through line 9 as a catalyst purge stream. This catalyst purge stream may be subjected to catalyst purification steps. These catalyst purification steps may involve extracting catalyst into an extraction solvent in a liquid/liquid extraction process, followed by distilling extraction solvent from the catalyst. This distillation of extraction solvent may result column bottoms comprising concentrated catalyst in the presence of 3PN. Unwanted isomerization of 3PN to 2M3BN may be minimized by controlling the 3PN/2PN ratio in these column bottoms.

The portion of the concentrated catalyst stream in line 8, which is not purged through line 9, may be recycled to hydrocyanation reaction zone 4. In FIG. 1, this recycle is illustrated by passing concentrated catalyst in stream 8 into catalyst solution feed stream in line 3. However, it will be understood that this recycle catalyst may occur in other ways. For example, concentrated catalyst in line 8 may be fed directly into at least one reactor in hydrocyanation reaction zone 4.

The stream in line 10 is concentrated with the 3-pentenenitrile and 2-methyl-3-butenenitrile products produced in hydrocyanation reaction zone 4. This stream in line 10 passes into separation section 11 to be separated into a stream concentrated in 2-methyl-3-butenenitrile and a stream concentrated in 3-pentenenitrile. The stream concentrated in 2-methyl-3-butenenitrile exits separation section 11 through line 12. The stream concentrated in 3-pentenenitrile exits separation section 11 through line 13.

The separation which takes place in separation section 6 may take place in one or more distillation columns.

Figure 2:
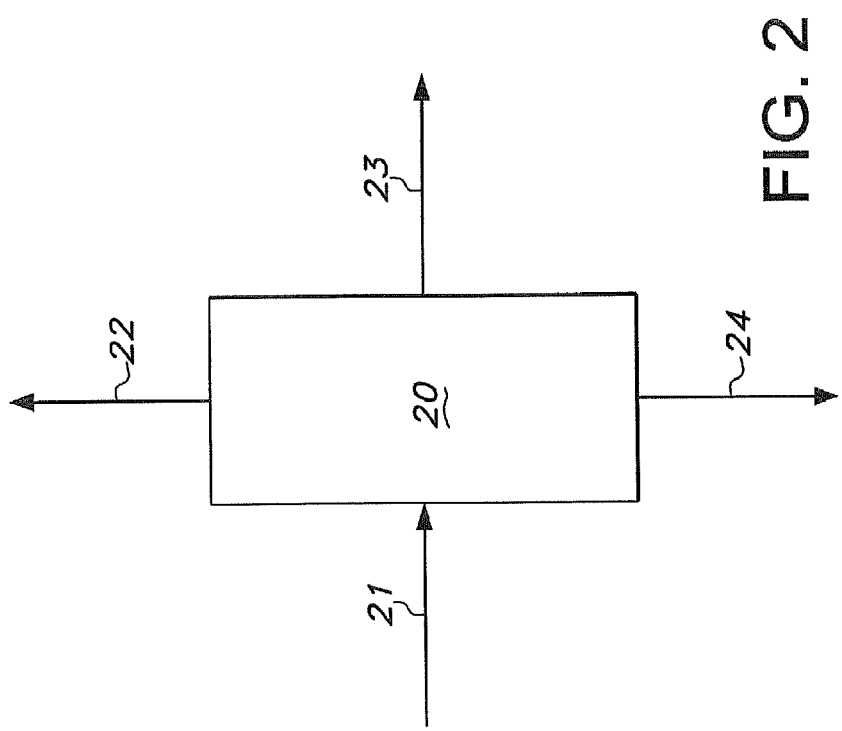
FIG. 2 illustrates separation of solvents from catalyst in the effluent from the hydroyanation of 1,3-butadiene in a single distillation column.

FIG. 2 illustrates an example of the separation, which takes place in separation section 6, as occurring in a single distillation column. In FIG. 2, effluent from hydrocyanation reaction zone 4 in FIG. 1, is introduced into distillation column 20 through line 21. Line 5 of FIG. 1 corresponds to line 21 of FIG. 2. A stream comprising unreacted 1,3-butadiene is taken as an overhead stream from distillation column 20 through line 22. Line 7 of FIG. 1 corresponds to line 22 of FIG. 2. A stream concentrated in 2-methyl-3-butenenitrile and 3-pentenenitrile is taken as a side stream from distillation column 20 through line 23. Line 10 of FIG. 1 corresponds to line 23 of FIG. 2. A stream concentrated in catalyst is taken as a bottom stream from distillation column 20 through line 24. Line 8 of FIG. 1 corresponds to line 24 of FIG. 2.

A concentrated catalyst solution comprising 3PN is present in the column bottoms of column 20. Unwanted isomerization of 3PN to 2M3BN may be minimized by controlling the 3PN/2PN ratio in these column bottoms.

Figure 3:
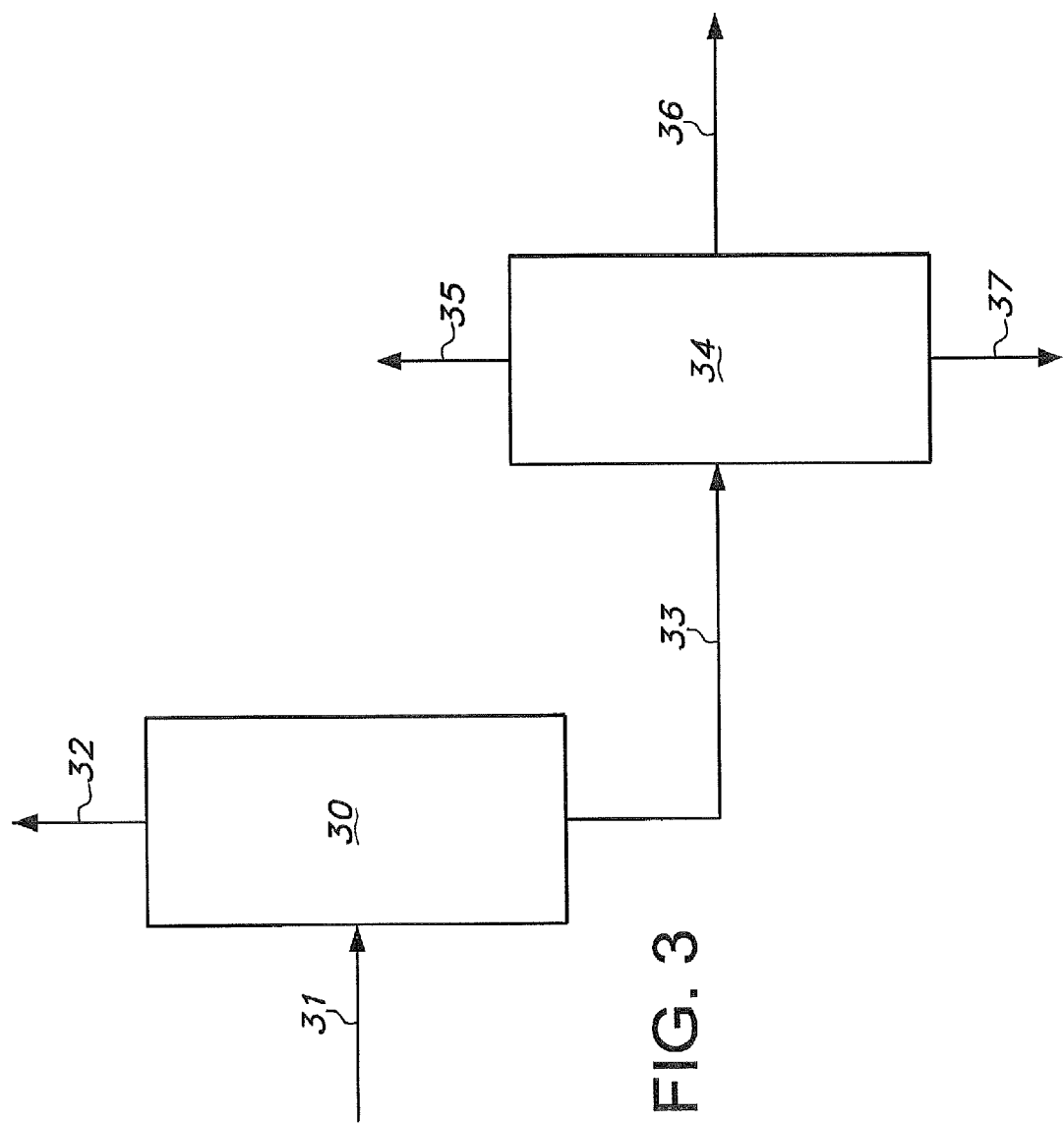
FIG. 3 Illustrates separation of solvents from catalyst in the effluent from the hydrocyanation of 1,3-butadiene in two distillation columns.

FIG. 3 Illustrates an example of the separation, which takes place in separation section 6, as occurring in two distillation columns. In FIG. 3, effluent from a hydrocyanation reaction zone 4 in FIG. 1, is Introduced into distillation column 30 through line 31. Line 5 of FIG. 1 corresponds to line 31 of FIG. 3. A stream comprising unreacted 1,3-butadiene is taken as an overhead stream from distillation column 30 through line 32. A portion of the unreacted 1,3-butadiene is also taken from distillation column 30 in a bottom stream through line 33. The bottom stream in line 33 further comprises 2-methyl-3-butenenitrile, 3-pentenenitrile and catalyst. Unwanted isomerization of 3PN to 2M3BN may be minimized by controlling the 3PN/2PN ratio in the column bottoms of column 30.

The bottoms stream from the first distillation column 30 is introduced into a second distillation column 34 through line 33. A stream comprising unreacted 1,3-butadiene is taken as an overhead stream from distillation column 34 through line 35. The combined streams from lines 32 and 35 may be introduced into the hydrocyanation reaction zone 4 of FIG. 1 as a recycle feed of unreacted 1,3-butadiene. A stream concentrated in 2-methyl-3-butenenitrile and 3-pentenenitrile is taken as a side stream from distillation column 34 through line 36. Line 10 of FIG. 1 corresponds to line 36 of FIG. 3. A stream concentrated in catalyst is taken as a bottom stream from distillation column 34 through line 37. Line 8 of FIG. 1 corresponds to line 37 of FIG. 3.

The column bottoms in column 34 comprise catalyst and 3PN. Unwanted isomerization of 3PN to 2M3BN may be minimized by controlling the 3PN/2PN ratio in these column bottoms.

The stream comprising 3PN and 2M3BN in line 36 may be distilled in an apparatus not shown in FIG. 3 to separate 3PN from 2M3BN. The 3PN may be passed to a hydrocyanation reactor for reacting 3PN with HCN to make adiponitrile. The 2M3BN may be passed to an isomerization reactor to convert 2M3BN into 3PN.

Figure 4:
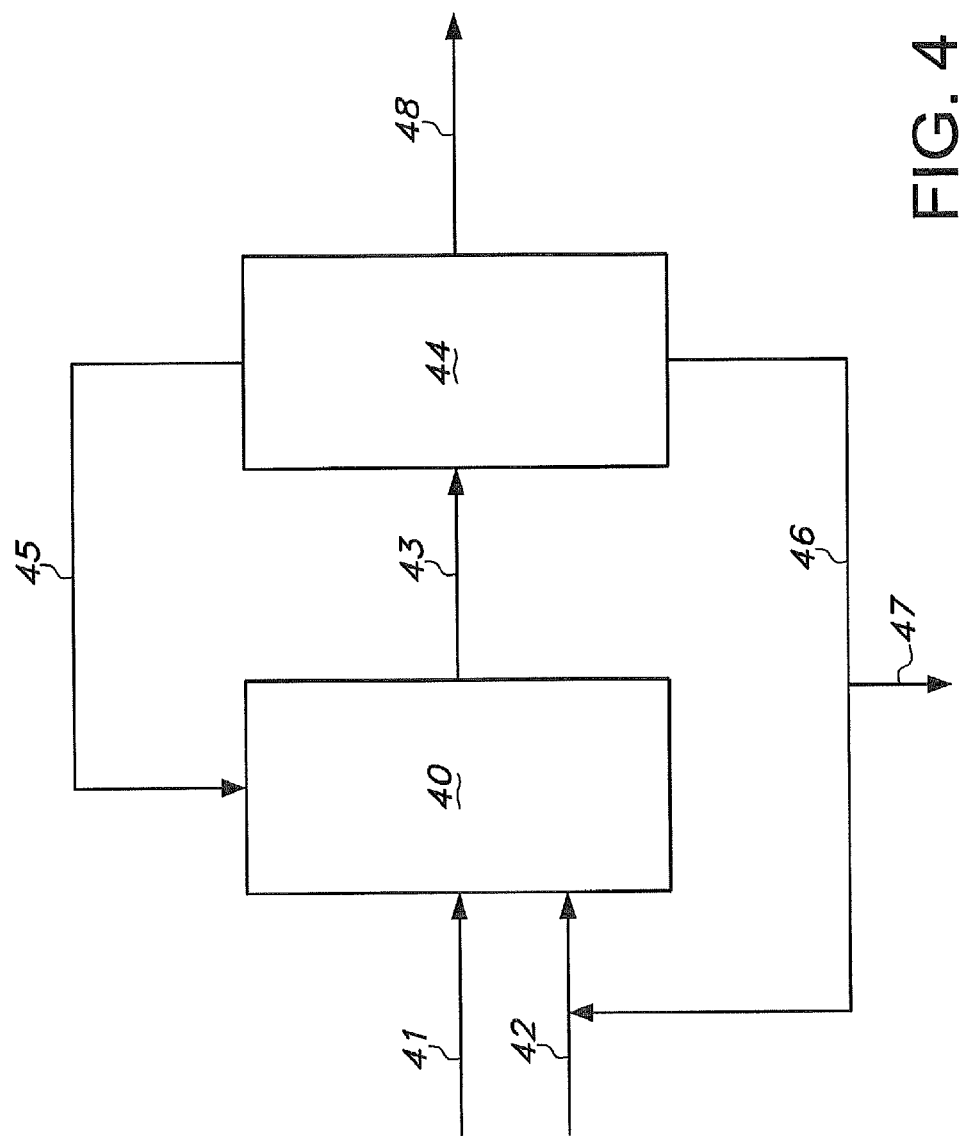
FIG. 4 is a schematic representation of aspects of a process for making 3-pentenenitrile by isomerizing 2-methyl-3-butenenitrile.

FIG. 4 is a schematic representation of aspects of a process for making 3-pentenenitrile by isomerizing 2-methyl-3-butenenitrile. A stream comprising 2-methyl-3-butenenitrile is fed to isomerization reaction zone 40 through line 41. Isomerization reaction zone 40 may comprise one or more reactors. A catalyst in the form of a stream of a dissolved catalyst is introduced into isomerization reaction zone 40 through line 42.

The effluent from isomerization reaction zone 40 exits this reactor through line 43. This effluent comprises 3-pentenenitrile product, unreacted 2-methyl-3-butenenitrile and dissolved catalyst. This effluent passes from isomerization reaction zone 40 to separation section 44 through line 43.

In separation section 44, the effluent from isomerization reactor 40 is separated into streams 45, 46, and 48. Stream 45 comprises unreacted 2-methyl-3-butenenitrile, which, as shown in FIG. 4, is recycled to isomerization reactor 40. A stream, which is concentrated in catalyst, is removed from separation section 44 by line 46. Separation section 44 may comprise one or more distillation zones, where catalyst and 3PN are present in the column bottoms. Unwanted isomerization of 3PN to 2M3BN may be minimized by controlling the 3PN/2PN ratio in these column bottoms.

A portion of the stream in line 46 may be removed through line 47 as a catalyst purge stream. This catalyst purge stream may be subjected to one or more catalyst purification steps. These catalyst purification steps may involve extracting catalyst into an extraction solvent in a liquid/liquid extraction process, followed by distilling extraction solvent from the catalyst. This distillation of extraction solvent may result column bottoms comprising concentrated catalyst in the presence of 3PN. Unwanted isomerization of 3PN to 2M3BN may be minimized by controlling the 3PN/2PN ratio in these column bottoms.

The portion of the concentrated catalyst stream, which is not purged through line 47, may be recycled to isomerization reactor 40. In FIG. 4, this recycle is illustrated by passing concentrated catalyst in stream 46 into catalyst solution feed stream in line 42. However, it will be understood that this recycle of catalyst may occur in other manners. For example, concentrated catalyst in line 46 may be fed directly into isomerization reaction zone 40.

The product stream in line 48 may be passed to a hydrocyanation reaction zone for producing adiponitrile by reacting 3-pentenenitrile with hydrogen cyanide.

The separation which takes place in separation section 44 may occur in one or more distillation columns. Although FIG. 2 was previously referred to herein in the context of representing a distillation column for use in separation section 6 of FIG. 1, FIG. 2 may also be used to represent a distillation column for use as separation section 44 of FIG. 4. In particular, line 21 of FIG. 2 may be viewed as representing the isomerization product feed stream in line 43 of FIG. 4. Distillation column 20 of FIG. 2 may also be viewed as a distillation column for producing a stream concentrated in 2-methyl-3-butenenitrile as an overhead stream in line 22, a side stream concentrated in 3-pentenenitrile in line 23, and a bottom stream concentrated in catalyst and line 24. The column bottoms in column 20 comprise catalyst and 3PN. Unwanted isomerization of 3PN to 2M3BN may be minimized by controlling the 3PN/2PN ratio in these column bottoms.

Figure 5:
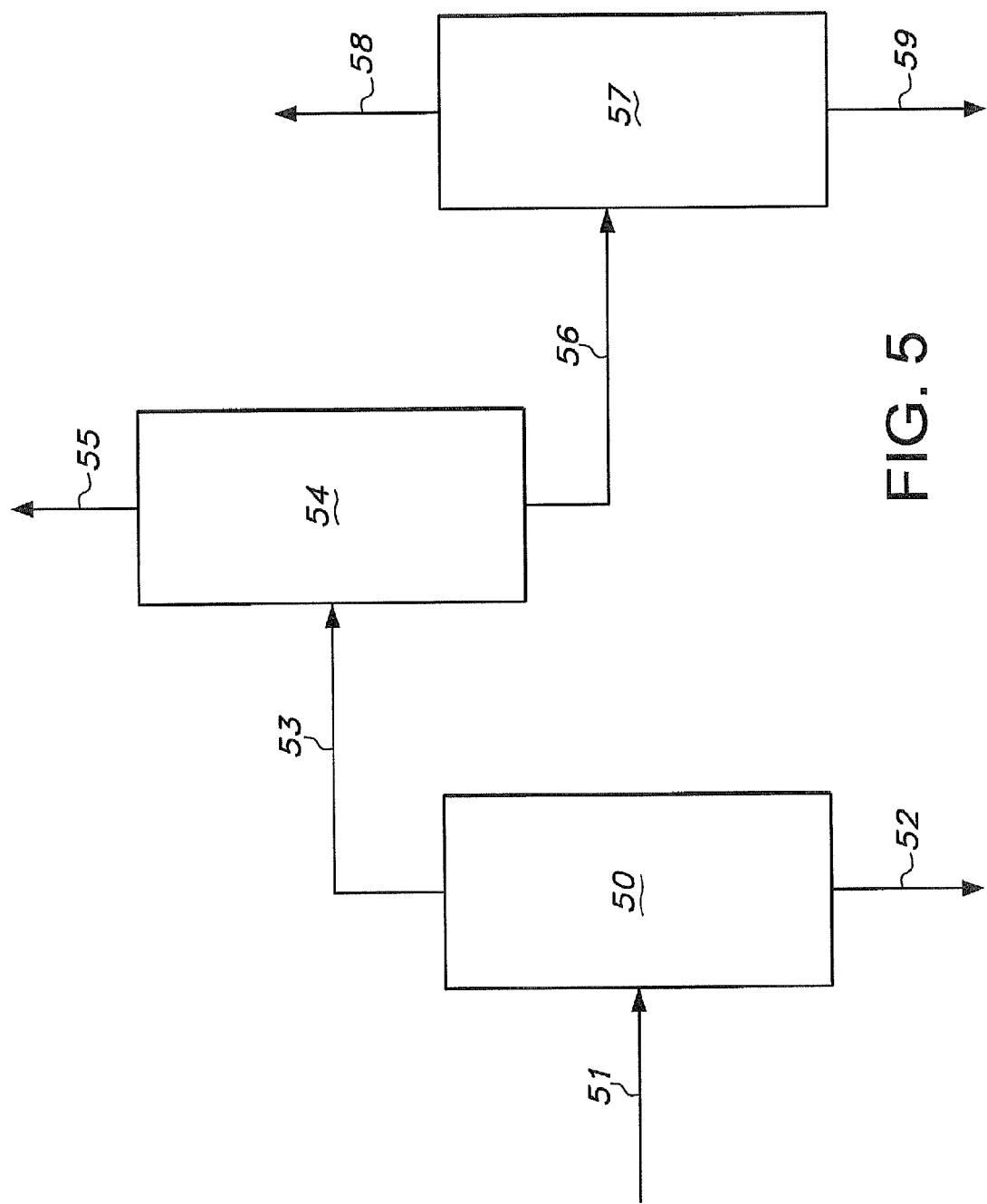
FIG. 5 illustrates separation of components from an effluent from a reaction zone, wherein 2-methyl-3-butenenitrile is isomerized to 3-pentenenitrile.

FIG. 5 is a schematic representation of an example of a distillation train, which may be used as separation section 44, shown in FIG. 4. Line 43 of FIG. 4 corresponds to line 51 of FIG. 5. The isomerization reaction effluent in stream 51 obtained in the isomerization reaction zone is distilled to recover catalyst and products. In a distillation step not shown in FIG. 5, low boilers may first be removed from stream 51. Low boilers are compounds which boil at temperatures less than pentenenitriles. Examples of light boilers include, butane, butadiene and cyclohexane.

The low boilers may be removed from the reactor effluent in line 51 in a distillation column not shown in FIG. 5. Column bottoms in such a distillation column comprise catalyst and 3PN. Unwanted isomerization of 3PN to 2M3BN may be minimized by controlling the 3PN/2PN ratio in these column bottoms.

Compounds in stream 51, including compounds which boil at the same temperature or higher than pentenenitrile, are introduced into distillation apparatus 50. Distillation apparatus 50 may comprise one or more distillation columns. A pentenenitrile-enriched stream 53, comprising 3PN, 2M3BN, and (Z)-2M2BN, may be obtained from the distillation apparatus 50. Stream 53 may also comprise other pentenenitriles, such as 2PN, 4PN, (E)-2M2BN, or a combination thereof, and optionally dimerized BD compounds having the empirical formula $C_8H_{12}$, such as VCH and ethylidene cyclohexene isomers. A pentenenitrile-depleted stream 52, enriched in at least one catalyst, may be obtained as the bottom product. Column bottoms in distillation apparatus 50 comprise catalyst and 3PN. Unwanted isomerization of 3PN to 2M3BN may be minimized by controlling the 3PN/2PN ratio in these column bottoms.

U.S. Pat. No. 3,852,329 describes a process for "reduced loss to undesirable products such as 2-methyl-2-butenenitrile." An objective of the distillation of stream 53 is to purge at least a portion of the lower-boiling (Z)-2M2BN isomer from the 3PN and 2M3BN reaction product mixture.

Stream 53, comprising 3PN, 2M3BN, and (Z)-2M2BN, is distilled in distillation apparatus 54. Stream 55 is obtained as an overhead product that is enriched in (Z)-2M2BN. Stream 56, comprising 3PN and 2M3BN, is obtained as a bottom product and is depleted in (Z)-2M2BN. "Enriched" and "depleted" in (Z)-2M2BN are relative to its concentration in stream 53.

Stream 55 may also comprise other pentenenitriles, selected from the group comprising 2M3BN, (E)-2M2BN, and optionally dimerized BD compounds having the empirical formula $C_8H_{12}$, such as VCH and ethylidene cyclohexene isomers. Stream 56 may also comprise other pentenenitriles, selected from the group comprising 4PN, 2PN, and (E)-2M2BN.

In one embodiment, the distillation is operated in such a manner to cause dimerized butadiene (BD) compounds to be enriched in stream 55 and depleted in stream 56, both relative to the concentration of dimerized BD compounds in stream 53.

In another embodiment, dimerized BD compounds are enriched in stream 55 through an azeotrope of said compounds with 2M3BN. In another embodiment, stream 55 comprises greater than 1% by weight, for example greater than 5% by weight, for example greater than 10% by weight of 2M3BN, relative to the total mass of stream 55.

Stream 56, comprising 3PN and 2M3BN, may be transferred at least in part to distillation apparatus 57. In this apparatus, the distillation of stream 56 occurs to obtain a 2M3BN-enriched stream 58 and a 2M3BN-depleted stream 59 comprising 3PN. As described in the "Nylon Intermediates Refining" section of the PhD thesis dissertation by Decio Heringer Coutinho, University of Texas at Dallas, December 2001, stream 58 may be obtained at the top region of the distillation apparatus 57, while the stream 59 may be obtained at the bottom region of the distillation apparatus 57.

FIG. 5 illustrates one distillation system for distilling the effluent from the isomerization reaction zone. However, it will be understood that it is within the skill in the art to design and operate other distillation systems to achieve the same or essentially the same results. For example, a distillation step to remove low boilers may be inserted into the system, as described above. It is also possible to share equipment used for distilling the effluent from the hydrocyanation reaction zone for making 3PN. For example, a stream comprising 3PN and 2M3BN obtained by distilling the effluent from the hydrocyanation reaction zone 4 may be passed to the same distillation apparatus used in the distillation of the stream in line 36 of FIG. 3.

Figure 6:
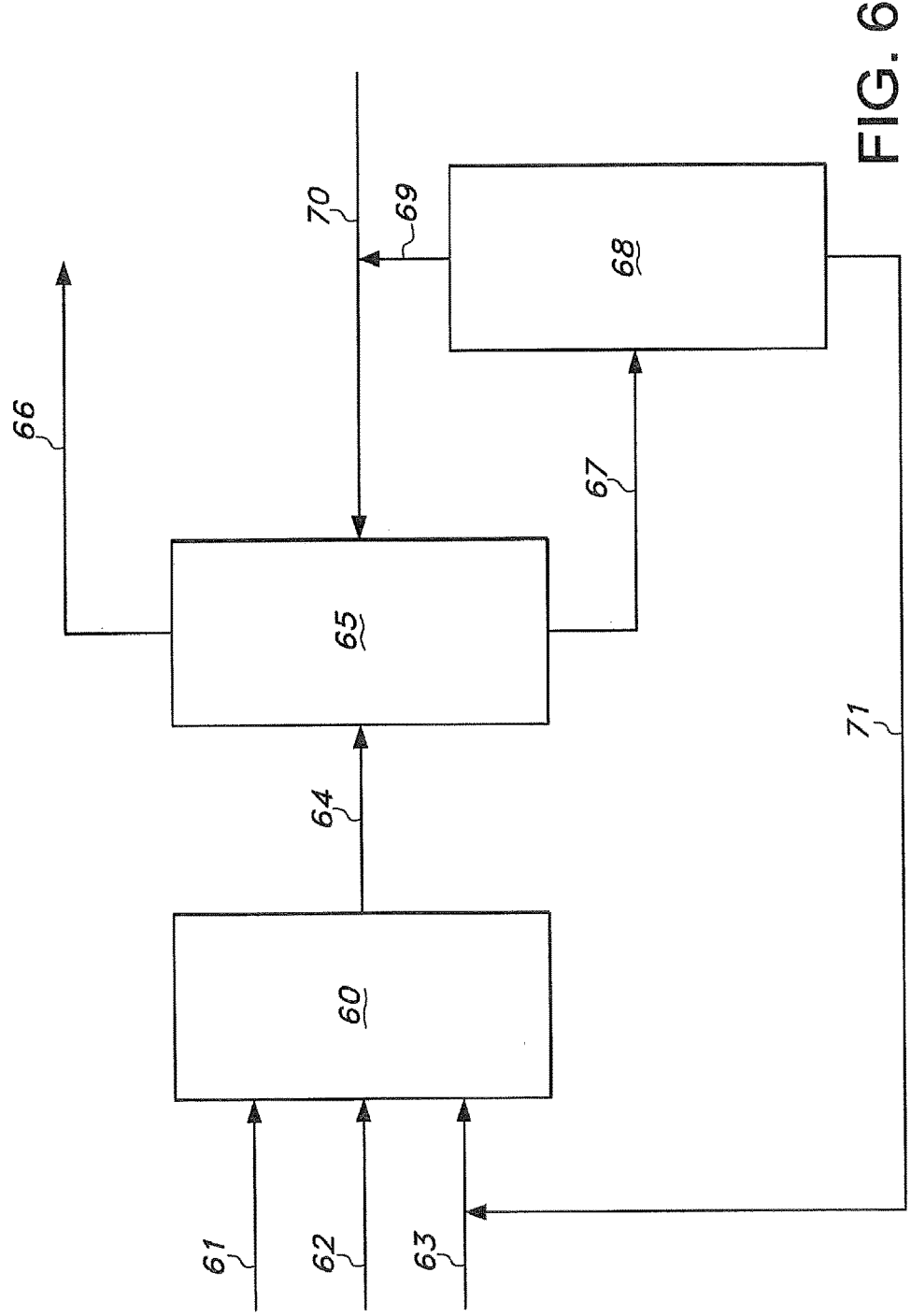
FIG. 6 is a schematic representation of aspects of a process for making adiponitrile by the hydrocyanation of 3-pentenenitrile.

FIG. 6 is a schematic representation of aspects of a process for making adiponitrile by the hydrocyanation of 3-pentenenitrile. Hydrogen cyanide is fed to hydrocyanation reaction zone 60 through line 61. Hydrocyanation reaction zone 60 may comprise one or more reactors. 3-Pentenenitrile is fed to hydrocyanation reaction zone 60 through line 62. A solution comprising a hydrocyanation catalyst is introduced into hydrocyanation reaction zone 60 through line 63.

The effluent from hydrocyanation reaction zone 60 exits this zone 60 through line 64. This effluent comprises unreacted 3-pentenenitrile, catalyst solution, and adiponitrile product. This effluent passes from hydrocyanation reaction zone 60 through line 64 to extraction section 65.

In addition to the reaction effluent stream in line 64, an extraction solvent stream is introduced into extraction section 65 through line 70. In the extraction section 65, the contents separate into two liquid phases. A light phase comprises extraction solvent and catalyst. A heavy phase or raffinate phase comprises 3-pentenenitrile, adiponitrile and catalyst degradation products. The heavy phase exits extraction section 65 through line 66. The light phase exits extraction section 65 through line 67. The light phase in line 67 enters distillation section 68. The overhead stream from distillation section 68 is concentrated in extraction solvent. In FIG. 6, this stream exits distillation section 68 through line 69 and is introduced into line 70 to provide recycled extraction solvent. Although not shown in FIG. 6, at least a portion of recycled extraction solvent may be passed directly into extraction section 65 instead of into line 70.

Column bottoms in distillation section 68 comprise catalyst and 3PN. Unwanted isomerization of 3PN to 2M3BN may be minimized by controlling the 3PN/2PN ratio in these column bottoms.

The catalyst enriched stream in line 71 may be introduced into line 63 as a catalyst recycle stream. However, at least a portion of the stream in line 71 may also be passed directly into the hydrocyanation reaction zone 60 without first passing into line 63.

The raffinate phase removed from extraction section 65 through line 66 may comprise residual extraction solvent. At least a portion of this residual extraction solvent may be removed in a separate distillation section downstream from line 66. This separate distillation section is not shown in FIG. 6.

Figure 7:
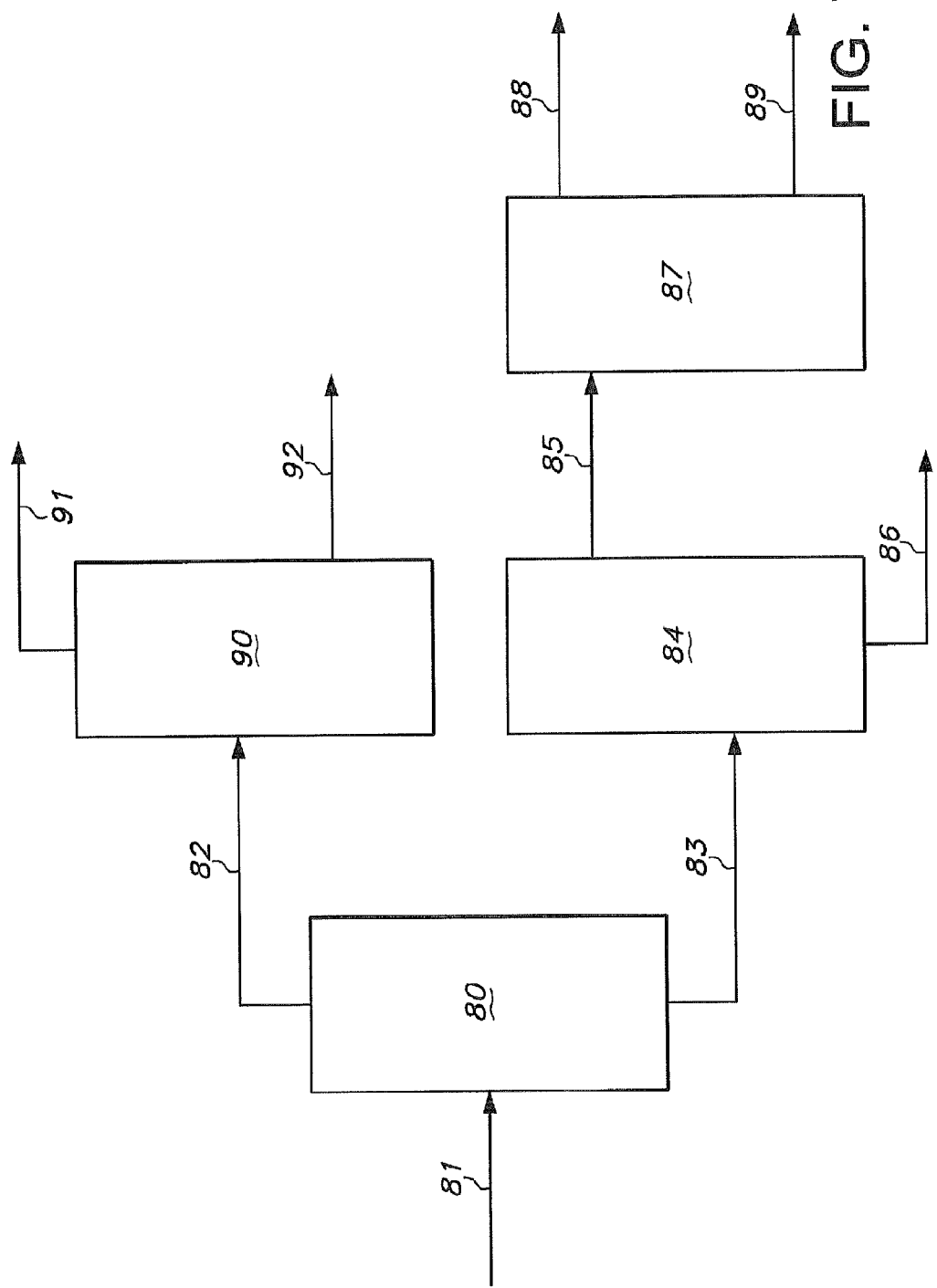
FIG. 7 illustrates a series of distillation steps which may be used to further process a raffinate stream obtained from a liquid/liquid extraction process.

FIG. 7 Illustrates a series of distillation steps which may be used to further process the raffinate stream in line 66 of FIG. 6, preferably after residual extraction solvent has been essentially removed from the raffinate stream. This treated raffinate stream is passed to distillation section 80 through line 81. This treated raffinate stream in line 81 may comprise, adiponitrile, catalyst degradation products, methylglutaronitrile, 3-pentenenitrile, 4-pentenenitrile, 2-methyl-3-butenenitrile, trans-2-pentenenitrile, cis-2-pentenenitrile, and 2-methyl-2-butenenitrile. In FIG. 7, an overhead stream is removed from distillation section 80 through line 82, and a bottoms stream is removed from distillation section 80 through line 83. The overhead stream in line 82 may comprise 3-pentenenitrile, 4-pentenenitrile, 2-methyl-3-butenenitrile, trans-2-pentenenitrile, cis-2-pentenenitrile, and 2-methyl-2-butenenitrile. The bottoms stream in line 83 may comprise adiponitrile, catalyst degradation products and methylglutaronitrile.

The bottoms stream in line 83 passes into distillation section 84 to provide an overhead stream 85 and a bottoms stream 86. The overhead stream 85 may comprise adiponitrile and methylglutaronitrile. The bottoms stream 86 may comprise catalyst degradation products.

The overhead stream from distillation section 84 passes through line 85 to distillation section 87. An overhead stream comprising methylglutaronitrile is removed through line 88 and a bottoms stream comprising adiponitrile is removed through line 89.

The overhead stream from distillation section 80 is introduced into distillation section 90 through line 82. An overhead stream comprising cis-2-pentenenitrile, and 2-methyl-2-butenenitrile (i.e. cis-2-methyl-2-butenenitrile and trans-2-methyl-2-butenenitrile) is removed from distillation section 90 through line 91, and a bottoms stream comprising 3-pentenenitrile, 4-pentenenitrile, trans-2-pentenenitrile, and a portion of E-2-methyl-2-butenenitrile is removed through line 92.

The same catalyst may be used in all three reaction zones which are illustrated in the drawings as first hydrocyanation zone 4 to make 3PN, isomerization reaction zone 40, and second hydrocyanation zone 60 to make adiponitrile. Using the same catalyst in all three reaction zones may lower capital and operating costs. However, the transfer or sharing of a single catalyst among all three reaction zones has disadvantages in that such a process may be performance limited by a single catalyst in any one or all three reaction zones. The physical properties of the single catalyst during required separation steps may also create disadvantages. For example, reboiler temperatures at certain points in the product separation train may degrade less thermally stable catalysts. By means of selecting catalysts for the individual reaction zones and limiting the transfer of catalyst between reaction zones and/or stages, higher 3PN and ADN product quality and chemical yields from BD and HC≡N may be achieved.

Selecting catalysts for individual reaction steps and limiting the transfer of catalyst between reaction steps facilitates control of reaction byproduct formation. Such byproducts include at least: 4-vinyl-1-cyclohexene, 2-methyl-2-butenenitrile, and mononitrile compounds of the chemical formula $C_8H_{13}C\equiv N$. As disclosed herein, separately treating the catalyst components and not co-mingling them among process stages provides opportunities to manage the flow of reaction byproducts, once formed, from one process step into another process step. For example, transfer of reaction byproducts in catalyst streams from a first process stage to produce 3PN by hydrocyanation or isomerization into the second process stage to produce ADN and vice versa, may be controlled.

In an overall process for making adiponitrile starting with 1,3-butadiene, a wide variety of compounds with various boiling points is produced. When 1,3-butenenitrile is reacted with hydrogen cyanide, both 3-pentenenitrile and 2-methyl-3-butenenitrile are produced. 2-methyl-3-butenenitrile has a listed boiling point of 125° C., cis-2-pentenenitrile has a listed boiling point of 127-128° C., and trans-3-pentenenitrile has a listed boiling point of 144-147° C. In an integrated process for making adiponitrile, 3-pentenenitrile is reacted with hydrogen cyanide to produce adiponitrile. Adiponitrile has a listed boiling point of 295° C.

When 3-pentenenitrile and adiponitrile are produced, reaction byproducts and catalyst degradation byproducts may also be produced. Unreacted reactants may also become entrained in the effluent from reaction zones used to produce pentenenitriles and adiponitrile.

Certain compounds in effluents from reaction zones are referred to herein as low, intermediate or high boilers.

As used herein, the term "low boilers" refers to compounds having a lower boiling point than the listed boiling point of 2-methyl-3-butenenitrile, i.e. 125° C. Examples of such low boilers include 1-butene, 1,3 butadiene, trans-2-butene, hydrogen cyanide, and cyclohexane. 1-butene has a listed boiling point of −6.3° C. 1,3-butadiene has a listed boiling point of −4.5° C. Trans-2-butadiene has a listed boiling point of 1° C. Hydrogen cyanide has a listed boiling point of 25.7° C. Cyclohexane has a listed boiling point of 80.7° C. (Z)-2M2BN has a listed boiling point of 121.6° C.

Compounds having a boiling point between 147° C. and 295° C. are referred to herein as intermediate boilers. The listed boiling point for 3-pentenenitrile may be as high as 147° C. 295° C. is the listed boiling point for adiponitrile. Examples of compounds which are intermediate boilers include $C_9$ mononitriles, phenol, cresols, TBC, MGN and ESN. $C_9$ mononitriles encompass a broad range of compounds having boiling points between 147 and 295° C. Phenol and cresols have listed boiling points of between 180 and 210° C. Tertiary-butylcatachol (TBC) has a listed boiling point of 285° C. Methylglutaronitrile, especially 2-methylglutaronitrile (MGN), has a listed boiling point of 269-271° C. 2-Ethylsuccinonitrile (ESN) has a listed boiling point of 264° C.

High boilers have a listed boiling point above that of adiponitrile, i.e. 295° C. Examples of high boilers include tri-tolyl-phosphite (TTP), or modified tri-tolyl-phosphite (MTTP), phosphorus containing ligand degradation products, $Ni(CN)_2$, $ZnCl_2$ and triphenylboron. In tri-tolyl-phosphite (TTP), three tolyl groups are bound to a phosphite group. In modified tri-tolyl-phosphite (MTTP), at least one of these tolyl groups is replaced with a phenyl group. Examples of MTTP include phenyl-di-tolyl-phosphite, toly-di-phenyl-phosphite and mixtures of these compounds.

Effluents from reaction zones for making 3PN and adiponitrile include low boilers, Intermediate boilers and high boilers. Desired products, such as 3-pentenenitrile and adiponitrile, need to be purified, in that solutions of these desired products need to be separated from Impurities, which are low boilers, intermediate boilers and high boilers. Catalyst, which is to be recycled, also needs to be purified or regenerated by removing certain reaction byproducts and catalyst degradation byproducts from streams including solutions of catalyst.

Reaction byproducts produced in the first hydrocyanation reaction zone to make 3PN include $C_8H_{13}C\equiv N$ compounds. These $C_8H_{13}C\equiv N$ compounds may be produced by dimerization of 1,3-butadiene and hydrocyanation of such dimers. $C_8H_{13}C\equiv N$ compounds may be separated from catalyst in the extraction zone used to purify the catalyst from the first hydrocyanation reaction zone to make 3PN or the isomerization reaction zone or both the first hydrocyanation reaction zone and the isomerization reaction zone. $C_8H_{13}C≡N$ compounds generally have boiling points within the range of 150° C. to 295° C.

The reaction product from the first hydrocyanation reaction zone to make 3PN may comprise one or more phenolic compounds of the formula

(I)

where $R^1$ is H or an alkyl group having 1 to 4 carbon atoms, and n is 0 to 4, provided that when the phenolic compound of formula (I) has more than one alkyl group, these alkyl groups may be the same or different. Examples of such phenolic compounds include phenol and cresols. In particular, cresols are reacted with phosphorus trichloride ($PCl_3$) to make tri-tolyl-phosphite (TTP) ligands, and both phenol and cresols are reacted with phosphorus trichloride ($PCl_3$) to make modified tri-tolyl-phosphite (MTTP) ligands. In MTTP, at least one of the tolyl groups in TTP is replaced with a phenyl group. Consequently, cresols may be present as impurities when the first phosphorus-containing ligand is TTP, and both phenol and cresols may be present as impurities when the first phosphorus-containing ligand is MTTP. Cresols may also be produced in the first hydrocyanation reaction zone to make 3PN or at another point upstream of the extraction zone by unwanted hydrolysis of TTP ligands. Furthermore, both phenol and cresols may also be produced in the first hydrocyanation reaction zone to make 3PN or at another point upstream of the extraction zone by unwanted hydrolysis of MTTP ligands. The phenol and cresol Impurities have an approximate boiling point falling within the range of 180° C. to 210° C. By limiting the amount of phenolic compounds of formula (I) entering into the second hydrocyanation reaction zone to make adiponitrile, degradation of the catalyst, particularly a catalyst comprising a bidentate phosphorus-containing ligand, may be reduced.

In distillation steps upstream of the extraction zone, compounds such as 3PN and 2M3BN, having boiling points less than, for example, 150° C., are separated from a higher boiling, catalyst-containing stream. Since tertiary-butylcatechol, $C_8H_{13}C≡N$ compounds, phenol and cresols have boiling points higher than 150° C., they may pass along with catalyst in the distillation train upstream of the extraction zone. However, when tertiary-butylcatechol, $C_8H_{13}C≡N$ compounds, phenol and cresols are present, significant amounts of these compounds are taken up in the raffinate phase of the extraction zone. $C_8H_{13}C≡N$ compounds, phenol and cresols in the raffinate phase may be separated from dinitriles in the distillation train used to produce a dinitrile recycle stream to be passed into the extraction zone.

Buildup of catalyst degradation products and reaction byproducts may be reduced by a particular way of purifying a catalyst used for making 3PN or adiponitrile. The catalyst may be purified in a liquid/liquid extraction treatment. The same or different extraction zone may be used to purify the catalysts used in the three reaction zones to make 3PN and adiponitrile.

During the course of the reaction in the first hydrocyanation reaction zone for making 3PN, as well as in subsequent processing of the reactor effluent, for example, during distillation, a portion of the first catalyst may degraded or lost. There is a need to replenish catalyst which is degraded or lost. Catalyst which has been lost by degradation is replenished after the extraction treatment. Make-up catalyst may be added to a catalyst recycle stream after the catalyst passes through an extraction zone. However, it will be understood that catalyst, which passes through an extraction zone, may be provided with make-up catalyst and reintroduced into a reaction zone in different locations.

Reaction byproducts produced during the reaction of 1,3-butadiene and HCN in a first hydrocyanation reaction zone to make 3PN include $C_8H_{13}C≡N$ compounds. These $C_8H_{13}CN$ compounds may be produced by dimerization of 1,3-butadiene and hydrocyanation of such dimers. When such $C_8H_{13}CN$ compounds are introduced into a reaction zone for producing adiponitrile by the reaction of 3PN with HCN, these $C_8H_{13}C≡N$ compounds may react with HCN to produce unwanted $C_8H_{14}(C≡N)_2$ compounds. $C_8H_{13}C≡N$ compounds are separated from a first catalyst in a liquid/liquid extraction zone. Methods for removing these $C_8H_{13}C≡N$ compounds from 3PN and adiponitrile are discussed in International Publication Number WO 2012/005910.

The First Hydrocyanation Reaction Zone

As shown in FIG. 1, 1,3-butadiene (BD) containing feedstock may be fed to the first hydrocyanation reaction zone 4 for making 3PN, e.g., via line 2, a hydrogen cyanide feed may be fed to the first hydrocyanation reaction zone 4, e.g., via line 1, and a first catalyst may be fed to the first hydrocyanation reaction zone 4, e.g., via line 3.

The 1,3-butadiene feedstock may comprise at least 98 wt % 1,3-butadiene based on the total weight of the feedstock, preferably at least 99 wt %, and more preferably at least 99.5 wt %. In one embodiment, the feedstock comprises from 99.5 to 99.9 wt % 1,3-butadiene based on the total weight of the feedstock. The balance of the feedstock may comprise residual levels of undesirable impurities, such as butane, butenes, 1,2-butadiene and acetylenes such as propyne. The feedstock may also comprise tertiary-butylcatechol (TBC), for example, 4-tert-butylcatechol. At least 95% of the TBC may be present in the form of 4-tert-butylcatechol. A portion of TBC present in the feedstock may optionally be removed before charging the 1,3-butadiene to the first reaction step. The BD-containing feed may comprise less than a total of 100 ppm acetylenes.

The HC≡N feed to the first hydrocyanation reaction zone 4 for making 3PN and the second hydrocyanation reaction zone 60 for making adiponitrile may be a product of the Andrussow process that is dried to less than about 250 ppm water, for example, less than 125 ppm water, for example, less than 80 ppm water, by distillation prior to entry into olefin hydrocyanation reaction zones. However, the HCN feed will usually contain at least some water. Very dry HCN is unstable, and, for this reason, it may be undesirable to provide completely anhydrous HCN. Accordingly, the HCN feed may comprise at least 10 ppm, for example, at least 25 ppm, for example, at least 50 ppm, water.

The hydrogen cyanide (HC≡N) is preferably substantially free of carbon monoxide, oxygen and ammonia. This HC≡N can be introduced to the first hydrocyanation reaction zone 4 and the second hydrocyanation reaction zone 60 as a vapor, liquid, or mixtures thereof; see, for example, European Patent Publication No. 1 344 770. As an alternative, a cyanohydrin can be used as the source of HC≡N; see, for example, U.S. Pat. No. 3,655,723.

The HC≡N feed, the BD-containing feed, and the catalyst composition are contacted in a reaction zone, which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

A non-oxidizing and anhydrous environment retards oxidative deactivation of the catalyst. Accordingly, a dry inert atmosphere, e.g., nitrogen, is normally used in reaction zones, although air may be used at the expense of loss of a portion of the catalyst through oxidation and hydrolysis.

The 1,3-butadiene (BD) hydrocyanation is preferably conducted using BD substantially free of oxygen, acetylenes and water. BD can be introduced to the hydrocyanation reaction zone as a vapor, liquid, or mixtures thereof; see, for example, European Patent Publication No. 1 344 770. BD may be at least partially depleted of tertiary-butylcatechol prior to contacting the catalyst.

The BD hydrocyanation reaction temperature is typically maintained within the range of about −25° C. to about 200° C., for example, within the range of about 0° C. to about 150° C. Generally, the reaction pressure should be sufficient to maintain the BD and HC≡N in contact with the catalyst dissolved in the liquid reaction mixture, with such pressure at least, in part, being a function of the amount of unreacted BD present in the reaction mixture. Though the disclosed process is not limited by an upper limit of pressure for this reaction step, for practical purposes the pressure may generally range from about 15 psia to about 300 psia (about 1.03 bar to about 20.7 bar).

The overall feed molar ratio of the BD to HC≡N may be in the range of about 1:1 to about 100:1, for example, in the range of about 1:1 to about 2:1. Excess BD within the reaction zone may decrease the formation of dinitriles during the BD hydrocyanation reaction.

The feed molar ratio of HC≡N to catalyst in the reaction of HC≡N with BD may be in the range of about 5:1 to about 100,000:1, for example, in the range about 100:1 to about 5,000:1.

In an embodiment where the catalyst, which is fed to the first hydrocyanation reaction zone, comprises a monodentate ligand, the molar ratio of monodentate ligand to nickel in the catalyst for the reaction of HC≡N with BD may be from about 4:1 to about 50:1, for example, from about 4:1 to about 30:1, for example, from about 4:1 to about 15:1. When a bidentate ligand is used, the molar ratio of bidentate ligand to zero valent nickel in the catalyst for the isomerization reaction may be from 1:1 to 10:1, for example, from 1:1 to 5:1.

The residence time in the BD hydrocyanation reaction zone is typically determined by the desire to obtain a certain degree of conversion of BD, HC≡N, or a combination thereof. The BD hydrocyanation reaction zone may comprise one or more physical reactors. For example, the BD hydrocyanation zone may include a combination one or more plug flow reactors in combination with one or more continuous stirred tank reactors. When a reactor is used that substantially provides the mixing characteristics of a continuous stirred tank reactor, "residence time" is the time necessary for the combined feeds to displace one reactor volume for this reaction step.

In addition to residence time, catalyst concentration and reaction temperature will also affect conversion of reactants to products. Generally, residence times will be in the range of about 0.1 hour to about 15 hours, for example, in the range of about 1 hour to about 10 hours. The HC≡N conversion may be, for example, greater than 99%. Generally, BD conversion in the BD hydrocyanation reaction zone may be less than 99%, for example, between 80 and 95% overall, for example 90% overall. Staged HCN addition within the hydrocyanation reaction zone may be used.

The reaction product mixture from the BD hydrocyanation reaction zone, including BD, 3PN, 2M3BN, and catalyst, may be distilled in one or more distillation apparatus to recover a BD-enriched stream, pentenenitrile-enriched stream Including 3PN and 2M3BN, and catalyst-enriched stream including the catalyst. The BD-enriched and catalyst-enriched streams may be recycled to the BD hydrocyanation reaction. The pentenenitrile-enriched stream may be further distilled to obtain a 2M3BN-enriched stream and a 2M3BN-depleted stream including 3PN.

The 2M3BN-enriched stream from the BD hydrocyanation process may be a 2M3BN feed to the 2M3BN isomerization process. In FIG. 1, this 2M3BN-enriched stream is represented by stream 12. The 2M3BN-depleted stream including 3PN may be used as a 3PN feed to the second hydrocyanation reaction zone 60. A 2M3BN-depleted stream including 3PN is represented in FIG. 1 as stream 13.

As noted above, the reaction of 1,3-butadiene and hydrogen cyanide in the presence of a catalyst in a first hydrocyanation reaction zone 4 produces a first reaction effluent (stream 5) comprising 1,3-butadiene, 3-pentenenitrile, 2-methyl-3-butenenitrile, and first catalyst. These components of the reaction effluent may be separated, at least partially, by one or more distillation steps, represented, schematically, by separation section 6 In FIG. 1. In particular, these distillation steps may take place in one or more distillation columns, to provide:

1) at least one 1,3-butadiene-enriched stream 7;
2) a first 2-methyl-3-butenenitrile-enriched stream 12;
3) a first 3-pentenenitrile-enriched stream 13; and
4) a first catalyst-enriched stream 8.

These streams are enriched with a particular component in that they have greater concentrations of these components than the effluent from the first hydrocyanation reaction zone 4 In line 5. For example, the first catalyst-enriched stream 8 has a greater concentration of catalyst than the effluent stream in line 5. The first 2-methyl-3-butenenitrile-enriched stream 12 and first 3-pentenenitrile-enriched stream 13 may each contain less than a total of 500 parts per million by weight of phosphorus-containing ligand, for example, less than 350 parts per million by weight of phosphorus-containing ligand, for example, less than 200 parts per million by weight of phosphorus-containing ligand. If an excessive amount of dinitriles is present in the effluent of from the first hydrocyanation reaction zone 4, catalyst may thermally degrade, causing the nickel/ligand complex to disassociate in column bottoms of distillation apparatus used to obtain the first catalyst-enriched stream 8.

At least partial separation of a 3-pentenenitrile and 2-methyl-3-butenenitrile mixture from at least one phosphorus-containing ligand may be achieved by a distillation process. For example, this separation may be facilitated by a distillation apparatus comprising a feed inlet; an upper draw outlet; and a bottom draw outlet. A phosphorus-containing ligand stream, such as stream 33 of FIG. 3, which comprises 3PN, 2M3BN, and at least one catalyst including a phosphorus-containing ligand, may be flowed into a feed stage of a distillation apparatus through the feed inlet. The distillation apparatus may include a stripping section, a rectifying section or both. There may be at least one stage of separation between the feed inlet and the upper draw outlet. A pentenenitrile-enriched stream comprising 3-pentenenitrile and 2-methyl-3-butenenitrile may be withdrawn from the upper draw outlet. This stream is depleted of at least one phosphorus-containing ligand, relative to the phosphorus-containing ligand stream fed to the distillation column. A pentenenitrile-depleted stream may be withdrawn from the bottom draw outlet. This pentenenitrile-depleted stream is enriched with the phosphorus-containing ligand, relative to the phosphorus-containing ligand stream fed to the distillation column. The first distillation apparatus may be operated such that the pentenenitrile-depleted stream comprises at least 5% by weight of pentenenitrile including the sum of 3-pentenenitrile and 2-methyl-3-butenenitrile.

The pentenenitrile-enriched stream comprising 3-pentenenitrile and 2-methyl-3-butenenitrile may be distilled in a second distillation apparatus to obtain a 2-methyl-3-butenenitrile-enriched stream as a top product and a 2-methyl-3-butenenitrile-depleted stream (i.e. a 3-pentenenitrile-enriched stream) as a bottom product.

The first 3-pentenenitrile-enriched stream may comprise small amounts of 2-methyl-3-butenenitrile. These small amounts of 2-methyl-3-butenenitrile may be separated from 3-pentenenitrile in one or more distillations columns, where 2-methyl-3-butenenitrile is recovered as a top product and 3-pentenenitrile is recovered as a bottom product. For example, two or more 3-pentenenitrile-enriched streams may be combined and distilled in a single or shared distillation column or these streams may be distilled in separate distillation columns. 2-methyl-3-butenenitrile recovered from such distillation may be passed as feed to the isomerization reaction zone 50, and 3-pentenenitrile recovered from such distillation may be passed as feed to the second hydrocyanation reaction zone 60.

Removal of intermediate boilers, such as MGN, $C_8H_3C\equiv N$ compounds, phenol and cresols, from the reaction system may be facilitated by distilling the reaction product stream from the first reaction zone 4 in a particular manner. For example, after removing unreacted 1,3-butadiene and hydrogen cyanide from the reaction product stream from the first hydrocyanation reaction zone 4, the stream, comprising pentenenitriles, zero valent nickel and first phosphorus-containing ligand, may be fed into a distillation column having a feed Inlet, an upper draw outlet, and a bottom draw outlet. The distillation column may have a stripping section, a rectifying section or both. A rectifying section comprising at least one stage of separation is provided between the feed inlet and the upper draw outlet. A pentenenitrile-enriched stream is withdrawn from the upper draw outlet. A catalyst-enriched stream is withdrawn from the bottom draw outlet. The distillation column is operated in a manner such that the catalyst-enriched stream comprises at least 5% by weight of pentenenitrile including the sum of 3-pentenenitrile and 2-methyl-3-butenenitrile. In this way, intermediate boilers tend to pass into the catalyst-enriched stream. These compounds may then be removed at least in part from the reaction system by an extraction process into the raffinate and from the raffinate by the raffinate treatment process described above.

In a modification of this process for distilling the reaction product stream from the first hydrocyanation reaction zone 4 depleted of 1,3-butadiene and hydrogen cyanide, the distillation column is further provided with a side draw outlet. A rectifying section comprising at least two stages of separation is provided between the feed inlet and the upper draw outlet. A pentenenitrile-enriched stream is withdrawn from the upper draw outlet. A catalyst-enriched stream is withdrawn from the bottom inlet. The distillation column is further provided with a liquid collection apparatus, such as a chimney tray, in the rectifying section. Liquid in the liquid collection apparatus of the rectifying section is collected at a location between the feed stage and upper draw outlet. At least a portion of the collected liquid is withdrawn to obtain the side-draw stream. The distillation column may be operated in a manner such that the catalyst-enriched stream comprises at least 5% by weight of pentenenitrile Including the sum of 3-pentenenitrile and 2-methyl-3-butenenitrile. The distillation column may also be operated in a manner such that dinitriles and intermediate boilers, such as MGN, $C_8H_{13}C\equiv N$ compounds, phenol and cresols, tend to pass out of the column through the side draw outlet. The stream from the side draw may then be passed either directly or indirectly into an extraction system. In another embodiment, the stream from the side draw is passed to a distillation column to selectively remove phenols, cresols and $C_8H_{13}C\equiv N$ compounds. In this way, at least a portion of the $C_8H_{13}C\equiv N$ compounds, phenol and cresol are separated from recycled catalyst.

The first catalyst-enriched stream passes from separation section 6 through line 8. A portion of this catalyst enriched stream in line 8 is withdrawn forming a first catalyst purge stream, which passes through line 9. This purge stream comprises catalyst, catalyst degradation product and reaction byproduct. At least a portion of the catalyst from the first catalyst purge in line 8 is fed to a catalyst regeneration zone comprising liquid-liquid extraction to at least partially separate catalyst degradation product and reaction byproduct from the first hydrocyanation reaction catalyst.

At least 80%, preferably at least 90%, for example, 93 to 96%, at least 99%, at least 99.9%, and substantially all, of the first catalyst in stream 8 is recycled. A portion of the first catalyst recycle stream 8 is withdrawn in purge stream 9 for purification and recovery. In embodiments of the disclosed process, the minimum amount of circulating catalyst that is withdrawn, purified, recovered and optionally treated to increase its nickel content is selected from 2, 5, 10, 15 and 20% by weight of the circulating catalyst. In other embodiments, less than 100, 75, 50 and 25% by weight of the circulating catalyst may be withdrawn, purified, recovered and optionally treated to increase its nickel content. The purified and recovered catalyst is then returned to at least one of the first hydrocyanation 4, the isomerization reaction zone 40 and the second hydrocyanation zone 60.

The purification steps as applied to the hydrocyanation catalysts for making 3PN and adiponitrile may be segregated, in order to avoid (at least reducing to de minimis levels) co-mingling of the catalyst used in the first hydrocyanation reaction zone 4 and the catalyst used in the second hydrocyanation reaction zone 60.

The process conducted in a catalyst regeneration zone may comprise the steps of:
1) introducing a dinitrile stream comprising dinitrile and an extraction solvent stream comprising extraction solvent into an extraction zone;
2) contacting the catalyst purge with extraction solvent from the extraction solvent stream and dinitrile from the dinitrile stream in the extraction zone to obtain within the extraction zone at least two immiscible liquid phases including an extract phase and a raffinate phase;
3) withdrawing from the extract phase an extract stream comprising extraction solvent and catalyst;

4) withdrawing from the raffinate phase a raffinate stream comprising dinitrile, catalyst degradation product and reaction byproduct;
5) distilling the extract stream to obtain at least one extraction solvent-enriched stream and an extraction solvent-depleted stream (i.e. a catalyst-enriched stream) comprising separated catalyst; and
6) optionally, distilling the raffinate phase in one or more steps to purge catalyst degradation products and to provide a dinitrile stream depleted in such catalyst degradation products. Catalyst degradation products may have lower or higher boiling points than the adiponitrile, and this optional distillation step may be configured accordingly by one of ordinary skill given the vapor-liquid equilibrium data for the components to be distilled.

Purification or regeneration of catalyst results in removal of catalyst degradation products. Such catalyst degradation products may include one or more of, for example, one or more phosphorus-containing ligand hydrolysis products, e.g., phenol and substituted phenol, one or more phosphorus-containing ligand oxidation products, such as phosphates derived from the oxidation of phosphite ligands, Ni(C≡N)$_2$, ligand hydrolysis products and nickel metal.

Purification or regeneration of catalyst also results in removal of reaction byproducts. Examples of such reaction byproducts include a $C_8H_{13}C\equiv N$ compound, 2-methyl-2-butenenitrile, 2-pentenenitrile, 2-methylglutaronitrile, and ethylsuccinonitrile.

A catalyst purge stream, such as stream 9 or stream 47 may be fed into a liquid/liquid extraction zone. A non-polar solvent, such as an alkane, may also be fed into the liquid/liquid extraction zone. A polar solvent, which is immiscible with the non-polar solvent, may also be fed into the liquid/liquid extraction zone. The polar solvent introduced into extraction zone may comprise adiponitrile. The catalyst purge stream comprises reaction byproducts and catalyst degradation byproducts. In the extraction zone, there is formed a non-polar phase comprising non-polar solvent and catalyst and a polar phase (e.g., a raffinate) comprising polar solvent and, for example, reaction byproducts and catalyst degradation products. The non-polar phase is taken from the extraction zone to a distillation column. The polar phase is taken from the extraction zone to a separation section.

The extraction solvent provided to the extraction zone for purification or regeneration of the isomerization catalyst may be at least one hydrocarbon compound selected from the group consisting of linear aliphatic, branched aliphatic, unsubstituted cycloaliphatic, and alkyl-substituted cycloaliphatic hydrocarbons. Such extraction solvents may boil in the range of 30° C. to 135° C., for example, from 60° C. to 100° C., at a pressure of one atmosphere. The dinitrile feed to the extraction zone may be mainly composed of adiponitrile. MGN and ESN may be at least partially removed from the dintrile stream prior to recycling to the liquid/liquid extraction zone.

The extraction zone may comprise a plurality of extraction stages. A catalyst purge stream and, optionally, a side-draw stream comprising intermediate boilers may be charged into different extraction stages of the extraction zone. The side-draw stream may be generated during the distillation of pentenenitriles containing catalyst to obtain a pentenenitrile-enriched stream as an upper draw and a catalyst-enriched stream as a lower draw. Both the catalyst purge stream and the side-draw stream may comprise dinitriles and intermediate boilers, such as $C_8H_{13}C\equiv N$ compounds, phenol and cresols. Extract and raffinate phases may flow in a counter-current fashion within the extraction zone. The above-mentioned side-draw stream comprising intermediate boilers may be charged into a multiple stage extraction zone and into an extraction stage closer than the first stage to the extraction stage where the raffinate phase is withdrawn. Extraction solvent may be charged to the same extraction stage of the extraction zone where the raffinate phase is withdrawn from the extraction zone to obtain the raffinate stream. The catalyst-enriched stream may be charged to the same extraction stage of the extraction zone where the extract phase is withdrawn from the extraction zone to obtain the extract stream. In a multistage extraction zone, a portion of the catalyst enriched stream may also be charged to the same extraction stage of the extraction zone where the raffinate phase is withdrawn from the extraction zone to obtain the raffinate stream.

A stream comprising make-up catalyst from a make-up catalyst reactor may also be introduced to the catalyst loop downstream of the extraction zone. In a multi-stage extraction zone, comprising, for example, at least 3, for example, at least 4, for example, at least 5 extraction stages, make-up phosphite ligand of the catalyst may be Introduced near the stage where the where the catalyst purge stream is charged.

In the extraction zone, wherein an extract phase and a raffinate phase are produced, the molar ratio of total moles of mononitrile compounds divided by total moles of dinitrile compounds should be sufficient to achieve this phase separation. For example, this molar ratio may be between 0 and 0.5, for example, 0.005 to 0.5, for example, 0.01 to 0.25, for example, 0.05 to 0.20, for example, 0.05 and 0.15, for example, 0.1 and 0.5. The mononitriles in the extraction zone may include 4-pentenenitrile, 3-pentenenitrile, 2-pentenenitrile, 2-methyl-3-butenenitrile, 2-methyl-2-butenenitrile, and valeronitrile. The dinitriles in the extraction zone may include adiponitrile, 2-methylglutaronitrile, and ethylsuccinonitrile. In order to achieve proper extraction of catalyst into the extraction solvent phase, the flow of catalyst enriched stream into the extraction zone and the flow of the extraction solvent phase from the extraction zone should be controlled. Also, the flow of catalyst enriched stream into the extraction zone and the flow of the extraction solvent into the extraction zone should be controlled. For example, the ratio of mass flow of extraction solvent entering the extraction zone divided by sum of the mass flows of the dinitrile and catalyst feed to the extraction zone for the contacting may be less than about 2, for example, less than 1.5, for example, less than 1.2. Further, the flow of raffinate stream withdrawn from the extraction zone and the flow of the catalyst stream into the extraction zone should be controlled. For example, the ratio of mass flow of raffinate stream withdrawn from the extraction zone divided by mass flow of the pentenenitrile-depleted stream entering the extraction zone for the contacting may be greater than about 0.9. U.S. Pat. No. 3,773,809 to Walter teaches an example of a suitable liquid/liquid extraction process.

The temperature in the extraction zone to facilitate phase separation and catalyst extraction may be from 25° C. to 135° C., for example, 25° C. to 90° C., for example, 50° C. to 75° C. The concentration of mononitriles in the extraction zone (e.g., from the combined catalyst enriched stream) and dinitrile stream may be between 2-20%, for example, 5-15%, by weight of total mononitriles, for example, where the mononitrile component is calculated as the sum of the weights of mononitrile compounds comprising 2-pentenenitrile, 3-pentenenitrile, 4-pentenenitrile, 2-methyl-3-butenenitrile, 2-methyl-2-butenenitrile, and valeronitrile.

Non-polar solvent may be distillatively recovered and recycled to the extraction zone for purifying (i.e. regenerating) catalyst. For example, non-polar solvent may be distillatively recovered in a distillation column and returned to the extraction zone. The extraction zone, the line for transporting the extract phase to a distillation column, the distillation column, and the line for returning extraction solvent from the distillation column to the extraction zone, collectively, form a recovery loop for recycling non-polar solvent into the extraction zone.

The extract stream may be distilled in at least one distillation column at 1 psia to 22 psia (0.07 bar to 1.5 bar) pressure and with a base temperature of less than about 160° C., for example, less than about 150° C., for example; less than about 140° C. The base temperature is chosen in part to maintain the thermal stability of the catalyst composition. The 2PN/3PN ratio in the column bottoms may be controlled to reduce the amount of isomerization of 3PN to 2M3BN.

The raffinate stream from the extraction zone may be distilled in one or more distillation columns to separate dinitriles from other components of the raffinate stream, such as extraction solvent, pentenenitriles, reaction byproducts and catalyst degradation products. Dinitriles separated from the other components of the raffinate stream may then be recycled to the extraction zone.

Distillation of a raffinate phase is shown in FIG. 7, as described above.

Although a majority of the extraction solvent separates into the solvent phase in the extraction zone, some extraction solvent is extracted into the raffinate phase. The raffinate stream, therefore, comprises some extraction solvent. The raffinate stream may further comprise one or more of at least one pentenenitrile (typically a mixture of pentenenitriles), tertiary-butylcatechol, $C_8H_{13}C\equiv N$ compounds, phenol, cresols, and dinitriles comprising adiponitrile (ADN) and methylglutaronitrile (MGN). In a first distillation step of the raffinate stream, extraction solvent having a lower boiling point than pentenenitriles may be separated from other higher boiling constituents of the raffinate stream to obtain an extraction solvent-depleted raffinate stream. Such extraction solvents may have a boiling point of, for example, 30 to 135° C., for example, 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. This pentenenitrile-depleted raffinate stream may comprise, for example, a total of at least 0.01%, for example, at least 0.07%, for example, at least 0.1%, for example, less than 1%, by weight of pentenenitrile including the sum of 4-pentenenitrile, 3-pentenenitrile, and 2-pentenenitrile. Examples of pentenenitriles, which may be removed as an overhead stream in this second distillation step include 2-methyl-3-butenenitrile, 2-methyl-2-butenenitrile, trans-3-pentenenitrile, cis-3-pentenenitrile, trans-2-pentenenitrile, and cis-2-pentenenitrile. Such removed pentenenitriles may have an approximate boiling point within the range of from 120° C. to 150° C. The column may be operated under conditions sufficient to keep a majority of the intermediate boilers, such as $C_9$ mononitriles, in the pentenenitrile-depleted stream. These conditions may involve operating the column such that at least some pentenenitrile is included in the pentenenitrile depleted stream.

The pentenenitrile-depleted raffinate stream obtained in the above-mentioned second distillation step may be introduced into at least a third distillation step. In this third distillation step, compositions having a higher boiling point than dinitriles are separated as a bottom stream from the dinitriles and compounds, such as tertiary-butylcatechol, $C_8H_{13}C\equiv N$ compounds, phenol and cresols, if present. Such bottoms products may have a boiling point of, for example, at least 300° C. In contrast, most dinitriles in the pentenenitrile-depleted raffinate stream from the above-mentioned second distillation step would tend to have a boiling point within the approximate range of 260° C. to 300° C.

The third distillation step of the raffinate stream may occur in one or more distillation columns. In an example of using a single distillation column for this third distillation step, compounds having a boiling point of, for example, less than 250° C. are withdrawn as an overhead stream, compounds having a boiling point of, for example, from 260° C. to 300° C. are withdrawn as a side draw from the distillation column, and compounds having a boiling point of, for example, greater than 300° C. are withdrawn as a bottom stream. In this example of a third distillation step, the overhead stream may comprise compounds, such as $C_8H_{13}C\equiv N$ compounds, phenol and cresols, the side stream may comprise compounds, such as tertiary-butylcatechol and dinitriles, and the bottoms stream may comprise compounds, such as catalyst degradation products, including for example, $Ni(CN)_2$ and an organophosphate formed by oxidation of an organophosphite ligand. For example, tris(tolyl) phosphate is an oxidation byproduct of tris(tolyl)phosphite.

This separation may also take place in two distillation columns. When two distillation columns are used for the third distillation step, a first distillation column may be operated to produce a bottoms stream comprising compounds having a boiling point of greater than 300° C. and an overhead stream comprising dinitriles and, for example, $C_8H_{13}C\equiv N$ compounds, phenol and cresols. This overhead stream may then be passed to a second distillation column to produce dinitriles as a bottoms stream and an overhead stream comprising $C_8H_{13}C\equiv N$ compounds, phenol and cresols.

When the dinitrile stream from the third distillation step comprises methylglutaronitrile (MGN), in particular, 2-methylglutaronitrile (2-MGN), this stream may be further distilled to remove MGN from this stream to thereby produce a stream enriched in adiponitrile for recycle to the extraction zone. 2-MGN has an approximate boiling point of 269° C. to 271° C., whereas adiponitrile has an approximate boiling point of 295° C. Tertiary-butylcatechol, especially 4-tertiary-butylcatechol, has a boiling point of 285° C. The overhead cut point of the above-mentioned third distillation step for treating the raffinate stream may also be adjusted such that MGN is removed along with $C_8H_{13}C\equiv N$ compounds, phenol and cresols, as an overhead of the single distillation column with a side draw or as an overhead in of the second distillation column, when two columns are used. Removing MGN from the adiponitrile prevents unwanted buildup of MGN. The removal of MGN also facilitates the removal of $C_8H_{13}C\equiv N$ compounds, phenol and cresols from the catalyst recycle stream and the entire reaction system. Removing MGN further facilitates removal of any 2-ethylsuccinonitrile, an isomer of ADN and MGN. The boiling point of 2-ethylsuccinonitrile is 264° C. At least a portion of any tertiary-butylcatechol in the dinitrile stream may be removed with the MGN. The MGN-containing stream recovered from the distillation column may be further purified by removing impurities, such as phenols, cresols and TBC. The purified MGN may be commercially sold. MGN is useful as a solvent/intermediate in the fiber industry.

Although particular distillation steps are described above for converting the raffinate stream from the extraction zone into a purified adiponitrile stream, which is, in turn, recycled to the extraction zone, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

Bottoms comprising catalyst degradation products from the above-mentioned third distillation step may be passed to a wiped film evaporator (WFE) to recover adiponitrile in such bottoms. A wiped film evaporator may also be used to recover adiponitrile from catalyst degradation products in an adiponitrile recovery section.

After catalyst has passed through a distillation apparatus for distilling non-polar solvent from catalyst, the purified (i.e. regenerated) catalyst may be recycled to the a reaction zone. When catalysts, which are used in the first hydrocyanation reaction zone 4 and the isomerization zone 40, comprise the same phosphorus-containing ligand, at least a portion of the purified (i.e. regenerated) catalyst may be recycled to either or both of these reaction zones. Any purified or partially purified stream of catalyst, which is subsequently fed to a reaction zone, may be provided with additional zero-valent Ni, for example, and/or phosphorus-containing ligand.

The composition of the column bottoms from a distillation column, which is used to separate extraction solvent from catalyst, may comprise, for example, 1-2 wt % zero valent Ni, 70-90 wt % phosphorus-containing ligand, less than 4 wt % of the non-polar solvent, such a cyclohexane, used in the extraction zone, less than 10 wt % pentenenitriles, and less than 10 wt % dinitriles.

In order to achieve a ratio of 2PN to 3PN in column bottoms, sufficient to inhibit the isomerization of 3PN to 2M3BN in column bottoms, it is generally necessary to increase the amount of 2PN, which would otherwise be present in the column bottoms. The proper 2PN/3PN ratio may be achieved in a number of ways.

2PN may be obtained from external or internal sources. For example, 2PN may be obtained from the same or different plant used to make 3PN and adiponitrile.

2PN is produced in various amounts in the first hydrocyanation reaction to make 3PN, the isomerization reaction to convert 2M3BN to 3PN, and the second hydrocyanation reaction to make adiponitrile. The predominant linear pentenenitrile product formed by the hydrocyanation of BD or the isomerization of 2M3BN is trans-3PN. However, this predominantly trans-3PN product may also contain smaller quantities of 4PN, cis-3PN, 2PN, and 2M2BN isomers.

2PN can be made in larger quantities during the hydrocyanation of 3PN and/or 4PN to form ADN, among other dinitriles, from the concurrent isomerization of 3PN to 2PN. Separation of the cis-2PN isomer by the fractional distillation of mixtures of pentenenitrile isomers, as disclosed in the art, can provide a source of isolated 2PN to be used to adjust the 3PN/2PN ratio in column bottoms. See, for example, U.S. Pat. No. 3,852,327. Alternatively, the cis-2PN need not be isolated from mixtures of pentenenitrile isomers. For example, 2PN mixtures comprising 2PN, 3PN, and 4PN may be separated by vacuum distillation from the pentenenitrile hydrocyanation reaction product comprising unreacted pentenenitriles, ADN and other six carbon dinitriles, catalyst, and promoter, by methods known in the art. The 2PN mixture, as a distillation column side stream or overhead make, may then be recycled directly to a distillation column or to an appropriate point upstream of the distillation column to adjust the 2PN/3PN ratio in the column bottoms. Pentenenitrile mixtures comprising 2PN, 3PN, and 4PN, can be recovered, for example, by distillation of the extract, raffinate, or extract and raffinate phases of a liquid-liquid extraction process. These recovered mixtures comprising 2PN may also be recycled to a distillation column.

For example, a raffinate stream from a liquid/liquid extraction process may be distilled in a distillation column to remove residual extraction solvent and produce a distilled raffinate stream depleted in extraction solvent. Referring to FIG. 7, such a distilled raffinate stream depleted in extraction solvent is introduced into distillation zone 80 through line 81. The distillation conditions in distillation zone 80 are such that pentenenitriles are removed as an overhead stream through line 82. These pentenenitriles may be selected from a group comprising 3-pentenenitrile, 4-pentenenitrile, 2-methyl-3-butenenitrile, trans-2-pentenenitrile, cis-2-pentenenitrile, and 2-methyl-2-butenenitrile. FIG. 7 shows the stream in line 82 being used as a feed to distillation column 90. However, according to one method for adjusting the 2PN/3PN ratio in the bottoms of a distillation column, distillation zone 90 is bypassed, and the stream in line 82 is fed to a distillation column including 3PN and catalyst in the column bottoms or to a point upstream of this column, such that the 2PN/3PN ratio in the column bottoms is maintained at a proper level to reduce isomerization of 3PN to 2M3BN in these bottoms.

According to another option, distillation zone 90 is not bypassed. Instead, as shown in FIG. 7, the stream in line 82 is distilled in distillation zone 90 to obtain a stream enriched in cis-2PN, which is withdrawn as an overhead stream through line 91, and cis-2PN depleted stream, which is withdrawn through line 92. The stream enriched in cis-2PN may then be fed to a distillation column including 3PN and catalyst in the column bottoms or to a point upstream of this column, such that the 2PN/3PN ratio in the column bottoms is maintained at a proper level to reduce isomerization of 3PN to 2M3BN in these bottoms.

When a stream comprising 2PN is added to increase the ratio of 2PN/3PN in column bottoms of a distillation column, the stream comprising 2PN may be added to a point downstream of a reaction zone. For example, when the column bottoms comprise 3PN and a catalyst from the first hydrocyanation reaction zone, the stream comprising 2PN may be added downstream from the first hydrocyanation reaction zone. Also, when the column bottoms comprise 3PN and a catalyst from the isomerization reaction zone, the stream comprising 2PN may be added downstream from the second reaction zone. Furthermore, when the column bottoms comprise 3PN and a catalyst from the second hydrocyanation reaction zone, the stream comprising 2PN may be added downstream from the of the second hydrocyanation reaction zone.

When a stream comprising 2PN is added to increase the ratio of 2PN/3PN in column bottoms of a distillation column, and the distillation column is downstream from an extraction zone for recovering a catalyst, the stream comprising 2PN may be added to a point downstream of the extraction zone. For example, when the column bottoms comprise 3PN and a catalyst recovered from an extraction zone for recovering the first hydrocyanation catalyst, the stream comprising 2PN may be added downstream of the of this extraction zone. Also, when the column bottoms comprise 3PN and a catalyst recovered from an extraction zone for recovering the isomerization catalyst, the stream comprising 2PN may be added downstream of this extraction zone. Furthermore, when the column bottoms comprise 3PN and a catalyst recovered from an extraction zone for recovering the second hydrocyanation catalyst, the stream comprising 2PN may be added downstream of the of this extraction zone.

The Isomerization Reaction Zone

As shown in FIG. 4, 2-methyl-3-butenenitrile (2M3BN) containing feedstock may be fed to an isomerization reaction zone 40, e.g., via line 41 and a catalyst may be fed to the isomerization reaction zone 40, e.g., via line 42.

In the isomerization reaction zone 40 at least a portion of the first 2-methyl-3-butenenitrile-enriched stream is reacted in the presence of a catalyst, which comprises zero-valent nickel and at least one phosphorus-containing ligand.

The 2-methyl-3-butenenitrile feed to the isomerization reaction zone 40 is obtained from distillation steps described herein above. This feed may comprise at least 30 wt % 2M3BN. This feed may also comprise less than 70 wt % of pentenenitriles other than 2M3BN, and less than 1 wt % of phosphorus-containing ligand, which is used in the first hydrocyanation reaction zone 4, for example, less than 0.1 wt. %.

The 2M3BN-containing feed and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The feed molar ratio of 2M3BN to catalyst for the isomerization reaction step is generally greater than 1:1, usually in the range from about 5:1 to 20,000:1, for example, from about 100:1 to about 5,000:1.

When a monodentate ligand is used, the molar ratio of monodentate ligand to zero valent nickel in the catalyst for the isomerization reaction may be from about 1:1 to about 50:1, for example, from about 1:1 to about 30:1. When a bidentate ligand is used, the molar ratio of bidentate ligand to zero valent nickel in the catalyst for the isomerization reaction may be from 1:1 to 10:1, for example, from 1:1 to 5:1.

The residence time in the reaction zone for the isomerization reaction may be from about 0.1 hour to about 15 hours, for example, from about 1 hour to about 10 hours.

For the isomerization of 2M3BN to produce 3PN, the reaction temperature may be maintained within the range of about 0° C. to about 200° C., for example, within the range of about 50° C. to about 165° C. Again, though the Invention is not limited by an upper limit of pressure for this reaction step, for practical purposes the pressure generally ranges from about 15 psia to about 300 psia (about 1.03 bar to about 20.7 bar).

The reaction product mixture from the 2M3BN isomerization reaction zone may include certain low boilers, 3PN, 2M3BN, (Z)-2M2BN and catalyst. At least some of the low boilers may be removed in a first distillation step. Then, a stream depleted in low boilers may be distilled in one or more distillation apparatus to recover a (Z)-2M2BN-enriched stream, a (Z)-2M2BN-depleted stream Including 3PN and 2M3BN, and a catalyst-enriched stream including the catalyst. At least a portion of the catalyst-enriched stream may be recycled to the 2M3BN isomerization reaction.

The (Z)-2M2BN-depleted stream may be further distilled to obtain a 2M3BN-enriched stream and a 2M3BN-depleted stream Including 3PN. The 2M3BN-enriched stream from the BD hydrocyanation process may be a 2M3BN feed to the 2M3BN isomerization process.

The effluent from the isomerization reaction zone 40 comprises 3-pentenenitrile, 2-methyl-3-butenenitrile and catalyst. In FIG. 4, this effluent from the isomerization reaction zone 40 passes through line 43. Components of the reaction effluent may be separated, at least partially by one or more distillation steps, represented, diagrammatically, by separation section 44 in FIG. 4. In particular, these distillation steps may take place in one or more distillation columns, to provide:

1) a second 2-methyl-3-butenenitrile-enriched stream 45;
2) a second 3-pentenenitrile-enriched stream 48; and
3) a second catalyst-enriched stream 46.

The second 2-methyl-3-butenenitrile-enriched stream and the second 3-pentenenitrile-enriched stream may each contain less than a total of 500 parts per million by weight of the phosphorus-containing ligand. For example, the second 3-pentenenitrile-enriched stream may contain less than 300 ppm, for example, less than 100 ppm, of the phosphorus-containing ligand.

The second 3-pentenenitrile-enriched stream may comprise small amounts of 2-methyl-3-butenenitrile. These small amounts of 2-methyl-3-butenenitrile may be separated from 3-pentenenitrile in one or more distillations columns, where 2-methyl-3-butenenitrile is recovered as a top product and 3-pentenenitrile is recovered as a bottom product. For example, the first and second 3-pentenenitrile-enriched streams may be combined and distilled in a single or shared distillation column or these streams may be distilled in separate distillation columns. 2-Methyl-3-butenenitrile recovered from such distillation may be passed as feed to the isomerization reaction zone 40, and 3-pentenenitrile recovered from such distillation may be passed as feed to the second hydrocyanation reaction zone 60.

The second 3-pentenenitrile-enriched stream may further comprise (Z)-2-methyl-2-butenenitrile, and the second 3-pentenenitrile-enriched stream may be distilled to obtain a (Z)-2-methyl-3-butenenitrile-enriched stream, comprising 2-methyl-3-butenenitrile and (Z)-2-methyl-2-butenenitrile, along with other low boilers as described previously, as a top product, and a (Z)-2-methyl-2-butenenitrile-depleted stream, comprising 3-pentenenitrile, 2-methyl-3-butenenitrile, and, depending on distillation conditions, some (Z)-2-methyl-2-butenenitrile, as a bottom product.

At least one distillation system for distilling the effluent from the isomerization reaction zone 40 is described above. However, it will be understood that it is within the skill in the art to design and operate other distillation systems to achieve the same or essentially the same results. For example, a stream comprising 3PN and 2M3BN obtained by distilling the effluent from the isomerization reaction zone 40 may be passed to a distillation apparatus, such as the distillation apparatus, which is used in the distillation of the effluent form the first hydrocyanation reaction zone 4, to obtain a 3PN-enriched stream and a 2M3BN-enriched stream.

At least a portion of the second 3-pentenenitrile-enriched stream may be used to prepare a catalyst solution. In particular, at least a portion of the second 3-pentenenitrile-enriched stream may be passed into a catalyst reaction zone, wherein nickel metal reacts with the phosphorus-containing ligand to produce a catalyst solution, comprising catalyst and pentenenitriles. A portion of this catalyst solution may be passed into the isomerization reaction zone 40. When the respective catalysts comprise the same phosphorus-containing ligand, a portion of the catalyst from the isomerization reaction zone 40 may be passed to the first hydrocyanation reaction zone 4 and vice versa.

The second catalyst-enriched stream passes from separation section 44 through line 46. A portion of this catalyst enriched stream in line 46 is withdrawn forming a second catalyst purge stream, which passes through line 47. This purge stream comprises the isomerization catalyst, catalyst degradation product and reaction byproduct. At least a portion of the catalyst from the second catalyst purge stream in line 47 may be fed to a second catalyst regeneration zone comprising liquid-liquid extraction to at least partially separate catalyst degradation product and reaction byproduct from a separated first catalyst. According to an option not shown in FIG. 4, at least a portion of the second catalyst purge in line 47 may be fed to a first catalyst regeneration zone, which is used to regenerate the catalyst from the first hydrocyanation reaction zone 4. In such an option, the second catalyst regeneration zone may be omitted.

At least 10%, for example, at least 50%, for example, 75%, for example, 80% to 90%, of the second catalyst in stream 46 is recycled, and the remaining amount in purge stream 47 is withdrawn for purification and recovery. In one embodiment, 20 to 60% by weight of the circulating catalyst can be withdrawn, purified, recovered and optionally treated to increase its nickel content. The purified and recovered catalyst is then returned to any of the first hydrocyanation reaction zone 4, the isomerization reaction zone 40 and the second hydrocyanation reaction zone 60. Depending upon the activity of the isomerization catalyst, one embodiment of the disclosed process may Include charging the isomerization catalyst to the isomerization reaction zone 40 and not recycling it.

The process conducted in a catalyst regeneration zone for regenerating an isomerization catalyst may comprise the steps of:

1) introducing a dinitrile stream comprising dinitrile and an extraction solvent stream comprising extraction solvent into an extraction zone;
2) contacting the catalyst purge with extraction solvent from the extraction solvent stream and dinitrile from the dinitrile stream in the extraction zone to obtain within the extraction zone at least two immiscible liquid phases including an extract phase and a raffinate phase;
3) withdrawing from the extract phase an extract stream comprising extraction solvent and catalyst;
4) withdrawing from the raffinate phase a raffinate stream comprising dinitrile, catalyst degradation product and reaction byproduct;
5) distilling the extract stream to obtain at least one extraction solvent-enriched stream and an extraction solvent-depleted stream (i.e. a catalyst-enriched stream) comprising separated catalyst; and
6) optionally, distilling the raffinate phase in one or more steps to purge catalyst degradation products and to provide a dinitrile stream depleted in such catalyst degradation products. Catalyst degradation products may have lower or higher boiling points than the adiponitrile and this optional distillation step may be configured accordingly by one of ordinary skill given the vapor-liquid equilibrium data for the components to be distilled.

Purification or regeneration of isomerization catalyst results in removal of catalyst degradation products. Such catalyst degradation products include one or more of, for example, one or more phosphorus-containing ligand hydrolysis products, e.g., phenol and substituted phenol, one or more phosphorus-containing ligand oxidation products, such as phosphates derived from the oxidation of phosphite ligands, $Ni(C\equiv N)_2$, ligand hydrolysis products and nickel metal.

Purification or regeneration of isomerization catalyst also results in removal of reaction byproducts. Examples of such reaction byproducts include a $C_8H_{13}C\equiv N$ compound, 2-methyl-2-butenenitrile, 2-pentenenitrile, 2-methylglutaronitrile, and ethylsuccinonitrile.

A catalyst purge stream 47 is fed into a liquid/liquid extraction zone. The liquid/liquid extraction zone for purification of the isomerization catalyst may be the same as or different from the liquid/liquid extraction zone for treating one or more of the hydrocyanation catalysts. In one embodiment, the purification of the three catalysts takes place in three separate zones, each dedicated to a particular catalyst. In another embodiment, the first hydrogenation catalyst and the isomerization catalyst are purified in the same liquid/liquid extraction zone. In another embodiment, all three of the catalysts are purified in the same liquid/liquid extraction zone.

A non-polar solvent, such as an alkane, is fed into the liquid/liquid extraction zone. A polar solvent, which is immiscible with the non-polar solvent, is also fed into the liquid/liquid extraction zone. In the extraction zone, there is formed a non-polar phase comprising non-polar solvent and catalyst and a polar phase (e.g., a raffinate) comprising polar solvent and, for example, reaction byproducts and catalyst degradation products. The non-polar phase is taken from the extraction zone to a distillation section. The polar phase is taken from the extraction zone to a separation section to recover the polar solvent.

The extraction solvent provided to the extraction zone may be at least one hydrocarbon compound selected from the group consisting of linear aliphatic, branched aliphatic, unsubstituted cycloaliphatic, and alkyl-substituted cycloaliphatic hydrocarbons. Such extraction solvents may boil in the range of 30° C. to 135° C., for example, 60° C. to 100° C., at a pressure of one atmosphere. The dinitrile feed to the extraction zone may be mainly composed of adiponitrile. MGN and ESN may be removed from the dintrile stream prior to recycle to the liquid/liquid extraction zone. However, even when MGN and ESN are removed, small amounts of MGN and ESN may still be present, because these isomers of adiponitrile may not be completely removed in the distillation process used to treat the raffinate stream.

The extraction zone may comprise a plurality of extraction stages. A catalyst purge stream and, optionally, a side-draw stream comprising intermediate boilers may be charged into different extraction stages of the extraction zone. The side-draw stream may be generated during the distillation of pentenenitriles containing catalyst to obtain a pentenenitrile-enriched stream as an upper draw and a catalyst-enriched stream as a lower draw. Both the catalyst purge stream and the side-draw stream may comprise dinitriles and intermediate boilers, such as $C_8H_{13}C\equiv N$ compounds, phenol and cresols. Extract and raffinate phases may flow in a counter-current fashion within the extraction zone. The above-mentioned side-draw stream comprising intermediate boilers may be charged into a multiple stage extraction zone and into an extraction stage closer than the first stage to the extraction stage where the raffinate phase is withdrawn. Extraction solvent may be charged to the same extraction stage of the extraction zone where the raffinate phase is withdrawn from the extraction zone to obtain the raffinate stream. The catalyst-enriched stream may be charged to the same extraction stage of the extraction zone where the extract phase is withdrawn from the extraction zone to obtain the extract stream. In a multistage extraction zone, a portion of the catalyst enriched stream may also be charged to the same extraction stage of the extraction zone where the raffinate phase is withdrawn from the extraction zone to obtain the raffinate stream.

A stream comprising make-up ligand may also be introduced into the extraction zone.

In the extraction zone, wherein an extract phase and a raffinate phase are produced, the molar ratio of total moles of mononitrile compounds divided by total moles of dinitrile compounds should be sufficient to achieve this phase separation. For example, this ratio may be between 0 and 0.5, for example, 0.005 to 0.5, for example, 0.01 to 0.25, for example, 0.05 to 0.20, for example, 0.05 and 0.15, for example, 0.1 and 0.5. The mononitriles in the extraction zone may include 4-pentenenitrile, 3-pentenenitrile, 2-pentenenitrile, 2-methyl-3-butenenitrile, 2-methyl-2-butenenitrile, and valeronitrile. The dinitriles in the extraction zone may Include adiponitrile, 2-methylglutaronitrile, and ethylsuccinonitrile. In order to achieve proper extraction of catalyst into the extraction solvent phase, the flow of catalyst enriched stream into the extraction zone and the flow of the extraction solvent phase from the extraction zone should be controlled. Ratios of extraction solvents and catalyst charged to the extraction zone for purifying the isomerization reaction catalyst are substantially the same as described above for extraction zone for purifying the first hydrocyanation reaction catalyst. The boiling point of the dinitrile may be greater than a boiling point of 3-pentenenitrile at a given pressure. Examples of such dinitrile compounds include adiponitrile, 2-methylglutaronitrile, ethylsuccinonitrile, and mixtures of these dinitriles. The temperature in the extraction zone to facilitate phase separation and catalyst extraction may be from 25° C. to 135° C., for example, for example, 25° C. to 90° C., for example, 50° C. to 75° C. The concentration of mononitriles in the extraction zone (e.g., from the combined catalyst enriched stream and dinitrile stream) may be between 2-20%, for example, 5-15%, by weight of total mononitriles, for example, where the mononitrile component is calculated as the sum of the weights of mononitrile compounds comprising 2-pentenenitrile, 3-pentenenitrile, 4-pentenenitrile, 2-methyl-3-butenenitrile, 2-methyl-2-butenenitrile, and valeronitrile.

Non-polar solvent may be distillatively recovered and recycled to the extraction zone for purifying (i.e. regenerating) isomerization catalyst. For example, non-polar solvent may be distillatively recovered in a distillation column and returned to the extraction zone. The extraction zone, the line for transporting the extract phase to a distillation column, the distillation column, and the line for returning extraction solvent from the distillation column to the extraction zone, collectively, form a recovery loop for recycling non-polar solvent into the extraction zone.

The extract stream may be distilled in at least one distillation column at 1 psia to 22 psia (0.07 bar to 1.5 bar) pressure and with a base temperature of less than about 160° C., for example, less than about 150° C., for example, less than about 140° C., for example, less than about 130° C., or, for example, less than about 120° C. The base temperature is chosen in part to maintain the thermal stability of the catalyst composition. The 2PN/3PN ratio in the column bottoms may be controlled to reduce the amount of isomerization of 3PN to 2M3BN.

The raffinate stream from the extraction zone for treating the isomerization purge stream may be distilled in one or more distillation columns to separate dinitriles from other components of the raffinate stream, such as extraction solvent, pentenenitriles, reaction byproducts and catalyst degradation products. Dinitriles separated from other components of the raffinate stream may then be recycled to the extraction zone. The distillation zone, which is used to distill the raffinate from the extraction of the Isomerization purge stream, may be the same as or different from the distillation zone used to distill a raffinate from the extraction of the purge stream 9 from the first hydrogenation reaction zone 4 and/or a concentrated catalyst stream from extraction of effluent from the second hydrogenation zone 60 to make adiponitrile. In one embodiment, three separate distillation zones are provided for treating three separate raffinates, wherein a first raffinate is produced from the extraction of purge stream 9 containing the first hydrogenation reaction zone 4, a second raffinate is produced from the extraction of purge stream 47 containing isomerization catalyst, and a third raffinate is produced from the extraction of effluent, or a distillation fraction thereof, of the second hydrogenation zone 60 for making adiponitrile. In another embodiment, two distillation zones are used, wherein a shared distillation zone is used to treat both the raffinate produced from extraction of purge stream 9 and purge stream 40, and a second distillation zone is used to treat raffinate produced from the extraction of effluent, or a distillation fraction thereof, of the second hydrogenation zone 60 for making adiponitrile. In another embodiment, a single, shared distillation zone is used to treat all three raffinates.

Distillation of the raffinate phase is shown in FIG. 7, as described above.

Although a majority of the extraction solvent separates into the solvent phase in the extraction zone, some extraction solvent is extracted into the raffinate phase. The raffinate stream, therefore, comprises some extraction solvent. The raffinate stream may further comprise one or more of at least one pentenenitrile (typically a mixture of pentenenitriles), tertiary-butylcatechol, $C_8H_{13}C{\equiv}N$ compounds, phenol, cresols, and dinitriles comprising adiponitrile (ADN) and methylglutaronitrile (MGN). In a first distillation step of the raffinate stream, extraction solvent having a lower boiling point than pentenenitriles may be separated from other higher boiling constituents of the raffinate stream to obtain an extraction solvent-depleted raffinate stream. Such extraction solvents may have a boiling point of, for example, from 30 to 135° C., for example, from 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. This pentenenitrile-depleted raffinate stream may comprise, for example, a total of at least 0.01%, for example, at least 0.07%, for example, at least 0.1%, for example, less than 1%, by weight of pentenenitrile including the sum of 4-pentenenitrile, 3-pentenenitrile, and 2-pentenenitrile. Examples of pentenenitriles, which may be removed as an overhead stream in this second distillation step include 2-methyl-3-butenenitrile, trans-3-pentenenitrile, cis-3-pentenenitrile, trans-2-pentenenitrile, and cis-2-pentenenitrile. Such removed pentenenitriles may have an approximate boiling point within the range of from 120° C. to 150° C.

The pentenenitrile-depleted raffinate stream obtained in the above-mentioned second distillation step may be introduced into at least a third distillation step. In this third distillation step, compositions having a higher boiling point than dinitriles are separated as a bottom stream from the dinitriles and compounds, such as tertiary-butylcatechol, $C_8H_{13}C\equiv N$ compounds, phenol and cresols, if present. Such bottoms products may have a boiling point of, for example, at least 300° C. In contrast, most dinitriles in the pentenenitrile-depleted raffinate stream from the above-mentioned second distillation step would tend to have a boiling point within the approximate range of 260° C. to 300° C.

The third distillation step of the raffinate stream may occur in one or more distillation columns. In an example of using a single distillation column for this third distillation step, compounds having a boiling point of, for example, less than 250° C. are withdrawn as an overhead stream, compounds having a boiling point of, for example, from 260° C. to 300° C. are withdrawn as a side draw from the distillation column, and compounds having a boiling point of, for example, greater than 300° C. are withdrawn as a bottom stream. In this example of a third distillation step, the overhead stream may comprise compounds, such as $C_8H_{13}C\equiv N$ compounds, phenol and cresols, the side stream may comprise compounds, such as tertiary-butylcatechol and dinitriles, and the bottoms stream may comprise compounds, such as catalyst degradation products, including for example, $Ni(CN)_2$ and an organophosphate formed by oxidation of an organophosphite ligand. For example, tris(tolyl) phosphate is an oxidation byproduct of tris(tolyl)phosphite.

This separation may also take place in two distillation columns. When two distillation columns are used for the third distillation step, a first distillation column may be operated to produce a bottoms stream comprising compounds having a boiling point of greater than 300° C. and an overhead stream comprising dinitriles and, for example, $C_8H_{13}C\equiv N$ compounds, phenol and cresols. This overhead stream may then be passed to a second distillation column to produce dinitriles as a bottoms stream and an overhead stream comprising lower boilers, such as $C_8H_{13}C\equiv N$ compounds, phenol and cresols.

When the dinitrile stream from the third distillation step comprises methylglutaronitrile (MGN), in particular, 2-methylglutaronitrile (2-MGN), this stream may be further distilled to remove MGN from this stream to thereby produce an essentially pure adiponitrile stream for recycle to the extraction zone. 2-MGN has an approximate boiling point of 269° C. to 271° C., whereas adiponitrile has an approximate boiling point of 295° C. Tertiary-butylcatechol, especially 4-tertiary-butylcatechol, has a boiling point of 285° C. The overhead cut point of the above-mentioned third distillation step for treating the raffinate stream may also be adjusted such that MGN is removed along with $C_8H_{13}C\equiv N$ compounds, phenol and cresols, as an overhead of the single distillation column with a side draw or as an overhead in of the second distillation column, when two columns are used. Removing MGN from the adiponitrile prevents unwanted buildup of MGN. The removal of MGN also facilitates the removal of $C_8H_{13}C\equiv N$ compounds, phenol and cresols from the catalyst recycle stream and the entire reaction system. Removing MGN further facilitates removal of any 2-ethylsuccinonitrile, an isomer of ADN and MGN. The boiling point of 2-ethylsuccinonitrile is 264° C. At least a portion of any tertiary-butylcatechol in the dinitrile stream may be removed with the MGN.

Although particular distillation steps are described above for converting the raffinate stream from the extraction zone into a purified adiponitrile stream, which is, in turn, recycled to the extraction zone, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

Bottoms comprising catalyst degradation products from the above-mentioned third distillation step may be passed to a wiped film evaporator (WFE) to recover adiponitrile in such bottoms. A wiped film evaporator may also be used to recover adiponitrile from catalyst degradation products in an adiponitrile recovery section.

After catalyst has passed through a distillation apparatus for distilling non-polar solvent from catalyst, the purified (i.e. regenerated), isomerization catalyst may be recycled to the isomerization reaction zone or another reaction zone. When the catalysts, which are used in the first hydrocyanation reaction zone 4 and the isomerization reaction zone 40, comprise the same phosphorus-containing ligand, at least a portion of the purified (i.e. regenerated) catalyst may be recycled to the first hydrocycanation reaction zone 4 and/or the isomerization reaction zone 40. When the catalysts, which are used for the isomerization reaction zone and the second hydrocyanation reaction zone, comprise the same phosphorus-containing ligand, at least a portion of the purified (i.e. regenerated) catalyst may be recycled to the isomerization reaction zone and/or the second hydrocyanation reaction zone to make adiponitrile. Any purified or partially purified stream of isomerization catalyst, which is subsequently fed to a reaction zone, may be provided with additional zero-valent Ni, for example, and/or phosphorus-containing ligand. In an embodiment where the isomerization reaction zone 40 and the second hydrocyanation reaction zone 60 share catalyst, the make-up catalyst for the isomerization reaction zone 40 may be recovered from the catalyst recycle stream of the second hydrocyanation reaction zone 60. This embodiment is not illustrated in the Figures.

The Second Hydrocyanation Zone

As shown in FIG. 6, 3-pentenenitrile (3PN) containing feedstock may be fed to a second hydrocyanation reaction zone 60, e.g., via line 62, a hydrogen cyanide feed may be fed to the second hydrocyanation reaction zone 60, e.g., via line 60, and a catalyst may be fed to the second hydrocyanation reaction zone 60, e.g., via line 61. The catalyst feed also comprises a Lewis acid promoter.

A first 3-pentenenitrile stream is obtained from the distillation of the effluent from the first hydrocyanation reaction zone 4. A second 3-pentenenitrile stream is obtained from the distillation of the effluent of the isomerization reaction zone 40. In the second hydrocyanation reaction zone 60, at least a portion of the first 3-pentenenitrile-enriched stream and the second 3-pentenenitrile-enriched stream is reacted with hydrogen cyanide in the presence of a catalyst, comprising a zero-valent nickel, at least one bidentate phosphorus-containing ligand, and at least one promoter.

The 3-pentenenitrile feed to the second hydrocyanation reaction zone 60 is obtained from distillation steps described herein above. This feed may comprise at least 95 wt % 3PN. This feed may also comprise less than 5 wt % of pentenenitriles other than other than 3PN, and less than 0.1 wt % of monodentate phosphorus-containing ligand.

The 3PN feed may comprise less than 5000 parts per million (ppm) $C_9$ mononitriles, for example, less than 2000 parts per million (ppm) $C_9$ mononitriles, for example, less than 1000 parts per million (ppm) $C_9$ mononitriles, for example, less than 600 parts per million (ppm) $C_9$ mononitriles.

The HC≡N feed to the first hydrocyanation reaction zone 4 and the second hydrocyanation reaction zone 60 may be a product of the Andrussow process that is dried to less than about 250 ppm water, for example, less than 125 ppm water, for example, less than 80 ppm water, by distillation prior to entry into olefin hydrocyanation reaction zones. However, the HCN feed will usually contain at least some water. Very dry HCN is unstable, and, for this reason, it may be undesirable to provide completely anhydrous HCN. Accordingly, the HCN feed may comprise at least 10 ppm, for example, at least 25 ppm, for example, at least 50 ppm, water.

The hydrogen cyanide (HC≡N) is preferably substantially free of carbon monoxide, oxygen and ammonia. This HC≡N can be introduced to the first hydrocyantion reaction zone 4 and the second hydrocyanation reaction zone 60 as a vapor, liquid, or mixtures thereof; see, for example, European Patent Publication No. 1 344 770. As an alternative, a cyanohydrin can be used as the source of HC≡N; see, for example, U.S. Pat. No. 3,655,723.

The HC≡N feed, the 3PN-containing feed, and the catalyst composition are contacted in a reaction zone which may be contained in any suitable equipment known to one skilled in the art. One or more pieces of conventional equipment may be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

3PN hydrocyanation may be performed by reacting HC≡N and 3PN as a vapor, liquid, or mixtures thereof. As an alternative, a cyanohydrin may be used as the source of HC≡N.

The steps for making 3-pentenenitrile and the steps reacting 3-pentenenitrile with hydrogen cyanide need not take place in the same location or facility. For example, the isomerization reaction zone 40 and the second hyrdrocyanation reaction zone 60 may be separated from each other by a distance of at least 500 meters. The second hydrocyanation reaction zone 60 may be capable of being operated separately and independently from the first hydrocyanation reaction zone 4 and the isomerization reaction zone 40.

In the 3PN hydrocyanation reaction, promoters are provided to enhance the production of dinitriles. As known in the art, promoters influence both catalyst activity and selectivity to the desired ADN. Promoters employed include salts of metals having atomic numbers 13, 21-32, 39-50, and 57-80, for example, zinc, and compounds of the formula $BR'_3$ wherein $R'$ is an alkyl or an aryl radical of up to 18 carbon atoms, for example triphenylboron, $(C_6H_5)_3B$. The anions of the metal salts include halides, for example chloride, sulfates, phosphates, and lower aliphatic carboxylates. Useful promoters are generally known in the art as Lewis acids. The mole ratio of promoter to nickel in the catalyst is sufficient to promote the hydrocyanation of 3-pentenenitrile, and in one embodiment may be in the range of 1:20 to 50:1, for example, from 0.2:1 to 2:1 when the Lewis acid promoter is $ZnCl_2$.

In the 3PN hydrocyanation process, a 2M3BN-depleted stream from the BD hydrocyanation process, a 2M3BN-depleted stream from the 2M3BN isomerization process, or a combination thereof, is a useful feed stream. The 3PN hydrocyanation reaction temperature may be maintained within the range of about 0° C. to about 150° C., for example, within the range of about 25° C. to about 80° C. Generally, the reaction pressure should be sufficient to maintain the HC≡N in contact with the catalyst dissolved in the liquid reaction mixture. Such pressure is at least, in part, a function of the amount of unreacted HC≡N present in the reaction mixture. While an upper limit of pressure for this reaction step is not limited to any particular pressure, for practical purposes the pressure generally ranges from about 15 psia to about 300 psia (about 1.03 bar to about 20.7 bar).

The overall feed molar ratio of 3PN to HC≡N may be in the range of 1:1 to 100:1, for example, in the range of 1:1 to about 5:1.

The molar ratio of HC≡N to catalyst in the reaction of 3PN with HC≡N may be in the range of 10:1 to 5000:1, for example, 100:1 to 3000:1, for example, in the range 300:1 to 2000:1.

The phosphorus-containing ligand used in the reaction of 3PN with HC≡N is, preferably, a bidentate ligand. The molar ratio of bidentate ligand to nickel in the catalyst for the 3PN hydrocyanation step may be from 1:1 to 10:1, for example, 1:1 to 5:1, for example, 1:1 to 3:1. A mixture of monodentate and bidentate may also be used in the 3PN hydrocyanation step. When such a mixture is used the molar ratio of monodentate ligand to bidentate ligand may from 1:10 to 10:1.

The residence time in the 3PN hydrocyanation reaction zone for this reaction step is typically determined by the desire to obtain a certain degree of conversion of pentenenitriles, HC≡N, or a combination thereof. In addition to residence time, catalyst concentration and reaction temperature will also affect conversion of reactants to products. Generally, residence times will be in the range of about 0.1 hour to about 30 hours, for example, in the range of about 1 hour to about 20 hours. The HC≡N conversion may be greater than 99%.

The effluent from the second hydrocyanation reaction zone 60 comprises adiponitrile, third catalyst, catalyst promoter and catalyst degradation product. In FIG. 6, this reaction effluent from the second hydrocyanation reaction zone 60 passes through line 64 to liquid/liquid extraction zone 65. One or more stages of distillation (not illustrated) may be included between the second hydrocyanation reaction zone 60 and liquid/liquid extraction zone 65 to remove lower-boiling constituents, Including unreacted 3-pentenenitrile. The 2PN/3PN ratio in the column bottoms may be controlled to reduce the amount of isomerization of 3PN to 2M3BN. Extraction solvent is fed into extraction zone 65 through line 70. In extraction zone 65 there is formed an extract phase and a raffinate phase. The extract phase comprises the extraction solvent and catalyst, and the raffinate phase comprises adiponitrile, catalyst degradation products and promoter. The extract phase passes through line 67 to distillation zone 68, where extraction solvent is separated from the catalyst. The extraction solvent from distillation zone 68 passes through line 69 and is recycled back into extraction zone 65. A catalyst stream is taken from distillation zone 68 and is recycled back into the second hydrocyanation reaction zone 60. The raffinate phase is taken from extraction zone 65 through line 66 into an adiponitrile purification section. A purified adiponitrile product stream is recovered from the adiponitrile purification section.

The reaction product mixture from the 3PN hydrocyanation reaction zone, including pentenenitriles, such as 3PN, 2PN, and (E)-2M2BN; dinitriles, such as ADN and MGN; catalyst; catalyst degradation products and promoter, may be contacted with a non-polar hydrocarbon extraction solvent in an extraction zone according to a method described in U.S. Pat. Nos. 3,773,809 and 6,936,171. An extract stream including catalyst and extraction solvent and a raffinate stream including extraction solvent, pentenenitriles, dinitriles, catalyst degradation products, and promoter are withdrawn from the extraction zone. The extract stream may be charged to a distillation apparatus.

The extract stream is distilled to obtain a first extraction solvent-enriched stream and a catalyst-enriched stream including the recovered catalyst. The catalyst-enriched stream including nickel complexes of the phosphorus-containing ligand may be recycled to contact 3PN and HC≡N in the presence of the promoter to produce ADN.

The raffinate stream may be distilled in one or more distillation columns to obtain a second extraction solvent-enriched stream, a pentenenitrile-enriched stream including 3PN, a dinitrile-enriched stream, a dinitrile-depleted stream including the catalyst degradation products and promoter, a MGN-enriched stream, and a MGN-depleted stream including the recovered ADN.

Extraction solvent from the first and second extraction solvent-enriched streams may be reused in the extraction zone. Pentenenitrile from the pentenenitrile-enriched stream may be used as a solvent source for preparing catalyst for use in the first hydrocyanation reaction zone 4, the isomerization reaction zone 40 or the second hydrocyanation reaction zone 60. 3PN may also be separated from the pentenenitrile-enriched stream and may contact catalyst and HC≡N In the presence of the promoter to produce ADN, provided that the 3PN is sufficiently free of $C_8H_{13}C≡N$ compounds or compounds, such as phenol or cresols, which are capable of reacting with the phosphorus-containing ligand used in the catalyst for reacting 3PN with HC≡N.

The extract stream may be distilled in at least one distillation column at 1 psia to 22 psia (0.07 bar to 1.5 bar) pressure and with a base temperature of less than about 150° C., for example, less than about 140° C., for example, less than about 130° C., or, for example, less than about 120° C. The base temperature is chosen in part to maintain the thermal stability of the catalyst composition. The 2PN/3PN ratio in the column bottoms may be controlled to reduce the amount of isomerization of 3PN to 2M3BN.

Distillation steps for treatment of the raffinate phase are shown in FIG. 7, as described above.

Although a majority of the extraction solvent separates into the solvent phase in the extraction zone, some extraction solvent is extracted into the raffinate phase. The raffinate stream, therefore, comprises some extraction solvent. The raffinate stream may further comprise one or more of at least one pentenenitrile (typically a mixture of pentenenitriles), intermediate boilers and dinitriles comprising adiponitrile (ADN) and methylglutaronitrile (MGN). In a first distillation step of the raffinate stream, extraction solvent having a lower boiling point than pentenenitriles may be separated from other higher boiling constituents of the raffinate stream to obtain an extraction solvent-depleted raffinate stream. The extraction solvent may have a boiling point of, for example, from 30 to 135° C., for example, from 60 to 100° C. An example of such an extraction solvent is cyclohexane, which has a boiling point (BP) of 81° C.

In a second distillation step of the raffinate stream, pentenenitrile may be removed from other higher boiling components of the raffinate stream to obtain a pentenenitrile-depleted raffinate stream. In FIG. 7, this pentenenitrile-depleted raffinate stream 83 is obtained by distilling an extraction solvent-depleted stream in distillation column 80. This pentenenitrile-depleted raffinate stream 83 may comprise, for example, a total of at least 0.01% by weight of pentenenitrile including the sum of 4-pentenenitrile, 3-pentenenitrile, and 2-pentenenitrile. Examples of pentenenitriles, which may be removed as an overhead stream 82 in this second distillation step include 2-methyl-3-butenenitrile, trans-3-pentenenitrile, cis-3-pentenenitrile, trans-2-pentenenitrile, and cis-2-pentenenitrile. This pentenenitrile-depleted raffinate stream may comprise, for example, a total of at least 0.01%, for example, 0.07%, for example 0.1%, for example, less than 1%, by weight of pentenenitrile including the sum of 4-pentenenitrile, 3-pentenenitrile, and 2-pentenenitrile. Such removed pentenenitriles may have an approximate boiling point within the range of from 120° C. to 150° C.

The pentenenitrile-depleted raffinate stream 83 obtained in the above-mentioned second distillation step may be introduced into at least one or more additional distillation steps. In FIG. 7, a third distillation step takes place column 84. In this third distillation step, compositions having a higher boiling point than dinitriles are separated as a bottom stream 86 from dinitriles and any coboilers present, such as intermediate boilers. Such bottoms products in stream 86 may have a boiling point of, for example, at least 300° C. In contrast, most dinitriles in the pentenenitrile-depleted raffinate stream 83 would tend to have a boiling point within the approximate range of 260° C. to 300° C. These dinitriles and intermediate boilers tend to be withdrawn as an overhead draw through stream 85.

In FIG. 7, stream 85 may then be passed to distillation column 87 to produce adiponitrile as a bottoms stream 89 and an overhead stream 88 comprising MGN and intermediate boilers.

Stream 86 comprising catalyst degradation products from column 84 may passed to a wiped film evaporator (WFE) to recover adiponitrile in such bottoms. One or more streams comprising catalyst degradation byproducts, which are obtained from distillation of raffinates obtained by liquid/liquid extraction of effluents from the first hydrocyanation reaction zone 4, the isomerization reaction zone 40, may also, optionally, be passed to this wiped film evaporator.

Although particular distillation steps are described above for converting the raffinate stream from the extraction zone into a purified adiponitrile stream, it will be understood that other distillation steps are possible. It is within the ordinary skill in the art to design and operate such steps. Streams of compounds removed from the adiponitrile in the raffinate may be disposed of, further refined, used in a different reaction process or recycled to an appropriate point in the overall reaction system.

The adiponitrile chemical yield from 1,3-butadiene may be greater than 60%, for example, greater than 85% or greater than 90%, and the adiponitrile chemical yield from hydrogen cyanide may be greater than 60%, for example, greater than 85% or greater than 90%.

By limiting the amount of $C_9$ mononitriles entering into the second hydrocyanation reaction zone 60, the amount of dinitriles of the formula $C_8H_{14}(C≡N)_2$, produced in the second hydrocyanation reaction zone 60 may be limited. For example, the reaction product from the second hydrocyanation reaction zone 60 may comprise substantially a dinitrile product comprising adiponitrile (ADN) and having less than 5000 parts per million (ppm); preferably less than 2000 parts per million (ppm); most preferably less 500 parts per million (ppm) dinitriles (DDN) of chemical formula $C_8H_{14}(C≡N)_2$.

The zones described herein where catalyst is partially purified by removal of catalyst degradation products and reaction byproducts are referred to herein as purification zones or regeneration zones. When the phosphorus-containing ligands of the catalysts, which are used for the first hydrogenation reaction zone 4 and the isomerization reaction zone 40 are identical, the regeneration zones for treating these catalysts may be combined (co-mingled) as a shared catalyst regeneration zone comprising liquid-liquid extraction. This option further comprises feeding at least a portion of the first hydrocyanation catalyst from the first hydrocyanation catalyst purge 9, feeding at least a portion of the isomerization catalyst from the isomerization catalyst purge 47 or feeding a combination thereof to the shared catalyst regeneration zone to at least partially separate catalyst degradation product and reaction byproduct from a separated catalyst.

At least a portion of the separated catalyst from the shared catalyst regeneration zone may be contacted with 1,3-butadiene and hydrogen cyanide in the first hydrocyanation reaction zone 4 to produce the first hydrocyanation reaction effluent 5.

At least a portion of the separated catalyst from the shared catalyst regeneration zone may be contacted with 2-methyl-3-butenenitrile in the isomerization reaction zone 40 to produce the isomerization reaction effluent 43.

Catalyst from the shared catalyst regeneration zone may be contacted with both 1,3-butadiene and hydrogen cyanide in the first hydrocyanation reaction zone 4 and with 2-methyl-3-butenenitrile in the isomerization reaction zone 40.

The optional shared catalyst regeneration zone for the catalysts is generally not used when the ligands of the catalysts are different.

As used herein, the term "catalyst" Includes within its meaning a catalyst precursor composition. This meaning Indicates that the zero-valent nickel at some point becomes bound to at least one phosphorus-containing ligand. Furthermore, additional reactions occur during hydrocyanation, e.g., complexing of the initial catalyst composition to an ethylenically unsaturated compound. As used herein, the term "catalyst" also includes within its meaning recycled catalyst, that is, a catalyst comprising a zero-valent nickel and at least one phosphorus-containing ligand which, having been used in the process of the invention, is returned or may be returned to the process and used again or used repeatedly. Suitable solvents for the catalysts include extraction solvents useful in the process, for example, polar solvents such as nitriles, for example, pentenenitriles such as 3-pentenenitrile, and non-polar solvents such as aliphatic hydrocarbons, for example, cyclohexane.

The catalysts, which are used in reactions zones 4, 40, and 60, each comprise zero valent nickel and a phosphorus-containing ligand. These catalysts may be the same or different. Optionally, each of the catalysts are different. Optionally, the first hydrocyanation catalyst and the isomerization catalyst are the same, and the second hydrocyanation catalyst is different. Optionally, the isomerization catalyst and the second hydrocyanation catalyst are the same, and the first hydrogenation catalyst is different. Optionally, the first hydrocyanation catalyst and the isomerization catalyst comprise the same or different monodentate ligand, and the second hydrocyanation catalyst comprises a bidentate ligand. Optionally, the first hydrocyanation catalyst comprises a monodentate ligand, and the isomerization catalyst and the second hydrocyanation catalyst comprise the same or different bidentate ligand.

The chemical yield of adiponitrile may be increased from the reaction of 1,3-butadiene and hydrogen cyanide over what can be achieved when the first hydrocyanation catalyst, the isomerization catalyst, and the second hydrocyanation catalyst are the same with respect to the phosphorus-containing ligand and the same catalyst flows into these reaction zones 4, 40 and 60.

The first hydrocyanation catalyst for reacting BD with HC≡N may comprise, for example, zero-valent Ni and at least one monodentate phosphorus-containing ligand. Also, the second hydrocyanation catalyst for reacting 3PN with HC≡N may be segregated from the first hydrocyanation reaction zone 4 and the isomerization reaction zone 40. Further, the steps for purifying the first hydrocyanation catalyst and the second hydrocyanation catalyst are preferably segregated, at least to the extent to avoid a mixture of the first hydrocyanation catalyst and the second hydrocyanation catalyst from being introduced into a reaction zone.

The second hydrocyanation catalyst may be segregated from the first hydrocyanation reaction zone 4 and the isomerization reaction zone 40 by not recycling the second hydrocyanation catalyst back (either directly or indirectly) to the first hydrocyanation reaction zone 4 and the isomerization reaction zone 40, or indeed to any location upstream of the isomerization reaction zone 40 or streams thereto.

When the ligand of the first hydrocyanation catalyst and the isomerization catalyst is a monodentate ligand and the ligand of the second hydrocyanation catalyst is a bidentate ligand, the second hydrocyanation catalyst may be segregated from the first hydrocyanation reaction zone 4 and the isomerization reaction zone 40. By segregating the second hydrocyanation catalyst from the first hydrocyanation reaction zone 4 and the isomerization reaction zone 40, the concentration of the phosphorus-containing multidentate ligand from the second hydrocyanation catalyst in either the first hydrocyanation reaction zone 4 or the isomerization reaction zone 40 may be no more than 100 ppm, for example, no more than 50 ppm, for example, no more than 10 ppm, for example, no more than 5 ppm, for example, no more than 1 ppm, and for example, substantially zero.

Although small amounts (e.g., traces) of the first hydrocyanation catalyst may be present in the feed stream 61 to the second hydrocyanation reaction zone 60, the first hydrogenation catalyst is preferably not intentionally introduced to the second hydrocyanation reaction zone 60. In general, at least 90%, for example, at least 95%, for example, at least 99%, for example, at least 99.9% and suitably, substantially all of the first hydrocyanation catalyst is recycled to at least one of the first hydrocyanation reaction zone 4 and the isomerization reaction zone 40, and/or less than 10%, for example, less than 5%, for example, less than 1%, for example, less than 0.1%, and suitably none of the first hydrocyanation catalyst is introduced to the second hydrocyanation reaction zone 60.

Nevertheless, some of the first hydrocyanation catalyst may be passed in tolerable amounts downstream to the second hydrocyanation reaction zone 60, although this is normally achieved by routes other than passing a purified stream of first hydrocyanation catalyst to the second hydrocyanation reaction zone 60, as will be appreciated from the process descriptions herein. For example, some of the first hydrocyanation catalyst may unintentionally pass into the second hydrocyanation reaction zone 60 as a result of a unit upset or operator error without the need to shut down the entire integrated process and remove first hydrocyanation catalyst from the second hydrocyanation reaction zone 60.

When the ligand of the first hydrocyanation catalyst is a monodentate ligand and the ligand of the second hydrocyanation catalyst is a bidentate ligand, the concentration of the phosphorus-containing monodentate ligand of the first hydrocyanation catalyst in the second hydrocyanation reaction zone 60 may be no more than 500 ppm, preferably no more than 100 ppm, preferably no more than 50 ppm, preferably no more than 10 ppm, preferably no more than 5 ppm, preferably no more than 1 ppm, and preferably substantially zero.

The reaction of nickel metal with at least one free phosphorus-containing ligand is taught in U.S. Pat. Nos. 3,903,120, 4,385,007, 4,416,825; United States Patent Application Publication No. 20040176622, and PCT Patent Application Publication No. 1995011077, Incorporated herein by reference.

Catalyst compositions comprising at least one phosphorus-containing ligand may be substantially free and maintained separate from at least one of carbon monoxide, oxygen, and water. These catalyst compositions may be preformed or prepared in situ according to techniques well known in the art. For example, the catalyst composition may be formed by contacting a monodentate or bidentate phosphite ligand with a zero-valent nickel compound having ligands easily displaced by organophosphite ligands, such as $Ni(COD)_2$, $Ni[P(O\text{-}o\text{-}C_6H_4CH_3)_3]_3$, and $Ni[P(O\text{-}o\text{-}C_6H_4CH_3)_3]_2(C_2H_4)$, all of which are well known in the art, wherein 1,5-cyclooctadiene (COD), tris(ortho-tolyl)phosphite $[P(O\text{-}o\text{-}C_6H_4CH_3)_3]$, and ethylene $(C_2H_4)$ are the easily displaced ligands, where the lower case "o" represents ortho. Elemental nickel, preferably nickel powder, when combined with a halogenated catalyst, as described in U.S. Pat. No. 3,903,120; is also a suitable source of zero-valent nickel.

Alternatively, divalent nickel compounds can be combined with a reducing agent, to serve as a source of zero-valent nickel in the reaction, in the presence of a monodentate or bidentate phosphite ligands. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn, Fe or $H_2$ and electrochemical means known from the art. See, for example, U.S. Pat. No. 6,893,996, which is incorporated herein by reference. In a catalyst composition, the bidentate phosphite ligand may be present in excess of what can theoretically be coordinated to the nickel at a given time.

When a divalent nickel compound is reacted with a reducing agent, a Lewis acid may be generated as a byproduct. For example, when $NiCl_2$ is reacted with zero valent Zn in the presence of a ligand, there is formed a catalyst comprising zero valent Ni and $ZnCl_2$, which is a Lewis acid. It is possible to use such a reaction product as a feed of both catalyst and Lewis acid to the second hydrocyanation reaction zone 60.

However, this reaction product should be subjected to an appropriate purification step to remove Lewis acid before the catalyst is used as a feed to the first hydrocyanation reaction zone 4. Such a purification step may Involve liquid/liquid extraction and distillation. It is preferred to use zero valent Ni, instead of divalent Ni, as the nickel source for the first hydrocyanation catalyst.

Suitable methods for preparing catalysts, which may be used as the first, second or third catalyst, are described in WO 2012/033556 A1.

The catalyst composition may be dissolved in a solvent non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, 2PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst composition.

As discussed herein above, catalyst may be regenerated by liquid/liquid extraction followed by distillation to remove extraction solvent. The concentration of nickel complexes in the catalyst, recovered in this distillation step, may be increased prior to contacting at least a portion of the concentrated nickel complexes, comprising zero-valent nickel and at least one phosphorus-containing ligand, with 1,3-butadiene and hydrogen cyanide in the first hydrocyanation reaction zone 4 to produce the first hydrocyanation reaction effluent 5; and with 2-methyl-3-butenenitrile in the isomerization reaction zone 40 to produce the isomerization reaction effluent 43; or their combination. The concentration of nickel complexes may be increased by contacting at least a portion of the extraction solvent-depleted stream with nickel metal in an organonitrile solvent.

The catalysts used in the process of the invention include zero-valent nickel and at least one phosphorus-containing (P-containing) ligand, such as a phosphite, a phosphonite, a phosphinite, a phosphine, and a mixed P-containing ligand or a combination of such members.

The P-containing ligands chemically bond to nickel as complexes comprising zero-valent nickel, and the free P-containing ligands not bonded to the complexes, may be monodentate or multidentate, for example, bidentate or tridentate. The term "bidentate" is well known in the art and means both phosphorus atoms of the ligand may be bonded to a single metal atom. The term "tridentate" means the three phosphorus atoms on the ligand may be bonded to a single metal atom. The terms "bidentate" and "tridentate" are also known in the art as chelate ligands.

As used herein, the term "mixed P-containing ligand" means a P-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

At least one of the catalysts selected from the group of the first hydrocyanation catalyst, the isomerization catalyst, and the second hydrocyanation catalyst may be different with respect to at least one phosphorus-containing ligand.

Examples of phosphorus-containing ligands for the first hydrocyanation catalyst are selected from the group consisting of compounds of Formula II, Formula III, Formula IV, Formula IVa or combinations thereof. Examples of suitable phosphorus-containing ligands for the isomerization catalyst, are selected from the group consisting of compounds of Formula II, Formula III, Formula IV, Formula IVa or combinations thereof. Examples of suitable phosphorous-containing ligands for the second hydrocyanation catalyst are selected from the group consisting of compounds of Formula II, Formula III, Formula IV, Formula IVa or combinations thereof.

Formula II has the structure,

$$P(OR^2)(OR^3)(OR^4) \tag{II}$$

where $R^2$, $R^3$ and $R^4$ are the same or different and are aryl groups, for example, phenyl and tolyl groups, where the aryl or phenyl groups are each optionally substituted with up to four alkyl groups, each alkyl group having from 1-4 carbon atoms.

Formula III has the structure,

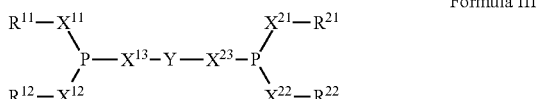

wherein, $X^{11}$, $X^{12}$, $X^{13}$, $X^{21}$, $X^{22}$, $X^{23}$ independently represent oxygen or a single bond;

$R^{11}$, $R^{12}$ independently represent identical or different, single or bridged organic radicals;

$R^{21}$, $R^{22}$ independently represent identical or different, single or bridged organic radicals; and Y represents a bridging group.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups. In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite. In another preferred embodiment, $X^{13}$ may be oxygen and $X^{11}$ and $X^{12}$ each a single bond, or $X^{1}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite. In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine. The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol). The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups. The $R^1$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

Formula IV has the structure, $$P(X^1R^1)(X^2R^2)(X^3R^3) \quad \text{Formula IV}$$

wherein, $X^1$, $X^2$, $X^3$ independently represent oxygen or a single bond; and $R^1$, $R^2$ and $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly. In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups. In another preferred embodiment, a maximum of two of the $R^1$, $R^2$ and $R^3$ groups should be o-tolyl groups. Particularly preferred compounds which may be used are those of the formula (IVa) below:

(o-tolyl-O-)$_w$(m-tolyl-O-)$_x$(p-tolyl-O-)$_y$(phenyl-O-)$_z$P  Formula (IVa)

where w, x, y and z are each a natural number and the following conditions apply: w+x+y+z=3 and w, z<=2.

Examples of such compounds (IIa) are (o-tolyl-O—)$_3$P, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

An example of a bidentate phosphite ligand that is useful in the present process is that having the Formula V, shown below

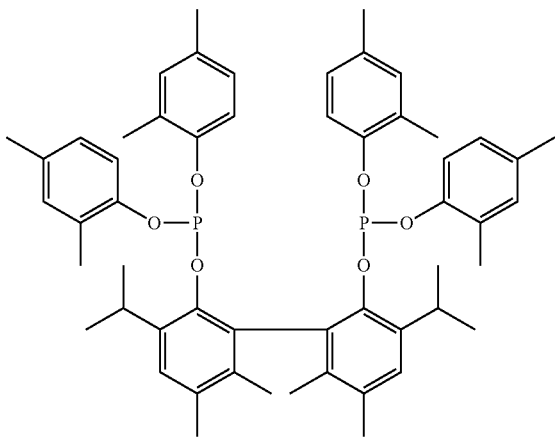

Further examples of bidentate phosphite ligands that are useful in the present process include those having the Formulae VI to IX, shown below wherein for each formula, $R^{17}$ is selected from the group consisting of methyl, ethyl or iso-propyl, and $R^{18}$ and $R^{19}$ are independently selected from H or methyl:

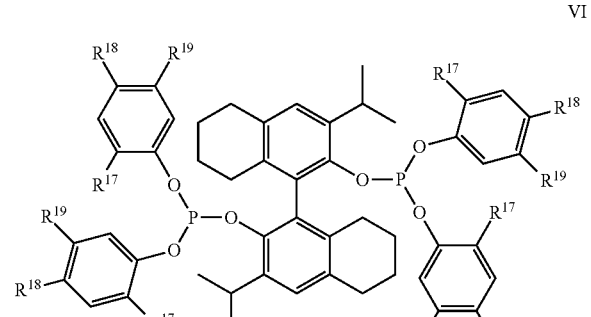

VI

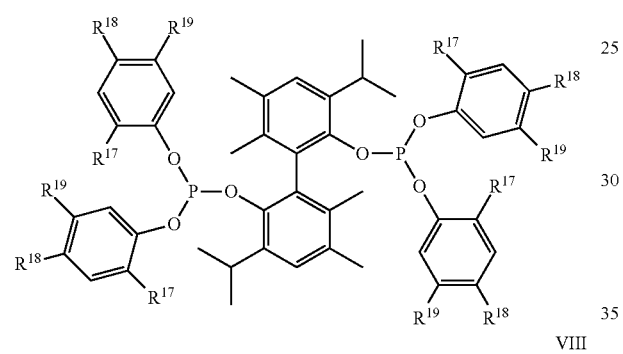

VII

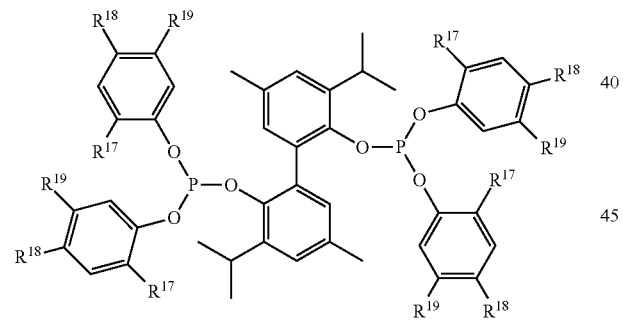

VIII

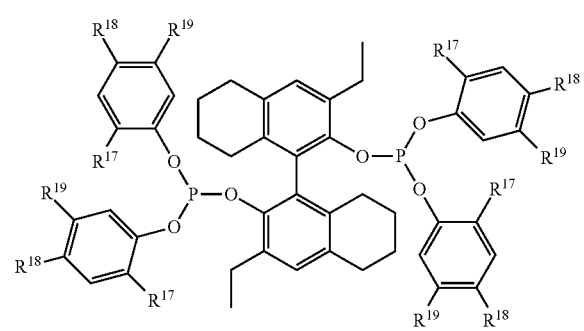

IX

Additional examples of bidentate phosphite ligands that are useful in the present process include a ligand selected from a member of the group represented by Formulae X and XI, in which all like reference characters have the same meaning, except as further explicitly limited:

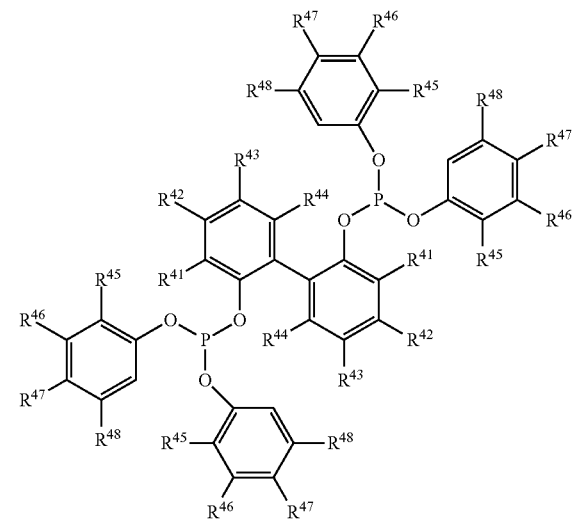

Formula X

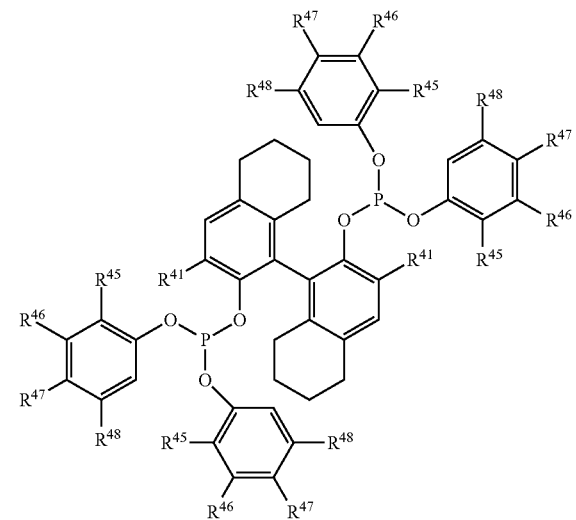

Formula XI wherein, $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

For example, the bidentate phosphite ligand can be selected from a member of the group represented by Formula X and Formula XI, wherein $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula X, wherein $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;
or
$R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
or the bidentate phosphite ligand can be selected from a member of the group represented by Formula XI, wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula X, wherein $R^{4'}$ is isopropyl; $R^{42}$, $R^{46}$, and $R^{48}$ are H; and $R^{43}$, $R^{44}$, $R^{45}$, and $R^{47}$ are methyl.

It will be recognized that Formulae V to XI are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydro-binaphthyl, and or binaphthyl bridging groups of Formulae V to XI, respectively, can bring the two phosphorus atoms of each Formula in closer proximity to one another and can allow the phosphite ligand to bind to nickel in a bidentate fashion.

The term "bidentate" is well known in the art and means both phosphorus atoms of the ligand are bonded to a single nickel atom.

At least one phosphorus-containing ligand for the first hydrocyanation catalyst may be, for example, selected from the group consisting of compounds of Formula IV, wherein Formula IV has the structure above.

At least one phosphorus-containing ligand for the isomerization catalyst may be, for example, selected from the group consisting of compounds of Formulae III and IV, wherein Formulae III and IV have the structure above.

At least one phosphorus-containing ligand for the second hydrocyanation catalyst may be selected from the group consisting of compounds of Formula III, wherein Formula III has the structure above.

The reaction, which takes place in the second hydrocyanation reaction zone 60 for hydrocyanating 3-pentenenitrile to produce adiponitrile, preferably takes place in the presence of a promoter for promoting this reaction. The promoter may be a Lewis acid, such as an Inorganic compound, an organometallic compound, or combinations thereof, in which a cation of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. However, the reactions, which take place in the first hydrocyanation reaction zone 4 for hydrocyanating 1,3-butadiene and the isomerization reaction zone 40 for isomerizing 2-methyl-3-butenenitrile, preferably take place in the absence or substantial absence of such a promoter. It will be understood that the expression, substantial absence, allows for some measureable promoter to be present, provided that the amount of the promoter is not sufficient to significantly impact the selectivity or yield of the reactions taking place in the first hydrocyanation reaction zone 4 and the isomerization reaction zone 40.

Dinitriles may be produced in the first hydrocyanation reaction zone 4 by the reaction of 3PN or 2M3BN with HCN. Lewis acids are capable of promoting the formation of dinitriles in the first hydrocyanation reaction zone 4. Lewis acids are preferably not introduced into the first reaction zone in detectable amounts. However, a detectable amount of a Lewis acid may be introduced into the first hydrocyanation reaction zone 4, provided that dinitrile formation is minimized. For example, a detectable amount of a Lewis acid may be introduced into the first reaction zone, provided that the amount of dinitriles produced, when none of the Lewis acid is Introduced into the first reaction zone, is not increased by more than 5 wt %.

Lewis acid may be unintentionally introduced into the first hydrocyanation reaction zone 4 as a result of a unit upset or operator error. However, the continuous production of 3-pentenenitrile may be maintained, provided that the ratio of atomic equivalents of Ni to moles of Lewis Acid in the first hydrocyanation reaction zone 4 is less than 10:1 during the course of at least 95% of the production of 3-pentenenitrile.

3-pentenenitrile produced in the first hydrocyanation reaction zone 4 and the isomerization reaction zone 40 may be reacted with hydrogen cyanide to produce dinitriles comprising adiponitrile in a second hydrocyanation reaction zone 60 downstream of the first hydrocyanation reaction zone 4 and the isomerization reaction zone 40. A catalyst and a Lewis acid promoter may flow through the second hydrocyanation reaction zone 60 along with reactants and products. Preferably, none of the Lewis acid promoter which flows from the second hydrocyanation reaction zone 60 flows into the first hydrocyanation reaction zone 4. However, it is possible that a portion of the Lewis acid promoter which flows from the second hydrocyanation reaction zone 60 flows into the first hydrocyanation reaction zone 4, provided that the unwanted production of dinitriles in the first hydrocyanation reaction is minimized, as discussed above.

Distillation steps described herein may be performed in any suitable equipment known to one skilled in the art. Examples of conventional equipment suitable for this distillation include sieve tray columns, bubble tray columns, columns with regular packing, random packed columns or single-stage evaporators, such as falling film evaporators, thin-film evaporators, flash distillation evaporators, multi-phase helical coil evaporators, natural circulation evaporators or forced circulation flash evaporators. The distillation can be performed in one or more pieces of equipment.

Distillation equipment may comprise at least one distillation column. A distillation column may be provided with a structured packing section above the feed location to prevent catalyst entrainment in the distillate and to generate an appropriate separation.

The examples which follow demonstrate the present invention and its capability for use. These examples are regarded as illustrative in nature and not restrictive.

EXAMPLE 1

Use of Cis-2-Pentenenitrile in Simulated Distillation

Four reaction mixtures of pentenenitriles and hydrocyanation catalyst were prepared to simulate the composition of distillation column bottoms in a distillation column for separating extraction solvent from a catalyst extracted into the solvent. The catalyst was a complex of zero valent nickel with a bidentate phosphite ligand of the formula:

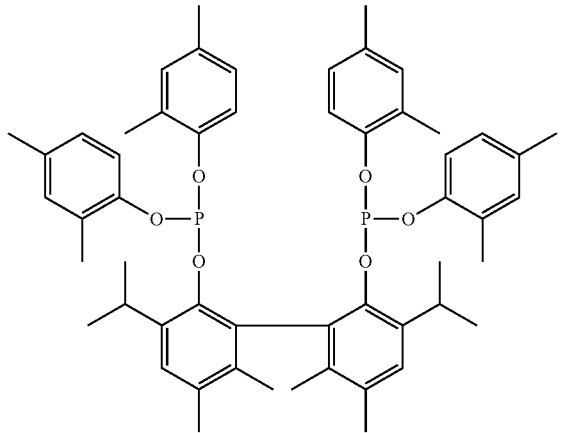

Each reaction mixture included ~51 wt % trans-3-pentenenitrile, 0.4 wt % 2-methyl-3-butenenitrile and 575 ppm nickel. The weight ratio of nickel to bidentate phosphite ligand was 0.017.

Varying amounts of cis-2-pentenenitrile were included in each reaction mixture. A first reaction mixture included an amount of cis-2-pentenenitrile to provide a ratio of trans-3-pentenenitrile to cis-2-pentenenitrile (T3PN/C2PN) of 3. A second reaction mixture Included an amount of cis-2-pentenenitrile to provide a ratio of trans-3-pentenenitrile to cis-2-pentenenitrile (T3PN/C2PN) of 7. A third reaction mixture included an amount of cis-2-pentenenitrile to provide a ratio of trans-3-pentenenitrile to cis-2-pentenenitrile (T3PN/C2PN) of 14. A fourth reaction mixture included an amount of cis-2-pentenenitrile to provide a ratio of trans-3-pentenenitrile to cis-2-pentenenitrile (T3PN/C2PN) of 40.

An appropriate amount of valeronitrile was added as a diluent to the second, third and fourth reaction mixtures to maintain the concentration of ~51 wt % trans-3-pentenenitrile, 0.4 wt % 2-methyl-3-butenenitrile and 575 ppm nickel in each reaction mixture.

Figure 8:
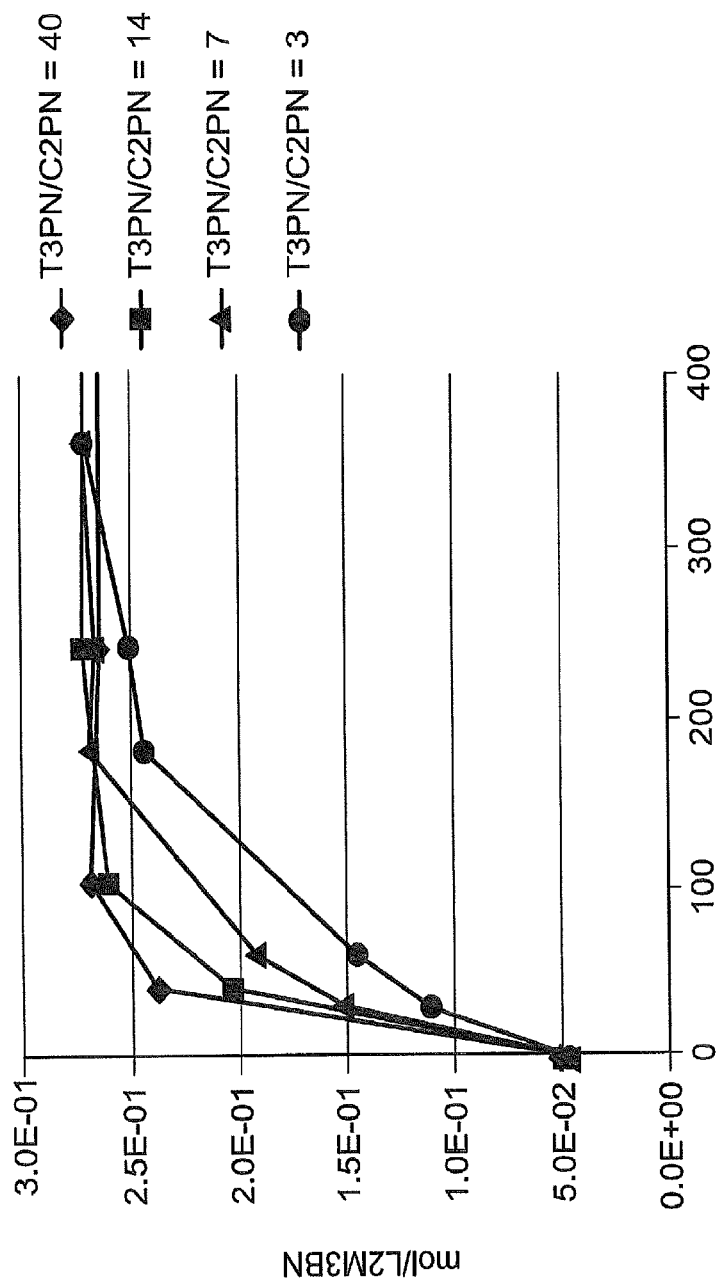
FIG. 8 is a graph illustrating the affect of cis-2-pentenenitrile on the isomerization of 3-pentenenitrile to 2-methyl-3-butenenitrile in the presence of a catalyst under various simulated distillation conditions.

Each of the reaction mixtures was heated to 108° C., and the concentration of moles of 2-methyl-3-butenenitrile per liter of the mixture (mol/L 2M3BN) was measured periodically. Results are shown in FIG. 8. These results show that 3PN was isomerized over time with a 3PN/2M3BN equilibrium being reached within approximately 3 to 4 hours in all cases studied. However, the addition of cis-2-pentenenitrile was effective in suppressing isomerization of 3PN to 2M3BN at shorter heating conditions, for example, 2 hours or less.

EXAMPLE 2

Use of Trans-2-Pentenenitrile in Simulated Distillation

Example 1 was repeated except that trans-2-pentenenitrile was substituted for cis-2-pentenenitrile and at least some of the ratios of trans-3-pentenenitrile to 2-pentenenitrile were changed. In particular, a first reaction mixture included an amount of trans-2-pentenenitrile to provide a ratio of trans-3-pentenenitrile to trans-2-pentenenitrile (T3PN/T2PN) of 2.6. A second reaction mixture included an amount of trans-2-pentenenitrile to provide a ratio of trans-3-pentenenitrile to trans-2-pentenenitrile (T3PN/T2PN) of 4.5. A third reaction mixture included an amount of trans-2-pentenenitrile to provide a ratio of trans-3-pentenenitrile to trans-2-pentenenitrile (T3PN/T2PN) of 7. A fourth reaction mixture included an amount of trans-2-pentenenitrile to provide a ratio of trans-3-pentenenitrile to trans-2-pentenenitrile (T3PN/T2PN) of 15.

As with the procedure for Example 1, valeronitrile was used as a diluent for the second, third and fourth reaction mixtures.

Figure 9:
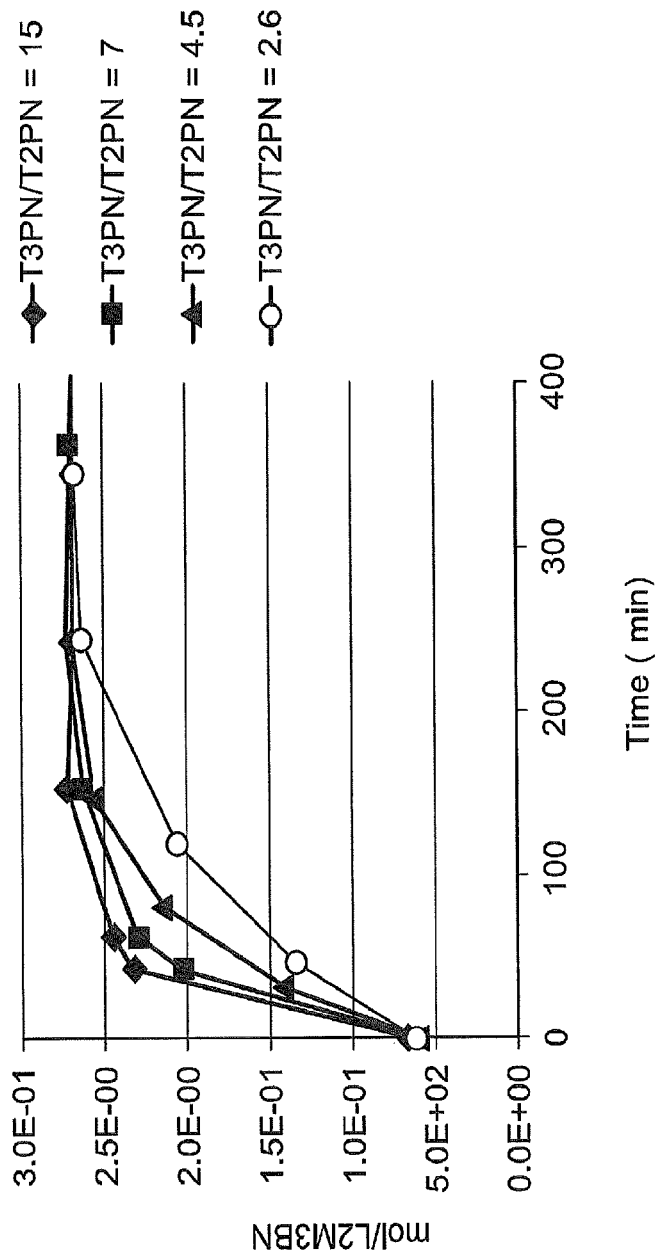
FIG. 9 is a graph illustrating the affect of trans-2-pentenenitrile on the isomerization of 3-pentenenitrile to 2-methyl-3-butenenitrile in the presence of a catalyst under various simulated distillation conditions.

As with the procedure for Example 1, each of the reaction mixtures was heated to 108° C., and the concentration of moles of 2-methyl-3-butenenitrile per liter of the mixture (mol/L 2M3BN) was measured periodically. Results are shown in FIG. 9. These results show that trans-2-pentenenitrile was effective in suppressing isomerization of 3PN to 2M3BN, but slightly less so than cis-pentenenitrile. Without being bound by any theory for explaining this difference, it is believed that trans-2-pentenenitrile is a more labile ligand cis-2-pentenenitrile, when bound to the nickel/phosphite ligand complex of the catalyst.

COMPARATIVE EXAMPLE 3

Use of E2-Methyl-2-Butenenitrie in Simulated Distillation

Example 1 was repeated except that cis-2-methyl-2-butenenitrile (i.e. E-2-methyl-2-butenenitrile or E2M2BN, i.e. the higher boiling isomer of 2-methyl-2-butenenitrile) was substituted for cis-2-pentenenitrile and the ratio of trans-3-pentenenitrile to E-2-methyl-2-butenenitrile was generally higher. In particular, a first reaction mixture included an amount of E-2-methyl-2-butenenitrile to provide a ratio of trans-3-pentenenitrile to E-2-methyl-2-butenenitrile (T3PN/E2M2BN) of 1.9. A second reaction mixture included an amount of E-2-methyl-2-butenenitrile to provide a ratio of trans-3-pentenenitrile to E-2-methyl-2-butenenitrile (T3PN/E2M2BN) of 2.8. A third reaction mixture included an amount of E-2-methyl-2-butenenitrile to provide a ratio of trans-3-pentenenitrile to E-2-methyl-2-butenenitrile (T3PN/E2M2BN) of 3.9. A fourth reaction mixture included an amount of E-2-methyl-2-butenenitrile to provide a ratio of trans-3-pentenenitrile to E-2-methyl-2-butenenitrile (T3PN/E2M2BN) of 5.6.

As with the procedure for Example 1, valeronitrile was used as a diluent for the second, third and fourth reaction mixtures.

Figure 10:
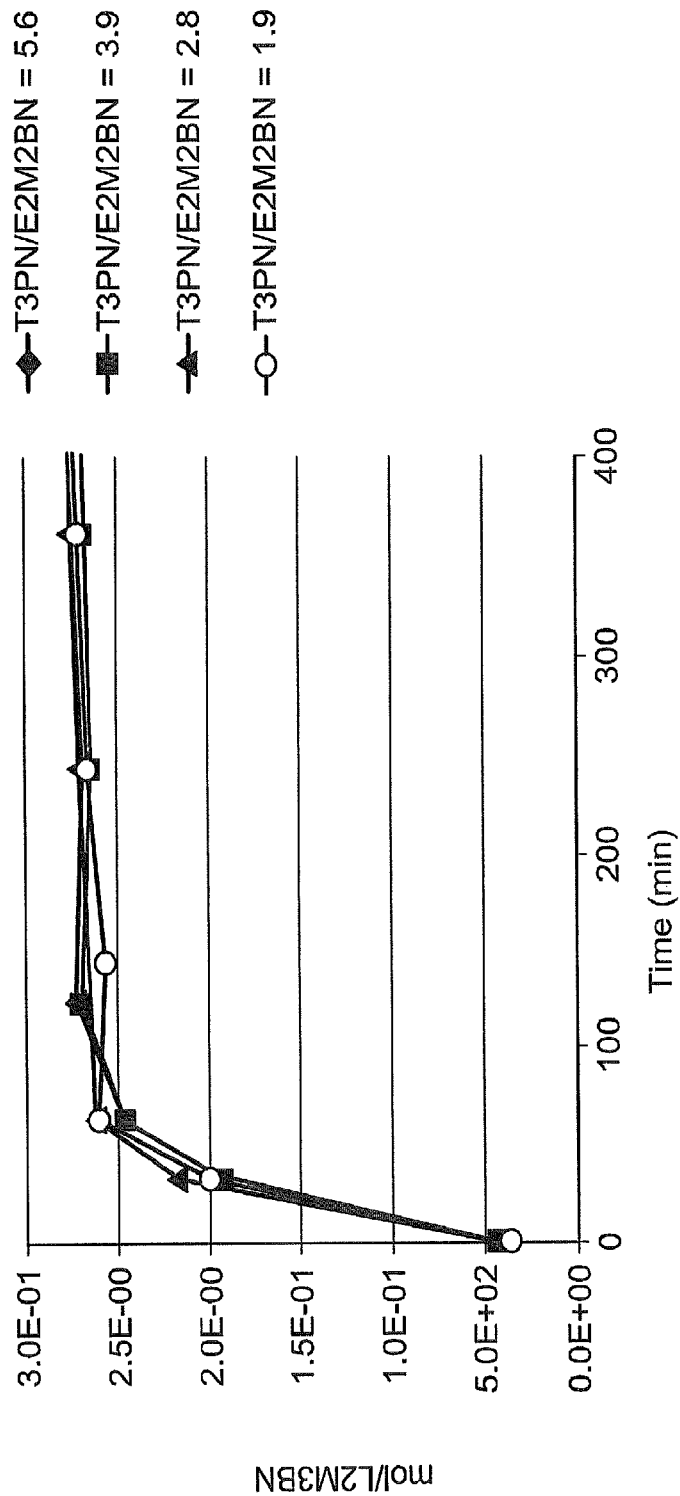
FIG. 10 is a graph illustrating the affect of trans-2-methyl-2-butenenitrile on the isomerization of 3-pentenenitrile to 2-methyl-3-butenenitrile in the presence of a catalyst under various simulated distillation conditions.

As with the procedure for Example 1, each of the reaction mixtures was heated to 108° C., and the concentration of moles of 2-methyl-3-butenenitrile per liter of the mixture (mol/L 2M3BN) was measured periodically. Results are shown in FIG. 10. These results show that E-2-methyl-2-butenenitrile was not effective in suppressing isomerization of 3PN to 2M3BN.

EXAMPLE 4

Suppression of 2M3BN Formation in a Distillation Column

This Example demonstrates suppression of 2M3BN formation in a distillation column during a process for the continuous production adiponitrile.

Hydrogen cyanide, 3-pentenenitrile and a catalyst solution were continuously fed to a hydrocyanation reactor for the continuous production of adiponitrile. The catalyst solution comprised zero valent nickel and a bidentate phosphite ligand of the formula shown in Example 1. The reaction product effluent from the hydrocyanation reactor was then extracted with cyclohexane to form a light phase and a heavy phase.

The light phase comprised cyclohexane, catalyst and a portion of residual pentenenitriles. The heavy phase comprised adiponitrile, a portion of residual pentenenitriles and catalyst degradation products.

The light phase was continuously distilled in a distillation column comprising a re-boiler. The fluids in the re-boiler comprising catalyst, 3PN, and 2PN were maintained at a temperature of 107° C.

To test the effect of the 2PN/3PN ratio on the formation of 2M3BN, additional pentenenitriles were fed to the distillation column. Sources of these additional pentenenitriles included refined pentenenitriles and recycle streams comprising pentenenitriles. The additional pentenenitriles also served to enhance separation of cyclohexane into the overhead stream from the distillation column and to assure that catalyst remained in solution after evaporation of cyclohexane.

Figure 11:
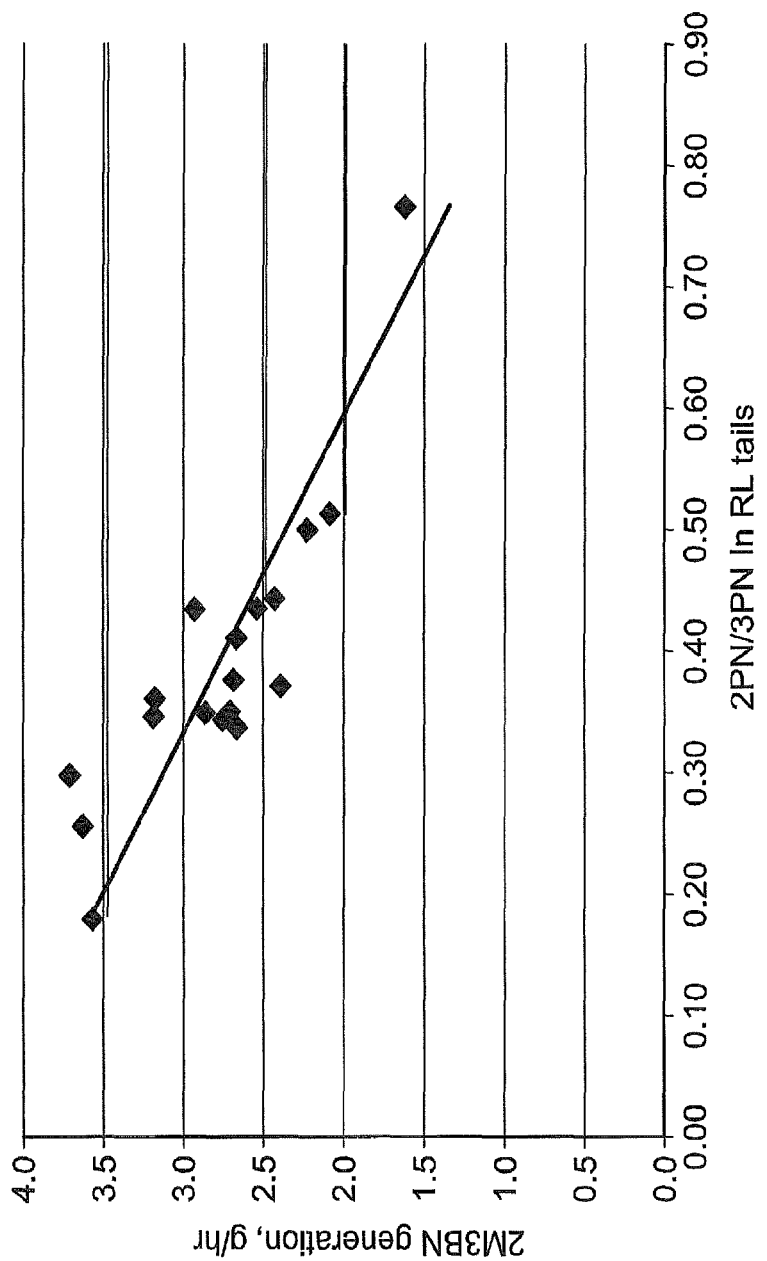
FIG. 11 is a graph illustrating the affect of 2PN/3PN ratio on the production of 2-methyl-3-butenenitrile in a distillation column.

The 2PN/3PN ratio in the overall feed to the distillation column was varied in the approximate range of 0.2 to 0.8. The generation of 2M3BN per hour and other data for various runs are shown in Table I and in FIG. 11.

TABLE 1

| Run # | 2M3BN generation, g/hr | % 2M3BN in distillate | % 2M3BN in tails | 2PN/3PN | 3PN/2M3BN (Distillate + tails) |
|---|---|---|---|---|---|
| 1 | 2.9 ± 0.6 | 60 | 40 | 0.43 ± 0.17 | 14.7 ± 2.9 |
| 2 | 1.6 ± 0.6 | 60 | 40 | 0.77 ± 0.1 | 14.5 ± 3.6 |
| 3 | 3.6 ± 0.5 | 58 | 42 | 0.26 ± 0.07 | 13.9 ± 2.5 |
| 4 | 2.7 ± 0.6 | 58 | 42 | 0.34 ± 0.02 | 15.3 ± 1.9 |
| 5 | 2.9 ± 0.5 | 58 | 42 | 0.35 ± 0.02 | 16.4 ± 3.5 |

2M3BN generation decreased with an increase in 2PN/3PN ratio. For example, 2M3BN generation decreased from 3.6 g/hr to 1.6 g/hr with an increase in 2PN/3PN ratio from 0.26 to 0.77. Therefore, keeping the 2PN/3PN ratio high would decrease the yield loss to 2M3BN.

While the illustrative embodiments of the invention have been described with particularity, it will be understood that the invention is capable of other and different embodiments and that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the invention pertains.

What is claimed is:

1. A method for evaporation of solvent from a catalyst solution comprising solvent and a catalyst, wherein said solvent comprises 2-pentenenitrile (2PN) and 3-pentenenitrile (3PN), wherein said catalyst comprises nickel and a bidentate phosphorus-containing ligand, and wherein said method comprises the steps of:

(a) introducing said catalyst solution into a distillation zone; and
   (b) evaporating solvent in the distillation zone to form a solvent-depleted catalyst solution comprising said catalyst, 2-pentenenitrile and 3-pentenenitrile, while maintaining the 3PN/2PN ratio in said solvent-depleted catalyst solution at 14/1 or less, wherein said catalyst solution, which is introduced into the distillation zone of step (a), is an extracted catalyst solution formed by extracting catalyst from an effluent stream or distilled bottoms fraction of an effluent stream, wherein said effluent stream is the effluent stream from a reactor, and wherein said reactor is selected from the group consisting of (i) a reactor for reacting hydrogen cyanide with 1,3-butadiene in the presence of the catalyst to form 3-pentenenitrile, (ii) a reactor for isomerizing 2-methyl-3-butenenitrile in the presence of the catalyst to form 3-pentenenitrile, and (iii) a reactor for reacting 3-pentenenitrile with hydrogen cyanide in the presence of the catalyst to form adiponitrile, wherein the effluent stream or distilled fraction of the effluent stream is contacted with an extraction solvent comprising one or more linear aliphatic hydrocarbons, one or more branched aliphatic hydrocarbons, one or more unsubstituted cycloaliphatic hydrocarbons, one or more alkyl-substituted cycloaliphatic hydrocarbons, and/or one or more aromatic hydrocarbons, wherein an extraction solvent is a solvent evaporated from said catalyst solution in step (b).

2. The method of claim 1, wherein said catalyst solution, which is introduced into the distillation zone of step (a), is an effluent stream from a reactor for reacting 3-pentenenitrile with hydrogen cyanide in the presence of the catalyst to form adiponitrile, and wherein unreacted 3-pentenenitrile is a solvent evaporated from said catalyst in step (b).

3. The method of claim 2, wherein a temperature of the solvent-depleted catalyst solution is controlled between 60° C. and 160° C. during the evaporating of step (b).

4. The method of claim 2, wherein the ratio of step (b) is maintained by controlling the composition of 3-pentenenitrile and 2-pentenenitrile in the catalyst solution introduced in step (a).

5. The method of claim 2, wherein the catalyst further comprises at least one monodentate phosphorus containing ligand selected from the group consisting of monodentate phosphite, monodentate phosphonite, monodentate phosphinite, and monodentate phosphine.

6. A method for reacting 3-pentenenitrile (3PN) with hydrogen cyanide in the presence of a catalyst to form adiponitrile, wherein said catalyst comprises nickel and a bidentate phosphorus-containing ligand, and said method comprises the steps of:

(a) obtaining a reaction effluent stream comprising adiponitrile, unreacted 3PN, 2-pentenenitrile (2PN) and catalyst;
   (b) extracting the reaction effluent stream from step (a) with an extraction solvent to obtain an extracted catalyst solution comprising 3PN, 2PN, catalyst and extraction solvent;
   (c) introducing the extracted catalyst solution from step (b) into a distillation zone;
   (d) evaporating solvent from said catalyst in the distillation zone of step (c) to form a solvent-depleted catalyst solution comprising the catalyst, 2-pentenenitrile, and the 3-pentenenitrile while maintaining the 3PN/2PN ratio in said solvent-depleted catalyst solution at 14/1 or less; and (e) contacting the solvent-depleted catalyst solution from step (d) with hydrogen cyanide and Lewis acid to form the adiponitrile.

7. The method of claim 2, wherein the 3PN/2PN ratio in said solvent-depleted catalyst solution is maintained at from 1/1 to 7/1.

8. The method of claim 6, wherein the 3PN/2PN ratio in said solvent-depleted catalyst solution is maintained at from 1/1 to 7/1.

9. The method of claim 2, wherein the solvent of step (b) comprises one or more linear aliphatic hydrocarbons, one or more branched aliphatic hydrocarbons, one or more unsubstituted cycloaliphatic hydrocarbons, one or more alkyl-substituted cycloaliphatic hydrocarbons, and/or one or more aromatic hydrocarbons, and wherein the 3PN/2PN ratio in said solvent-depleted catalyst solution is maintained at from 1/1 to 3/1.

10. The method of claim 2, wherein solvent is evaporated in the distillation zone utilizing a distillation method selected from the group consisting of an adiabatic flash, a distillation at or above one atmosphere pressure, and a vacuum distillation.

\* \* \* \* \*